United States Patent
Ly et al.

(10) Patent No.: US 8,420,639 B2
(45) Date of Patent: Apr. 16, 2013

(54) ARYLSULFONAMIDE CCR3 ANTAGONISTS

(75) Inventors: Tai Wei Ly, San Diego, CA (US); Jared Andrew Forrester, Castle Rock, CO (US)

(73) Assignee: Axikin Pharmaceuticals, Inc., San Diego, CA (US)

( * ) Notice: Subject to any disclaimer, the term of this patent is extended or adjusted under 35 U.S.C. 154(b) by 409 days.

(21) Appl. No.: 12/764,894

(22) Filed: Apr. 21, 2010

(65) Prior Publication Data

US 2010/0273795 A1 Oct. 28, 2010

Related U.S. Application Data

(60) Provisional application No. 61/171,780, filed on Apr. 22, 2009.

(51) Int. Cl.
*A61K 31/5377* (2006.01)
*A61K 31/495* (2006.01)
*A61K 31/496* (2006.01)
*C07D 241/04* (2006.01)
*C07D 413/06* (2006.01)
*C07D 401/06* (2006.01)

(52) U.S. Cl.
USPC .............. 514/235.8; 514/252.12; 514/254.02; 514/253.13; 544/383; 544/367; 544/365; 544/121

(58) Field of Classification Search ............... 514/235.8, 514/252.12, 254.04, 253.13; 544/383, 367, 544/365, 121

See application file for complete search history.

(56) References Cited

U.S. PATENT DOCUMENTS

| | | |
|---|---|---|
| 7,071,180 B2 | 7/2006 | Nilsson et al. |
| 7,674,797 B2 | 3/2010 | Li et al. |
| 7,700,586 B2 | 4/2010 | Li et al. |
| 7,759,339 B2 | 7/2010 | Aertgeerts et al. |
| 2009/0286771 A1 | 11/2009 | Li et al. |

FOREIGN PATENT DOCUMENTS

| | | |
|---|---|---|
| WO | WO 03/022277 | 3/2003 |
| WO | WO 2004/084898 | 10/2004 |

OTHER PUBLICATIONS

Vippagunta et al., Crystalline solids, 2001, Advanced Drug Delivery Reviews, 48, pp. 3 and 18.*
Bischoff et al., "Immunnohistological assessment of intestinal eosinophil activation in patients with eosinophilic gastroenteritis and inflammatory bowel disease," *Am. J. Gastroenterol.* 1999, 94, 3521-3529.
Combadiere et al., "Cloning and functional expression of a human eosinophil CC chemokine receptor," *J. Biol. Chem.* 1995, 270, 16491-16494.
Durham and Kay, "Eosinophils, bronchial hyperreactivity and late-phase asthmatic reactions," *Clin. Allergy* 1985, 15, 411-418.
Durham, "Mechanisms of mucosal inflammation in the nose and lungs," *Clin. Exp. Allergy* 1998, 28 Suppl. 2, 11-16.
Evans et al., "Pretreatment with antibody to eosinophil major basic protein prevents hyperresponsiveness by protecting neuronal M2 muscarinic receptors in antigen-challenged guinea pigs," *J. Clin. Invest.* 1997, 100, 2254-2262.
Fullkerson et al., "A central regulatory role for eosinophils and the eotaxin/CCR3 axis in chronic experimental allergic airway inflammation," *Proc. Natl. Acad. Sci.* USA 2006, 103, 16418-16423.
Grimaldi et al., "Depletion of eosinophils in mice through the use of antibodies specific for C-C chemokine receptor 3 (CCR3)," *J. Leukocyte Biol.* 1999, 65, 846-853.
Heath et al., "Chemokine receptor usage by human eosinophils. The importance of CCR3 demonstrated using an antagonistic monoclonal antibody," *J. Clin. Invest.* 1997. 99, 178-184.
Humbles et al., "The murine CCR3 receptor regulates both the role of eosinophils and mast cells in allergen-induced airway inflammation and hyperresponsiveness," *Proc. Natl. Acad. Sci.* USA 2002, 99, 1479-1484.
Justice et al., "Ablation of eosinophils leads to a reduction of allergen-induced pulmonary pathology," *Am. J. Physiol. Lung Cell. Mol. Physiol.* 2003, 284, L169-L178.
Kroegel et al., "Blood and bronchoalveolar eosinophils in allergic subjects after segmental antigen challenge: surface phenotype, density heterogeneity, and prostanoid production," *J. Allergy Clin. Immunol.* 1994, 93, 725-734.
Leung, "Pathogenesis of atopic dermatitis," *J. Allergy Clin. Immunol.* 1999, 104, S99-108.
Ma et al., "CCR3 is essential for skin eosinophilia and airway hyperresponsiveness in a murine model of allergic skin inflammation," *J. Clin. Invest.* 2002, 109, 621-628.
Pope et al., "The eotaxin chemokines and CCR3 are fundamental regulators of allergen-induced pulmonary eosinophilia," *J. Immunol.* 2005, 175, 5341-5350.
Post et al., "Molecular characterization of two murine eosinophil beta chemokine receptors," *J. Immunol.* 1995, 155, 5299-5305.
Ying et al., "Eosinophil chemotactic chemokines (eotaxin, eotaxin-2, RANTES, monocyte chemoattractant protein-3 (MCP-3), and MCP-4), and C-C chemokine receptor 3 expression in bronchial biopsies from atopic and nonatopic (Intrinsic) asthmatics," *J. Immunol.* 1999, 163, 6321-6329.

* cited by examiner

*Primary Examiner* — Kristin Bianchi
(74) *Attorney, Agent, or Firm* — Jones Day

(57) ABSTRACT

Provided herein are arylsulfonamides that are useful for modulating CCR3 activity, and pharmaceutical compositions thereof. Also provided herein are methods of their use for treating, preventing, or ameliorating one or more symptoms of a CCR3-mediated disorder, disease, or condition.

37 Claims, No Drawings

ARYLSULFONAMIDE CCR3 ANTAGONISTS

CROSS REFERENCE TO RELATED APPLICATIONS

This application claims priority to U.S. Provisional Application No. 61/171,780, filed Apr. 22, 2009, the disclosure of which is incorporated herein by reference in its entirety.

FIELD

Provided herein are arylsulfonamides that are useful for modulating CCR3 activity, and pharmaceutical compositions thereof. Also provided herein are methods of their use for treating, preventing, or ameliorating one or more symptoms of a CCR3-mediated disorder, disease, or condition.

BACKGROUND

CC chemokine receptor 3 (CCR3) is a seven-transmembrane G protein-coupled receptor, which binds to a variety of C—C chemokines, including eotaxin (CCL11), eotaxin-3 (CCL26), MCP-3 (CCL7), MCP-4 (CCL13), and RANTES (CCL5). CCR3 is known to be a major chemokine receptor expressed on allergic inflammatory cells, including eosinophils, basophils, mast cells, and T helper 2-type CD4$^+$ cells (Combadiere et al., *J. Biol. Chem.* 1995, 270, 16491-16494; Post et al., *J. Immunol.* 1995, 155, 5299-5305). Eosinophils have been implicated in the pathogenesis of a number of allergic diseases, such as bronchial asthma (Durham and Kay, *Clin. Allergy* 1985, 15, 411-418; Kroegel et al, *J. Allergy Clin. Immunol.* 1994, 93, 725-734), allergic rhinitis (Durham, *Clin. Exp. Allergy* 1998, 28 Suppl. 2, 11-16.), atopic dermatitis (Leung, *J. Allergy Clin. Immunol.* 1999, 104, S99-108), and eosinophilic gastroenteritis (Bischoff et al., *Am. J. Gastro.* 1999, 94, 3521-3529). It has been demonstrated that activated eosinophils release major basic protein (MBP), which blocks inhibitory M2 muscarinic receptors (M2Rs) on nerves, increasing acetylcholine release, and potentiating vagally mediated bronchoconstriction (Evans et al., *J. Clin. Invest.* 1997, 100, 2254-2262).

Numerous reports indicate that CCR3 plays important roles in allergic conditions. For example, it has been reported that, in both atopic and nonatopic asthma patients, there are increases in both mRNA and protein levels of CCR3 and its ligands, eotaxin, eotaxin-2, RANTES, and MCP-4 (Ying et al., *J. Immunol.* 1999, 99, 6321-6329). It has also been demonstrated that CCR3 gene deletion impairs eosinophil recruitment in an acute model of experimental asthma (Humbles et al., *Proc. Natl. Acad. Sci. USA* 2002, 99, 1479-1484; Ma et al., *J. Clin. Invest.* 2002, 109, 621-628; Pope et al., *J. Immunol.* 2005, 175, 5341-5350; Fulkerson et al., *Proc. Natl. Acad. Sci. USA* 2006, 103, 16418-16423). Furthermore, studies have shown that CCR3 antagonists, such as anti-CCR3 monoclonal antibodies, block binding of CCR3-ligands to either CCR3 transfectants or eosinophils, thus blocking chemotaxis of eosinophils induced by C—C chemokines, such as eotaxin, RANTES, or MCP-3 (Heath et al., *J. Clin. Invest.* 1997, 99, 178-184; Grimaldi et al., *J. Leukocyte Biol.* 1999, 65, 846-853; Justice et al., *Am. J. Physiol.* 2003, 284, L168-L178). Therefore, CCR3 antagonists are potentially useful for the treatment of inflammatory diseases, such as allergic rhinitis and allergic asthma. In addition, CCR3 antagonists are also potentially useful blocking infection of CCR3 expressing cells by some microorganisms, such as HIV, as CCR3 is known to be an entry co-receptor for some microorganisms.

SUMMARY OF THE DISCLOSURE

Provided herein is an arylsulfonamide of Formula I:

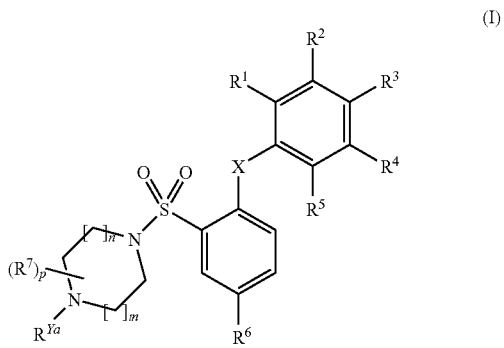

or an enantiomer, a mixture of enantiomers, a mixture of two or more diastereomers, a tautomer, or a mixture of two or more tautomers thereof; or a pharmaceutically acceptable salt, solvate, hydrate, or prodrug thereof;

wherein:

$R^1$, $R^2$, $R^3$, $R^4$, $R^5$, and $R^6$ are each independently (a) hydrogen, halo, cyano, nitro, or guanidine; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —S(O)R$^{1a}$, —S(O)$_2$R$^{1a}$, —S(O)NR$^{1b}$R$^{1c}$, or —S(O)$_2$NR$^{1b}$R$^{1c}$;

$R^7$ is (a) halo, cyano, nitro, oxo, or guanidine; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —S(O)R$^{1a}$, —S(O)$_2$R$^{1a}$, —S(O)NR$^{1b}$R$^{1c}$, or —S(O)$_2$NR$^{1b}$R$^{1c}$;

X is O or S;

$R^{Ya}$ is —C(O)R$^{1a}$, —C(O)OR$^{1a}$, —C(O)NR$^{1b}$R$^{1c}$, —C(S)NR$^{1b}$R$^{1c}$, —C(S)NR$^{1a}$C(O)NR$^{1b}$R$^{1c}$, —C(NR$^{1a}$)NR$^{1b}$R$^{1c}$, —C(NNO$_2$)NR$^{1b}$R$^{1c}$, —S(O)R$^{1a}$, —S(O)$_2$R$^{1a}$, —S(O)NR$^{1b}$R$^{1c}$, or —S(O)$_2$NR$^{1b}$R$^{1c}$; with the proviso that $R^{Ya}$ is neither —C(O)O-t-butyl nor —C(O)H;

m is an integer from 0 to 3;

n is an integer from 1 to 3;

p is an integer from 0 to 4; and each $R^{1a}$, $R^{1b}$, $R^{1c}$, and $R^{1d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or each pair of $R^{1b}$ and $R^{1c}$ together with the N atom to which they are attached independently form heteroaryl or heterocyclyl;

wherein each alkyl, alkenyl, alkynyl, cycloalkyl, aryl, aralkyl, heterocyclyl, and heteroaryl is optionally substituted with one or more groups, each independently selected from (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents Q; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each optionally substituted with one or more, in one embodiment, one, two, three, or four, substituents Q; or (iii) R$^b$ and R$^c$ together with the N atom to which they are attached form heterocyclyl, optionally substituted with one or more, in one embodiment, one, two, three, or four, substituents Q;

wherein each Q is independently selected from the group consisting of (a) cyano, halo, and nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (iii) R$^f$ and R$^g$ together with the N atom to which they are attached form heterocyclyl.

In one embodiment, R$^{Ya}$ is neither —C(O)O—C$_{1-6}$ alkyl nor —C(O)H.

Also provided herein are pharmaceutical compositions comprising a compound disclosed herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof; in combination with one or more pharmaceutically acceptable carriers.

Further provided herein is a method for modulating CCR3 activity, comprising contacting a CCR3 with a therapeutically effective amount of a compound disclosed herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof.

Additionally provided herein is a method for treating, preventing, or ameliorating one or more symptoms of a CCR3-mediated disorder, disease, or condition in a subject, comprising administering to the subject a therapeutically effective amount of a compound disclosed herein, e.g., a compound of Formula I, an enantiomer, a mixture of enantiomers, a mixture of two or more diastereomers, a tautomer, or a mixture of two or more tautomers thereof; or a pharmaceutically acceptable salt, solvate, hydrate, or prodrug thereof.

DETAILED DESCRIPTION

To facilitate understanding of the disclosure set forth herein, a number of terms are defined below.

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term used herein, those in this section prevail unless stated otherwise.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy*, 21st Edition, Lippincott Williams & Wilkins: Philadelphia, Pa., 2005; *Handbook of Pharmaceutical Excipients*, 5th Edition, Rowe et al., Eds., The Pharmaceutical Press and the American Pharmaceutical Association: 2005; and *Handbook of Pharmaceutical Additives*, 3rd Edition, Ash and Ash Eds., Gower Publishing Company: 2007; *Pharmaceutical Preformulation and Formulation*, 2nd Edition, Gibson Ed., CRC Press LLC: Boca Raton, Fla., 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

The term "alkyl" refers to a linear or branched saturated monovalent hydrocarbon radical, wherein the alkyl may optionally be substituted as described herein. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms.

The term "alkenyl" refers to a linear or branched monovalent hydrocarbon radical, which contains one or more, in one embodiment, one to five, in another embodiment, one, carbon-carbon double bond(s). The alkenyl may be optionally substituted as described herein. The term "alkenyl" also embraces radicals having "cis" and "trans" configurations, or alternatively, "Z" and "E" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkynyl" refers to a linear or branched monovalent hydrocarbon radical, which contains one or more, in one embodiment, one to five, in another embodiment, one, carbon-carbon triple bond(s). The alkynyl may be optionally substituted as described herein. The term "alkynyl" also encompasses both linear and branched alkynyl, unless otherwise specified. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynyl groups include, but are not limited to, ethynyl (—C≡CH) and propargyl (—CH$_2$C≡CH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms.

The term "cycloalkyl" refers to a cyclic monovalent hydrocarbon radical, which may be optionally substituted as described herein. In one embodiment, cycloalkyl groups may be saturated, and/or bridged, and/or non-bridged, and/or fused bicyclic groups. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, bicyclo [2.1.1]hexyl, bicyclo[2.2.1]heptyl, decalinyl, and adamantyl.

The term "aryl" refers to a monovalent monocyclic aromatic group and/or monovalent multicyclic aromatic group that contain at least one aromatic carbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may be optionally substituted as described herein.

The term "aralkyl" or "aryl-alkyl" refers to a monovalent alkyl group substituted with aryl. In certain embodiments, the alkyl and aryl moieties are optionally substituted as described herein.

The term "heteroaryl" refers to a monovalent monocyclic aromatic group and/or multicyclic aromatic group that contain at least one aromatic ring, wherein at least one aromatic ring contains one or more heteroatoms independently selected from O, S, and N in the ring. Heteroaryl groups are bonded to the rest of the molecule through the aromatic ring. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, heteroaryl may also be optionally substituted as described herein.

The term "heterocyclyl" or "heterocyclic" refers to a monovalent monocyclic non-aromatic ring system and/or multicyclic ring system that contains at least one non-aromatic ring, wherein one or more of the non-aromatic ring atoms are heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. Heterocyclyl groups are bonded to the rest of the molecule through the non-aromatic ring. In certain embodiments, the heterocyclyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic radicals include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclic may also be optionally substituted as described herein.

The term "halogen", "halide" or "halo" refers to fluorine, chlorine, bromine, and/or iodine.

The term "optionally substituted" is intended to mean that a group, such as an alkyl, alkenyl, alkynyl, cycloalkyl, aryl, aralkyl, heteroaryl, or heterocyclyl group, may be substituted with one or more substituents independently selected from, e.g., (a) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents Q; and (b) halo, cyano (—CN), nitro (—NO$_2$), —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or (iii) R$^b$ and R$^c$ together with the N atom to which they are attached form heteroaryl or heterocyclyl, optionally substituted with one or more, in one embodiment, one, two, three, or four, substituents Q. As used herein, all groups that can be substituted are "optionally substituted," unless otherwise specified.

In one embodiment, each Q is independently selected from the group consisting of (a) cyano, halo, and nitro; and (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^f$ and R$^g$ together with the N atom to which they are attached form heteroaryl or heterocyclyl.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of one enantiomer and about 5% or less of the other enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The term "solvate" refers to a compound provided herein or a salt thereof, which further includes a stoichiometric or non-stoichiometric amount of solvent bound by non-covalent intermolecular forces. Where the solvent is water, the solvate is a hydrate.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" refers to a material that is not found in nature or that has been structurally modified or synthesized by man.

The term "CCR3" refers to CC chemokine receptor 3 or a variant thereof, which is capable of mediating a cellular response to a variety of chemokines, including, but not limited to, eotaxin (CCL11), eotaxin-3 (CCL26), MCP-3 (CCL7), MCP-4 (CCL13), and RANTES (CCL5). CCR3 variants include proteins substantially homologous to a native CCR3, i.e., proteins having one or more naturally or non-naturally occurring amino acid deletions, insertions or substitutions (e.g., CCR3 derivatives, homologs and fragments), as compared to the amino acid sequence of a native CCR3. The amino acid sequence of a CCR3 variant is at least about 80% identical, at least about 90% identical, or at least about 95% identical to a native CCR3.

The term "CCR3 antagonist" refers to a compound that, e.g., partially or totally blocks, decreases, prevents, inhibits, or downregulates CCR3 activity. The term "CCR3 antagonist" also refers to a compound that binds to, delays the activation of, inactivates, or desensitizes a CCR3 receptor. A CCR3 antagonist may act by interfering with the interaction of a CCR3 receptor and its chemokine ligand, including, but not limited to, eotaxin (CCL11), eotaxin-3 (CCL26), MCP-3 (CCL7), MCP-4 (CCL13), and/or RANTES (CCL5).

The terms "CCR3-mediated disorder or disease" and "a condition, disorder or disease mediated by CCR3" refer to a condition, disorder, or disease characterized by inappropriate, e.g., less than or greater than normal, CCR3 activity. Inappropriate CCR3 functional activity might arise as the result of CCR3 expression in cells which normally do not express CCR3, increased CCR3 expression or degree of intracellular activation, leading to, e.g., inflammatory and immune-related disorders or diseases; or decreased CCR3 expression. A CCR3-mediated condition, disorder or disease may be completely or partially mediated by inappropriate CCR3 activity. In particular, a CCR3-mediated condition, disorder or disease is one in which modulation of a CCR3 receptor results in some effect on the underlying condition or disorder, e.g., a CCR3 antagonist or agonist results in some improvement in at least some of patients being treated.

Compounds

Provided herein are arylsulfonamides which are useful for modulating CCR3 activity. Also provided herein are pharmaceutical compositions which comprise the compounds and methods of use of the compounds and compositions for the treatment of a CCR3-mediated disorder, disease, or condition.

In one embodiment, provided herein is an arylsulfonamide of Formula I:

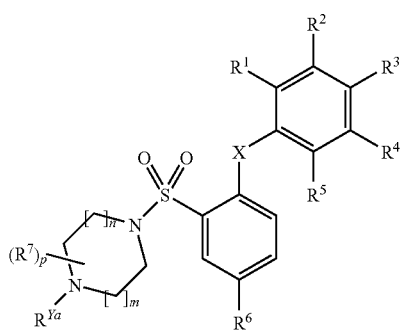

(I)

or an enantiomer, a mixture of enantiomers, a mixture of two or more diastereomers, a tautomer, or a mixture of two or more tautomers thereof; or a pharmaceutically acceptable salt, solvate, hydrate, or prodrug thereof;

wherein:

$R^1$, $R^2$, $R^3$, $R^4$, $R^5$, and $R^6$ are each independently (a) hydrogen, halo, cyano, nitro, or guanidine; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^7$ is (a) halo, cyano, nitro, oxo, or guanidine; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

X is O or S;

$R^{Ya}$ is —C(O)$R^{1a}$, —C(O)O$R^{1a}$, —C(O)N$R^{1b}R^{1c}$, —C(S)N$R^{1b}R^{1c}$, —C(S)N$R^{1a}$C(O)N$R^{1b}R^{1c}$, —C(N$R^{1a}$)N$R^{1b}R^{1c}$, —C(NNO$_2$)N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$;

m is an integer from 0 to 3;

n is an integer from 1 to 3;

p is an integer from 0 to 4; and each $R^{1a}$, $R^{1b}$, $R^{1c}$, and $R^{1d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or each pair of $R^{1b}$ and $R^{1c}$ together with the N atom to which they are attached independently form heteroaryl or heterocyclyl;

wherein each alkyl, alkenyl, alkynyl, cycloalkyl, aryl, aralkyl, heterocyclyl, and heteroaryl is optionally substituted with one or more groups, each independently selected from (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents Q; and (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or (iii) $R^b$ and $R^c$ together with the N atom to which they are attached form heterocyclyl, optionally substituted with one or more, in one embodiment, one, two, three, or four, substituents Q;

wherein each Q is independently selected from the group consisting of (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(N$R^e$)N$R^fR^g$, —O$R^e$, —OC(O)$R^e$, —OC(O)O$R^e$, —OC(O)N$R^fR^g$, —OC(=N$R^e$)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^h$, —N$R^e$C(O)N$R^fR^g$, —N$R^e$C(=N$R^h$)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —S$R^e$, —S(O)$R^e$, —S(O)$_2R^e$, —S(O)N$R^fR^g$, and —S(O)$_2$N$R^fR^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

In certain embodiments, in Formula I, $R^{Ya}$ is neither —C(O)O-t-butyl nor —C(O)H.

In certain embodiments, in Formula I, $R^{Ya}$ is neither —C(O)O-t-butyl nor —C(O)H. In certain embodiments, in Formula I, $R^{Ya}$ is not —C(O)O-t-butyl. In certain embodiments, in Formula I, the compound is 4-(2-(3,5-dimethylphenoxy)-5-nitrophenylsulfonyl)piperazine-1-carbaldehyde.

In another embodiment, provided herein is an arylsulfonamide of Formula I:

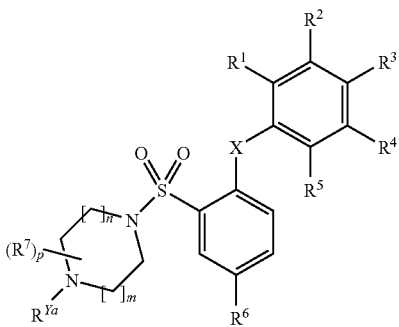

(I)

or an enantiomer, a mixture of enantiomers, a mixture of two or more diastereomers, a tautomer, or a mixture of two or more tautomers thereof; or a pharmaceutically acceptable salt, solvate, hydrate, or prodrug thereof;

wherein:

$R^1$, $R^2$, $R^3$, $R^4$, $R^5$, and $R^6$ are each independently (a) hydrogen, halo, cyano, nitro, or guanidine; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^7$ is (a) halo, cyano, nitro, oxo, or guanidine; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

X is O or S;

$R^{Ya}$ is —C(O)$R^{1a}$, —C(O)O$R^{1a}$, —C(O)N$R^{1b}R^{1c}$, —C(N$R^{1a}$)N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$; with the proviso that $R^{Ya}$ is neither —C(O)O-t-butyl nor —C(O)H;

m is an integer from 0 to 3;

n is an integer from 1 to 3;

p is an integer from 0 to 4; and each $R^{1a}$, $R^{1b}$, $R^{1c}$, and $R^{1d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or each pair of $R^{1b}$ and $R^{1c}$ together with the N atom to which they are attached independently form heteroaryl or heterocyclyl;

wherein each alkyl, alkenyl, alkynyl, cycloalkyl, aryl, aralkyl, heterocyclyl, and heteroaryl is optionally substituted with one or more groups, each independently selected from (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents Q; and (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or (iii) $R^b$ and $R^c$ together with the N atom to which they are attached form heterocyclyl, optionally substituted with one or more, in one embodiment, one, two, three, or four, substituents Q;

wherein each Q is independently selected from the group consisting of (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(N$R^e$)N$R^fR^g$, —O$R^e$, —OC(O)$R^e$, —OC(O)O$R^e$, —OC(O)N$R^fR^g$, —OC(=N$R^e$)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^h$, —N$R^e$C(O)N$R^fR^g$, —N$R^e$C(=N$R^h$)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —S$R^e$, —S(O)$R^e$, —S(O)$_2R^e$, —S(O)N$R^fR^g$, and —S(O)$_2$N$R^fR^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

In one embodiment, $R^{Ya}$ is neither —C(O)O—$C_{1-6}$ alkyl nor —C(O)H. In another embodiment, $R^{Ya}$ is —C(O)O—$C_{1-6}$ alkyl, but not —C(O)O-t-butyl.

In one embodiment, in Formula I, $R^1$, $R^2$, $R^3$, $R^4$, and $R^5$ are each independently hydrogen, halo, or $C_{1-6}$ alkyl;

$R^6$ is cyano or nitro;

$R^7$ is $C_{1-6}$ alkyl;

X is O or S;

m is 0, 1, or 2;

n is 1 or 2;

p is 0, 1, 2, 3, or 4; and $R^{Ya}$ is —C(O)$R^{1a}$, —C(O)O$R^{1a}$, —C(O)N$R^{1b}R^{1c}$, —C(S)N$R^{1b}R^{1c}$, —C(S)N$R^{1a}$C(O)N$R^{1b}R^{1c}$, —C(NNO$_2$)N$R^{1b}R^{1c}$, —S(O)$_2R^{1a}$, or —S(O)$_2$N$R^{1b}R^{1c}$; (wherein each $R^{1a}$ and $R^{1c}$ is independently (a) hydrogen; (b) $C_{1-6}$ alkyl, optionally substituted with one, two, or three substituents, each of which is independently selected from cyano, halo, $C_{3-7}$ cycloalkyl, $C_{6-14}$ aryl, heteroaryl, heterocyclyl, —C(O)$R^a$, —C(O)O$R^a$, and —S$R^a$, where the cycloalkyl, aryl, heteroaryl, and heterocyclyl are each further optionally substituted with one, two, or three substituents, each of which is independently halo or $C_{1-6}$ alkyl; (c) $C_{1-6}$ alkenyl, optionally substituted with $C_{6-14}$ aryl; (d) $C_{3-7}$ cycloalkyl, optionally substituted with one or two $C_{1-6}$ alkyl; (e) $C_{6-14}$ aryl, optionally substituted with one, two, or three substituents, each of which is independently selected from halo, nitro, cyano, —O$R^a$, —C(O)$R^a$, and $C_{1-6}$ alkyl, where the alkyl is further optionally substituted with one, two, or three halo; (f) heteroaryl, optionally substituted with one, two, or three substituents, each of which is independently halo or $C_{1-6}$ alkyl; or (g) heterocyclyl; and $R^{1b}$ is hydrogen or $C_{1-6}$ alkyl.

In another embodiment, in Formula I, $R^1$, $R^2$, $R^3$, $R^4$, and $R^5$ are each independently hydrogen, halo, or $C_{1-6}$ alkyl;

$R^6$ is cyano or nitro;

$R^7$ is $C_{1-6}$ alkyl;
X is O or S;
m is 0, 1, or 2;
n is 1 or 2;
p is 0, 1, 2, 3, or 4; and
$R^{Ya}$ is —C(O)$R^{1a}$, —C(O)O$R^{1a}$, —C(O)N$R^{1b}R^{1c}$, —C(S)N$R^{1b}R^{1c}$, —C(S)N$R^{1a}$C(O)N$R^{1b}R^{1c}$, —C(NNO$_2$)N$R^{1b}R^{1c}$, —S(O)$_2R^{1a}$, or —S(O)$_2$N$R^{1b}R^{1c}$; wherein each $R^{1a}$ and $R^{1c}$ is independently (a) hydrogen; or (b) $C_{1-6}$ alkyl, $C_{2-6}$ alkenyl, $C_{3-7}$ cycloalkyl, $C_{6-14}$ aryl, heteroaryl, or heterocyclyl, each optionally substituted with one or two substituents, each of which is independently selected from halo, cyano, nitro, $C_{1-6}$ alkyl, $C_{3-7}$ cycloalkyl, $C_{6-14}$ aryl, heteroaryl, heterocyclyl, —O$R^a$, —S$R^a$, and —C(O)$R^a$, where $R^a$ is as defined herein and the alkyl, cycloalkyl, aryl, heteroaryl, and heterocyclyl are each optionally further substituted with one or two substituents, each of which is independently halo or $C_{1-6}$ alkyl; and $R^{1b}$ is hydrogen or $C_{1-6}$ alkyl.

In yet another embodiment, in Formula I,
$R^1$, $R^2$, $R^3$, $R^4$, and $R^5$ are each independently hydrogen, halo, or $C_{1-6}$ alkyl;
$R^6$ is cyano or nitro;
$R^7$ is $C_{1-6}$ alkyl;
X is O or S;
m is 0, 1, or 2;
n is 1 or 2;
p is 0, 1, 2, 3, or 4; and
$R^{Ya}$ is —C(O)$R^{1a}$, —C(O)O$R^{1a}$, —C(O)N$R^{1b}R^{1c}$, —C(S)N$R^{1b}R^{1c}$, —C(S)N$R^{1a}$C(O)N$R^{1b}R^{1c}$, —C(NNO$_2$)N$R^{1b}R^{1c}$, —S(O)$_2R^{1a}$, or —S(O)$_2$N$R^{1b}R^{1c}$; (wherein each $R^{1a}$ and $R^{1c}$ is independently (a) hydrogen; or (b) $C_{1-6}$ alkyl, $C_{2-6}$ alkenyl, $C_{3-7}$ cycloalkyl, $C_{6-14}$ aryl, heteroaryl, or heterocyclyl, each optionally substituted with one or two substituents, each of which is independently selected from fluoro, chloro, cyano, nitro, methyl, trifluoromethyl, ethyl, methoxy, ethoxy, methylthio, (1S,2S,4R)-7,7-dimethylbicyclo[2.2.1]-heptyl, phenyl, chlorophenyl, furanyl, morpholinyl, acetyl, propionyl, and ethoxycarbonyl; and $R^{1b}$ is hydrogen or $C_{1-6}$ alkyl.

In yet another embodiment, in Formula I,
$R^1$, $R^2$, $R^3$, $R^4$, and $R^5$ are each independently hydrogen, halo, or $C_{1-6}$ alkyl;
$R^6$ is cyano or nitro;
$R^7$ is $C_{1-6}$ alkyl;
X is O or S;
m is 0, 1, or 2;
n is 1 or 2;
p is 0, 1, 2, 3, or 4; and
$R^{Ya}$ is —C(O)$R^{1a}$, —C(O)O$R^{1a}$, —C(O)N$R^{1b}R^{1c}$, —C(S)N$R^{1b}R^{1c}$, —C(S)N$R^{1a}$C(O)N$R^{1b}R^{1c}$, —C(NNO$_2$)N$R^{1b}R^{1c}$, —S(O)$_2R^{1a}$, or —S(O)$_2$N$R^{1b}R^{1c}$; wherein $R^{1a}$ and $R^{1c}$ are each independently (a) hydrogen; (b) $C_{1-6}$ alkyl, optionally substituted with a substituent selected from chloro, cyano, ethoxy, methylthio, (1S,2S,4R)-7,7-dimethylbicyclo[2.2.1]-heptyl, phenyl, chlorophenyl, furanyl, morpholinyl, propionyl, and ethoxycarbonyl; (c) $C_{2-6}$ alkenyl, optionally substituted with phenyl; (d) $C_{3-7}$ cycloalkyl; (e) $C_{6-14}$ aryl, optionally substituted with one or two substituents, each independently selected from fluoro, chloro, cyano, nitro, methyl, trifluoromethyl, ethyl, methoxy, and acetyl; (f) heteroaryl, optionally substituted with one or two methyl; or (g) heterocyclyl; and $R^{1b}$ is hydrogen or $C_{1-6}$ alkyl.

In yet another embodiment, in Formula I,
$R^1$, $R^2$, $R^3$, $R^4$, and $R^5$ are each independently hydrogen, chloro, or methyl;
$R^6$ is cyano or nitro;
X is O or S;
m is 0, 1, or 2;
n is 1 or 2;
p is 0; and
$R^{Ya}$ is —C(O)$R^{1a}$, —C(O)O$R^{1a}$, —C(O)N$R^{1b}R^{1c}$, —C(S)N$R^{1b}R^{1c}$, —C(S)N$R^{1a}$C(O)N$R^{1b}R^{1c}$, —C(NNO$_2$)N$R^{1b}R^{1c}$, —S(O)$_2R^{1a}$, or —S(O)$_2$N$R^{1b}R^{1c}$; wherein $R^{1a}$ and $R^{1c}$ are each independently (a) hydrogen; (b) methyl, ethyl, propyl (e.g., n-propyl or isopropyl), butyl (e.g., n-butyl, 2-butyl, isobutyl, or t-butyl), or pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl), each optionally substituted with a substituent selected from chloro, cyano, ethoxy, methylthio, (1S,2S,4R)-7,7-dimethylbicyclo[2.2.1]-heptyl, phenyl, chlorophenyl, furanyl, morpholinyl, propionyl, and ethoxycarbonyl; (c) ethenyl or allyl, each optionally substituted with phenyl; (d) cyclobutyl, cyclopentyl, or cyclohexyl; (e) phenyl, optionally substituted with one or two substituents, each independently selected from fluoro, chloro, cyano, nitro, methyl, trifluoromethyl, ethyl, methoxy, and acetyl; (f) furanyl, thienyl, isoxazolyl, pyrazolyl, 1,2,3-thiadiazolyl, pyridinyl, pyrazyl, benzofuranyl, benzo[c][1,2,5]oxadiazolyl, benzothienyl, or benzothiazolyl, each optionally substituted with one or two methyl; or (g) morpholinyl; and $R^{1b}$ is hydrogen, methyl, or ethyl.

In yet another embodiment, in Formula I,
$R^1$, $R^2$, $R^3$, $R^4$, and $R^5$ are each independently hydrogen, chloro, or methyl;
$R^6$ is cyano or nitro;
X is O or S;
m is 0, 1, or 2;
n is 1 or 2;
p is 0; and
$R^{Ya}$ is —C(O)$R^{1a}$, —C(O)O$R^{1a}$, —C(O)N$R^{1b}R^{1c}$, —C(S)N$R^{1b}R^{1c}$, —C(S)N$R^{1a}$C(O)N$R^{1b}R^{1c}$, —C(NNO$_2$)N$R^{1b}R^{1c}$, —S(O)$_2R^{1a}$, or —S(O)$_2$N$R^{1b}R^{1c}$; wherein each $R^{1a}$ and $R^{1c}$ is independently hydrogen, methyl, ethyl, propyl (e.g., n-propyl or isopropyl), butyl (e.g., n-butyl, 2-butyl, isobutyl, or t-butyl), or pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl), chloroethyl, chloropropyl, chlorobutyl, ethoxycarbonylethyl, methylthiopropyl, cyanomethyl, (1S,2S,4R)-7,7-dimethylbicyclo[2.2.1]-heptylmethyl, benzyl, chlorobenzyl, furanylemthyl, morpholinylethyl, propionylethyl, ethenyl, allyl, phenylethenyl, cyclobutyl, cyclopentyl, cyclohexyl, phenyl, chlorophenyl (e.g., 2-chlorophenyl, 3-chlorophenyl, or 4-chlorophenyl), fluorophenyl (e.g., 2-fluorophenyl, 3-fluorophenyl, or 4-fluorophenyl), cyanophenyl (e.g., 2-cyanophenyl, 3-cyanophenyl, or 4-cyanophenyl), nitrophenyl (e.g., 2-nitrophenyl, 3-nitrophenyl, or 4-nitrophenyl), methylphenyl (e.g., 2-methylphenyl, 3-methylphenyl, or 4-methylphenyl), trifluoromethylphenyl (e.g., 2-trifluoromethylphenyl, 3-trifluoromethylphenyl, or 4-trifluoromethylphenyl), ethylphenyl (e.g., 2-ethylphenyl, 3-ethylphenyl, or 4-ethylphenyl), methoxyphenyl (e.g., 2-methoxyphenyl, 3-methoxyphenyl, or 4-methoxyphenyl), acetylphenyl (e.g., 2-acetylphenyl, 3-acetylphenyl, or 4-acetylphenyl), dichlorophenyl (e.g., 2,3-dichlorophenyl, 2,4-dichlorophenyl, 2,5-dichlorophenyl, 2,6-dichlorophenyl, 3,4-dichlorophenyl, or 3,5-dichlorophenyl), furanyl (e.g., furan-2-yl or furan-3-yl), thienyl (e.g., thien-2-yl or thien-3-yl), methyl-thienyl, isoxazolyl, dimethylpyrazolyl, methyl-1,2,3-thiadiazolyl, pyridinyl (e.g., pyridin-2-yl, pyridin-3-yl, or pyridin-4-yl), pyrazyl (e.g., 2-pyrazyl or 3-pyrazyl), benzofuranyl, benzo[c][1,2,5]oxadiazolyl, benzothienyl, benzothiazolyl, or morpholinyl; and
each $R^{1b}$ is independently hydrogen, methyl, or ethyl.

In still another embodiment, in Formula I,
$R^1$ is hydrogen;

$R^2$ is chloro or methyl;
$R^3$ is hydrogen;
$R^4$ is chloro or methyl;
$R^5$ is hydrogen;
$R^6$ is cyano;
X is O or S;
m is 1;
n is 1;
p is 0; and
$R^{Ya}$ is —C(O)$R^{1a}$, —C(O)O$R^{1a}$, —C(O)N$R^{1b}R^{1c}$, —C(S)N$R^{1b}R^{1c}$, —C(S)N$R^{1a}$C(O)N$R^{1b}R^{1c}$, —C(NNO$_2$)N$R^{1b}R^{1c}$, —S(O)$_2R^{1a}$, or —S(O)$_2$N$R^{1b}R^{1c}$; wherein each $R^{1a}$ and $R^{1c}$ is independently hydrogen, methyl, ethyl, isopropyl, isobutyl, t-butyl, 1,1-dimethylpropyl, 2,2-dimethylpropyl, 2-chloroethyl, 3-chloropropyl, 4-chlorobutyl, 2-ethoxycarbonylethyl, 3-methylthiopropyl, 1-cyanomethyl, (1S,2S,4R)-7,7-dimethylbicyclo[2.2.1]-heptylmethyl, benzyl, 3-chlorobenzyl, furan-2-ylmethyl, 2-morpholin-4-ylethyl, 2-propionylethyl, ethenyl, allyl, 2-phenylethenyl, cyclobutyl, cyclopentyl, cyclohexyl, phenyl, 2-chlorophenyl, 3-chlorophenyl, 4-chlorophenyl, 2-fluorophenyl, 3-fluorophenyl, 4-fluorophenyl, 4-cyanophenyl, 4-nitrophenyl, 2-methylphenyl, 3-methylphenyl, 4-methylphenyl, 4-trifluoromethylphenyl, 4-ethylphenyl, 4-methoxyphenyl, 3-acetylphenyl, 3,4-dichlorophenyl, furan-2-yl, thien-2-yl, 3-methyl-thien-2-yl, isoxazol-5-yl, 2,5-dimethylpyrazol-3-yl, 4-methyl-1,2,3-thiadiazol-5-yl, pyridin-2-yl, 2-pyrazyl, benzofuran-2-yl, benzo[c][1,2,5]oxadiazol-5-yl, benzothien-2-yl, benzothiazol-2-yl, or morpholin-4-yl; and each $R^{1b}$ is independently hydrogen, methyl, or ethyl.

In one embodiment, in Formula I,
$R^1$, $R^2$, $R^3$, $R^4$, and $R^5$ are each independently hydrogen, halo, or $C_{1-6}$ alkyl;
$R^6$ is cyano or nitro;
$R^7$ is $C_{1-6}$ alkyl;
X is O or S;
m is 0, 1, or 2;
n is 1 or 2;
p is 0, 1, 2, 3, or 4; and
$R^{Ya}$ is —C(O)$R^{1a}$, —C(O)N$R^{1b}R^{1c}$, or —S(O)$_2R^{1a}$; wherein $R^{1a}$ and $R^{1c}$ are each independently $C_{1-6}$ alkyl; $C_{3-7}$ cycloalkyl, optionally substituted with one or two $C_{1-6}$ alkyl; or $C_{6-14}$ aryl, optionally substituted with one or more halo or $C_{1-6}$ alkyl, where the alkyl is further optionally substituted with one, two, or three halo; and $R^{1b}$ is hydrogen.

In another embodiment, in Formula I,
$R^1$, $R^2$, $R^3$, $R^4$, and $R^5$ are each independently hydrogen, halo, or $C_{1-6}$ alkyl;
$R^6$ is cyano or nitro;
$R^7$ is $C_{1-6}$ alkyl;
X is O or S;
m is 0, 1, or 2;
n is 1 or 2;
p is 0, 1, 2, 3, or 4; and
$R^{Ya}$ is —C(O)$R^{1a}$, —C(O)N$R^{1b}R^{1c}$, or —S(O)$_2R^{1a}$; wherein $R^{1a}$ and $R^{1c}$ are each independently $C_{1-6}$ alkyl; $C_{3-7}$ cycloalkyl, optionally substituted with two methyl groups; or $C_{6-14}$ aryl, optionally substituted with fluoro, chloro, methyl, trifluoromethyl, or ethyl; and $R^{1b}$ is hydrogen.

In yet another embodiment, in Formula I,
$R^1$, $R^2$, $R^3$, $R^4$, and $R^5$ are each independently hydrogen, chloro, or methyl;
$R^6$ is cyano or nitro;
X is O or S;
m is 0, 1, or 2;
n is 1 or 2;
p is 0; and
$R^{Ya}$ is —C(O)$R^{1a}$, —C(O)N$R^{1b}R^{1c}$, or —S(O)$_2R^{1a}$; wherein $R^{1a}$ and $R^{1c}$ are each independently methyl, ethyl, propyl (e.g., n-propyl or isopropyl), butyl (e.g., n-butyl, 2-butyl, isobutyl, or t-butyl), pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl), cyclobutyl, cyclopentyl, cyclohexyl, dimethylbicyclo[2.2.1]heptyl (e.g., 7,7-dimethylbicyclo[2.2.1]-heptyl), phenyl, fluorophenyl (e.g., 2-fluorophenyl, 3-fluorophenyl, or 4-fluorophenyl), chlorophenyl (e.g., 2-chlorophenyl, 3-chlorophenyl, or 4-chlorophenyl), methylphenyl (e.g., 2-methylphenyl, 3-methylphenyl, or 4-methylphenyl), trifluoromethylphenyl (e.g., 2-trifluoromethylphenyl, 3-trifluoromethylphenyl, or 4-trifluoromethylphenyl), or ethylphenyl (e.g., 2-ethylphenyl, 3-ethylphenyl, or 4-ethylphenyl); and $R^{1b}$ is hydrogen.

In still another embodiment, in Formula I,
$R^1$ is hydrogen;
$R^2$ is chloro or methyl;
$R^3$ is hydrogen;
$R^4$ is chloro or methyl;
$R^5$ is hydrogen;
$R^6$ is cyano;
X is O or S;
m is 1;
n is 1;
p is 0; and
$R^{Ya}$ is —C(O)$R^{1a}$, —C(O)N$R^{1b}R^{1c}$, or —S(O)$_2R^{1a}$; wherein $R^{1a}$ and $R^{1c}$ are each independently methyl, ethyl, isopropyl, isobutyl, t-butyl, 1,1-dimethylpropyl, 2,2-dimethylpropyl, cyclobutyl, cyclopentyl, cyclohexyl, (1S,2S,4R)-7,7-dimethylbicyclo[2.2.1]-heptyl, phenyl, 2-chlorophenyl, 4-chlorophenyl, 2-fluorophenyl, 3-fluorophenyl, 4-fluorophenyl, 2-methylphenyl, 3-methylphenyl, 4-methylphenyl, 4-trifluoromethylphenyl, or 4-ethylphenyl; and $R^{1b}$ is hydrogen.

The groups, $R^1$, $R^2$, $R^3$, $R^4$, $R^5$, $R^6$, $R^7$, $R^{1a}$, $R^{1b}$, $R^{1c}$, $R^{1d}$, $R^{Ya}$, X, m, n, and p in Formula I are further defined in the embodiments described herein. All combinations of the embodiments provided herein for such groups are within the scope of this disclosure.

In certain embodiments, $R^1$ is hydrogen, halo, cyano, nitro, or guanidine. In certain embodiments, $R^1$ is hydrogen. In certain embodiments, $R^1$ is halo. In certain embodiments, $R^1$ is fluoro or chloro. In certain embodiments, $R^1$ is $C_{1-6}$ alkyl, optionally substituted as described herein. In certain embodiments, $R^1$ is $C_{1-6}$ alkyl, optionally substituted with one, two, or three halo. In certain embodiments, $R^1$ is methyl, ethyl, propyl (e.g., n-propyl and isopropyl), butyl (e.g., n-butyl, 2-butyl, isobutyl, or t-butyl), or pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, $R^1$ is methyl. In certain embodiments, $R^1$ is $C_{1-6}$ alkoxy, optionally substituted as described herein. In certain embodiments, $R^1$ is $C_{1-6}$ alkoxy, optionally substituted with one, two, or three halo. In certain embodiments, $R^1$ is $C_{2-6}$ alkylthio, optionally substituted as described herein. In certain embodiments, $R^1$ is $C_{1-6}$ alkylthio, optionally substituted with one, two, or three halo. In certain embodiments, $R^1$ is $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted as described herein. In certain embodiments, $R^1$ is —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S (O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; wherein R$^{1a}$, R$^{1b}$, R$^{1c}$, and R$^{1d}$ are each as defined herein.

In certain embodiments, R$^2$ is hydrogen, halo, cyano, nitro, or guanidine. In certain embodiments, R$^2$ is hydrogen. In certain embodiments, R$^2$ is halo. In certain embodiments, R$^2$ is fluoro or chloro. In certain embodiments, R$^2$ is C$_{1-6}$ alkyl, optionally substituted as described herein. In certain embodiments, R$^2$ is C$_{1-6}$ alkyl, optionally substituted with one, two, or three halo. In certain embodiments, R$^2$ is methyl, ethyl, propyl (e.g., n-propyl and isopropyl), butyl (e.g., n-butyl, 2-butyl, isobutyl, or t-butyl), or pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, R$^2$ is methyl. In certain embodiments, R$^2$ is C$_{1-6}$ alkoxy, optionally substituted as described herein. In certain embodiments, R$^2$ is C$_{1-6}$ alkoxy, optionally substituted with one, two, or three halo. In certain embodiments, R$^2$ is C$_{2-6}$ alkylthio, optionally substituted as described herein. In certain embodiments, R$^2$ is C$_{1-6}$ alkylthio, optionally substituted with one, two, or three halo. In certain embodiments, R$^2$ is C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each optionally substituted as described herein. In certain embodiments, R$^2$ is —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; wherein R$^{1a}$, R$^{1b}$, R$^{1c}$, and R$^{1d}$ are each as defined herein.

In certain embodiments, R$^3$ is hydrogen, halo, cyano, nitro, or guanidine. In certain embodiments, R$^3$ is hydrogen. In certain embodiments, R$^3$ is halo. In certain embodiments, R$^3$ is fluoro or chloro. In certain embodiments, R$^3$ is C$_{1-6}$ alkyl, optionally substituted as described herein. In certain embodiments, R$^3$ is C$_{1-6}$ alkyl, optionally substituted with one, two, or three halo. In certain embodiments, R$^3$ is methyl, ethyl, propyl (e.g., n-propyl and isopropyl), butyl (e.g., n-butyl, 2-butyl, isobutyl, or t-butyl), or pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, R$^3$ is methyl. In certain embodiments, R$^3$ is C$_{1-6}$ alkoxy, optionally substituted as described herein. In certain embodiments, R$^3$ is C$_{1-6}$ alkoxy, optionally substituted with one, two, or three halo. In certain embodiments, R$^3$ is C$_{2-6}$ alkylthio, optionally substituted as described herein. In certain embodiments, R$^3$ is C$_{1-6}$ alkylthio, optionally substituted with one, two, or three halo. In certain embodiments, R$^3$ is C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each optionally substituted as described herein. In certain embodiments, R$^3$ is —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; wherein R$^{1a}$, R$^{1b}$, R$^{1c}$, and R$^{1d}$ are each as defined herein.

In certain embodiments, R$^4$ is hydrogen, halo, cyano, nitro, or guanidine. In certain embodiments, R$^4$ is hydrogen. In certain embodiments, R$^4$ is halo. In certain embodiments, R$^4$ is fluoro or chloro. In certain embodiments, R$^4$ is C$_{1-6}$ alkyl, optionally substituted as described herein. In certain embodiments, R$^4$ is C$_{1-6}$ alkyl, optionally substituted with one, two, or three halo. In certain embodiments, R$^4$ is methyl, ethyl, propyl (e.g., n-propyl and isopropyl), butyl (e.g., n-butyl, 2-butyl, isobutyl, or t-butyl), or pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, R$^4$ is methyl. In certain embodiments, R$^4$ is C$_{1-6}$ alkoxy, optionally substituted as described herein. In certain embodiments, R$^4$ is C$_{1-6}$ alkoxy, optionally substituted with one, two, or three halo. In certain embodiments, R$^4$ is C$_{2-6}$ alkylthio, optionally substituted as described herein. In certain embodiments, R$^4$ is C$_{1-6}$ alkylthio, optionally substituted with one, two, or three halo. In certain embodiments, R$^4$ is C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each optionally substituted as described herein. In certain embodiments, R$^4$ is —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$, wherein R$^{1a}$, R$^{1b}$, R$^{1c}$, and R$^{1d}$ are each as defined herein.

In certain embodiments, R$^5$ is hydrogen, halo, cyano, nitro, or guanidine. In certain embodiments, R$^5$ is hydrogen. In certain embodiments, R$^5$ is halo. In certain embodiments, R$^5$ is fluoro or chloro. In certain embodiments, R$^5$ is C$_{1-6}$ alkyl, optionally substituted as described herein. In certain embodiments, R$^5$ is C$_{1-6}$ alkyl, optionally substituted with one, two, or three halo. In certain embodiments, R$^5$ is methyl, ethyl, propyl (e.g., n-propyl and isopropyl), butyl (e.g., n-butyl, 2-butyl, isobutyl, or t-butyl), or pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, R$^5$ is methyl. In certain embodiments, R$^5$ is C$_{1-6}$ alkoxy, optionally substituted as described herein. In certain embodiments, R$^5$ is C$_{1-6}$ alkoxy, optionally substituted with one, two, or three halo. In certain embodiments, R$^5$ is C$_{2-6}$ alkylthio, optionally substituted as described herein. In certain embodiments, R$^5$ is C$_{1-6}$ alkylthio, optionally substituted with one, two, or three halo. In certain embodiments, R$^5$ is C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each optionally substituted as described herein. In certain embodiments, R$^5$ is —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; wherein R$^{1a}$, R$^{1b}$, R$^{1c}$, and R$^{1d}$ are each as defined herein.

In certain embodiments, two of R$^1$, R$^2$, R$^3$, R$^4$, and R$^5$ are halo or C$_{1-6}$ alkyl, optionally substituted as described herein. In certain embodiments, two of R$^1$, R$^2$, R$^3$, R$^4$, and R$^5$ are halo or C$_{1-6}$ alkyl, which is optionally substituted as described herein, and the remaining three are hydrogen. In certain embodiments, two of $R^1$, $R^2$, $R^3$, $R^4$, and $R^5$ are chloro or methyl. In certain embodiments, two of $R^1$, $R^2$, $R^3$, $R^4$, and $R^5$ are chloro or methyl, and the remaining three are hydrogen. In certain embodiments, $R^1$, $R^3$, and $R^5$ are hydrogen, and $R^2$ and $R^4$ are halo or $C_{1-6}$ alkyl, optionally substituted as described herein. In certain embodiments, $R^1$, $R^3$, and $R^5$ are hydrogen, and $R^2$ and $R^4$ are chloro or methyl. In certain embodiments, $R^1$, $R^3$, and $R^5$ are hydrogen, and $R^2$ and $R^4$ are chloro. In certain embodiments, $R^1$, $R^3$, and $R^5$ are hydrogen, and $R^2$ and $R^4$ are methyl. In certain embodiments, $R^2$, $R^3$, and $R^5$ are hydrogen, and $R^1$ and $R^4$ are halo or $C_{1-6}$ alkyl, optionally substituted as described herein. In certain embodiments, $R^2$, $R^3$, and $R^5$ are hydrogen, and $R^1$ and $R^4$ are chloro or methyl. In certain embodiments, $R^2$, $R^3$, and $R^5$ are hydrogen, and $R^1$ and $R^4$ are chloro. In certain embodiments, $R^2$, $R^3$, and $R^5$ are hydrogen, and $R^1$ and $R^4$ are methyl.

In certain embodiments, $R^6$ is hydrogen, halo, cyano, nitro, or guanidine. In certain embodiments, $R^6$ is hydrogen. In certain embodiments, $R^6$ is halo. In certain embodiments, $R^6$ is fluoro or chloro. In certain embodiments, $R^6$ is cyano. In certain embodiments, $R^6$ is nitro. In certain embodiments, $R^6$ is $C_{1-6}$ alkyl, optionally substituted as described herein. In certain embodiments, $R^6$ is $C_{1-6}$ alkyl, optionally substituted with one, two, or three halo. In certain embodiments, $R^6$ is methyl, ethyl, propyl (e.g., n-propyl and isopropyl), butyl (e.g., n-butyl, 2-butyl, isobutyl, or t-butyl), or pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, $R^6$ is methyl. In certain embodiments, $R^6$ is $C_{1-6}$ alkoxy, optionally substituted as described herein. In certain embodiments, $R^6$ is $C_{1-6}$ alkoxy, optionally substituted with one, two, or three halo. In certain embodiments, $R^6$ is $C_{2-6}$ alkylthio, optionally substituted as described herein. In certain embodiments, $R^6$ is $C_{1-6}$ alkylthio, optionally substituted with one, two, or three halo. In certain embodiments, $R^6$ is $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted as described herein. In certain embodiments, $R^6$ is —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —N$R^{1a}C(O)R^{1d}$, —N$R^{1a}C(O)OR^{1d}$, —N$R^{1a}C(O)NR^{1b}R^{1c}$, —N$R^{1a}C(=NR^{1d})NR^{1b}R^{1c}$, —N$R^{1a}S(O)R^{1d}$, —N$R^{1a}S(O)_2R^{1d}$, —N$R^{1a}S(O)NR^{1b}R^{1c}$, —N$R^{1a}S(O)_2NR^{1b}R^{1c}$, —S$R^{1a}$, —S(O)$R^{1a}$, —S(O)$_2R^{1a}$, —S(O)N$R^{1b}R^{1c}$, or —S(O)$_2NR^{1b}R^{1c}$; wherein $R^{1a}$, $R^{1b}$, $R^{1c}$, and $R^{1d}$ are each as defined herein.

In certain embodiments, $R^7$ is halo, cyano, nitro, oxo, or guanidine. In certain embodiments, $R^7$ is halo. In certain embodiments, $R^7$ is fluoro or chloro. In certain embodiments, $R^7$ is cyano. In certain embodiments, $R^7$ is nitro. In certain embodiments, $R^7$ is oxo. In certain embodiments, $R^7$ is $C_{1-6}$ alkyl, optionally substituted as described herein. In certain embodiments, $R^7$ is $C_{1-6}$ alkyl, optionally substituted with one, two, or three halo. In certain embodiments, $R^7$ is methyl, ethyl, propyl (e.g., n-propyl and isopropyl), butyl (e.g., n-butyl, 2-butyl, isobutyl, or t-butyl), or pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, $R^7$ is methyl. In certain embodiments, $R^7$ is $C_{1-6}$ alkoxy, optionally substituted as described herein. In certain embodiments, $R^7$ is $C_{1-6}$ alkoxy, optionally substituted with one, two, or three halo. In certain embodiments, $R^7$ is $C_{2-6}$ alkylthio, optionally substituted as described herein. In certain embodiments, $R^7$ is $C_{1-6}$ alkylthio, optionally substituted with one, two, or three halo. In certain embodiments, $R^7$ is $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted as described herein. In certain embodiments, $R^7$ is —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2NR^{1b}R^{1c}$, —N$R^{1b}R^{1c}$, —N$R^{1a}C(O)R^{1d}$, —N$R^{1a}C(O)OR^{1d}$, —N$R^{1a}C(O)NR^{1b}R^{1c}$, —N$R^{1a}C(=NR^{1d})NR^{1b}R^{1c}$, —N$R^{1a}S(O)R^{1d}$, —N$R^{1a}S(O)_2R^{1d}$, —N$R^{1a}S(O)NR^{1b}R^{1c}$, —N$R^{1a}S(O)_2NR^{1b}R^{1c}$, —S$R^{1a}$, —S(O)$R^{1a}$, —S(O)$_2R^{1a}$, —S(O)NR$^{1b}R^{1c}$, or —S(O)$_2NR^{1b}R^{1c}$; wherein $R^{1a}$, $R^{1b}$, $R^{1c}$, and $R^{1d}$ are each as defined herein.

In certain embodiments, X is O. In certain embodiments, X is S.

In certain embodiments, $R^{Ya}$ is —C(O)$R^{1a}$, wherein $R^{1a}$ is as defined herein. In certain embodiments, $R^{Ya}$ is not —C(O)H. In certain embodiments, $R^{Ya}$ is —C(O)O$R^{1a}$, wherein $R^{1a}$ is as defined herein. In certain embodiments, $R^{Ya}$ is —C(O)O$R^{1a}$, wherein $R^{1a}$ is as defined herein, with the proviso that $R^{1a}$ is not -t-butyl, 9-fluorenylmethyl, or benzyl. In certain embodiments, $R^{Ya}$ is —C(O)O-ethyl. In certain embodiments, $R^{Ya}$ is —C(O)N$R^{1b}R^{1c}$, wherein $R^{1b}$ and $R^{1c}$ are each as defined herein. In certain embodiments, $R^{Ya}$ is —C(S)N$R^{1b}R^{1c}$, wherein $R^{1b}$ and $R^{1c}$ are each as defined herein. In certain embodiments, $R^{Ya}$ is —C(S)N$R^{1a}C(O)NR^{1b}R^{1c}$, wherein $R^{1a}$, $R^{1b}$, and $R^{1c}$ are each as defined herein. In certain embodiments, $R^{Ya}$ is —C(N$R^{1a}$)N$R^{1b}R^{1c}$, wherein $R^{1a}$, $R^{1b}$, and $R^{1c}$ are each as defined herein. In certain embodiments, $R^{Ya}$ is —C(NNO$_2$)N$R^{1b}R^{1c}$, wherein $R^{1b}$ and $R^{1c}$ are each as defined herein. In certain embodiments, $R^{Ya}$ is —S(O)$R^{1a}$, wherein $R^{1a}$ is as defined herein. In certain embodiments, $R^{Ya}$ is —S(O)$_2R^{1a}$, wherein $R^{1a}$ is as defined herein. In certain embodiments, $R^{Ya}$ is —S(O)N$R^{1b}R^{1c}$, wherein $R^{1b}$ and $R^{1c}$ are each as defined herein. In certain embodiments, $R^{Ya}$ is —S(O)$_2NR^{1b}R^{1c}$, wherein $R^{1a}$ and $R^{1d}$ are each as defined herein.

In certain embodiments, m is 0. In certain embodiments, m is 1. In certain embodiments, m is 2. In certain embodiments, m is 3.

In certain embodiments, n is 1. In certain embodiments, n is 2. In certain embodiments, n is 3.

In certain embodiments, m is 1 and n is 1. In certain embodiments, m is 1 and n is 2.

In certain embodiments, p is 0. In certain embodiments, p is 1. In certain embodiments, p is 2. In certain embodiments, p is 3. In certain embodiments, p is 4.

In certain embodiments, $R^{1a}$ is hydrogen. In certain embodiments, $R^{1a}$ is $C_{1-6}$ alkyl, optionally substituted as described herein. In certain embodiments, $R^{1a}$ is $C_{1-6}$ alkyl, optionally substituted with one, two, or three substituents, each of which is independently selected from cyano, halo, $C_{3-7}$ cycloalkyl, $C_{6-14}$ aryl, heteroaryl, heterocyclyl, —C(O)$R^a$, —C(O)O$R^a$, and —S$R^a$, where the cycloalkyl, aryl, heteroaryl, and heterocyclyl are each further optionally substituted with one, two, or three substituents, each of which is independently halo or $C_{1-6}$ alkyl. In certain embodiments, $R^{1a}$ is $C_{1-6}$ alkyl, optionally substituted with one or two substituents, each of which is independently selected from halo, cyano, nitro, $C_{1-6}$ alkyl, $C_{3-7}$ cycloalkyl, $C_{6-14}$ aryl, heteroaryl, heterocyclyl, —O$R^a$, —S$R^a$, and —C(O)$R^a$, where $R^a$ is as defined herein and the alkyl, cycloalkyl, aryl, heteroaryl, and heterocyclyl are each optionally further substituted with one or two substituents, each of which is independently halo or $C_{1-6}$ alkyl. In certain embodiments, $R^{1a}$ is $C_{1-6}$ alkyl, optionally substituted with one or two substituents, each of which is independently selected from fluoro, chloro, cyano, nitro, methyl, trifluoromethyl, ethyl, methoxy, ethoxy, methylthio, (1S,2S,4R)-7,7-dimethylbicyclo[2.2.1]-heptyl, phenyl, chlorophenyl, furanyl, morpholinyl, acetyl, propionyl, and ethoxycarbonyl. In certain embodiments, $R^{1a}$ is $C_{1-6}$ alkyl, optionally substituted with one substituent selected from chloro, cyano, ethoxy, methylthio, (1S,2S,4R)-7,7-dimethylbicyclo[2.2.1]-heptyl, phenyl, chlorophenyl, furanyl, morpholinyl, propionyl, and ethoxycarbonyl. In certain embodiments, $R^{1a}$ is methyl, ethyl, propyl (e.g., n-propyl or isopropyl), butyl (e.g., n-butyl, 2-butyl, isobutyl, or t-butyl), or pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, $R^{1a}$ is methyl, ethyl, isopropyl, isobutyl, t-butyl, 1,1-dimethylpropyl, or 2,2-dimethylpropyl. In certain embodiments, $R^{1a}$ is $C_{1-6}$ alkyl, methyl, ethyl, propyl (e.g., n-propyl or isopropyl), butyl (e.g., n-butyl, 2-butyl, isobutyl, or t-butyl), or pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl), each optionally substituted with a substituent selected from chloro, cyano, ethoxy, methylthio, (1S,2S,4R)-7,7-dimethylbicyclo[2.2.1]-heptyl, phenyl, chlorophenyl, furanyl, morpholinyl, propionyl, and ethoxycarbonyl. In certain embodiments, $R^{1a}$ is methyl, ethyl, propyl (e.g., n-propyl or isopropyl), butyl (e.g., n-butyl, 2-butyl, isobutyl, or t-butyl), pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl), chloroethyl, chloropropyl, chlorobutyl, ethoxycarbonylethyl, methylthiopropyl, cyanomethyl, (1S,2S,4R)-7,7-dimethylbicyclo[2.2.1]-heptylmethyl, benzyl, chlorobenzyl, furanylemthyl, morpholinylethyl, or propionylethyl. In certain embodiments, $R^{1a}$ is methyl, ethyl, isopropyl, isobutyl, t-butyl, 1,1-dimethylpropyl, 2,2-dimethylpropyl, 2-chloroethyl, 3-chloropropyl, 4-chlorobutyl, 2-ethoxycarbonylethyl, 3-methylthiopropyl, 1-cyanomethyl, (1S,2S,4R)-7,7-dimethylbicyclo[2.2.1]-heptylmethyl, benzyl, 3-chlorobenzyl, furan-2-ylemthyl, 2-morpholin-4-yl-ethyl, or 2-propionylethyl.

In certain embodiments, $R^{1a}$ is $C_{2-6}$ alkenyl, optionally substituted as described herein. In certain embodiments, $R^{1a}$ is $C_{1-6}$ alkenyl, optionally substituted with $C_{6-14}$ aryl. In certain embodiments, $R^{1a}$ is $C_{2-6}$ alkenyl, optionally substituted with one or two substituents, each of which is independently selected from halo, cyano, nitro, $C_{1-6}$ alkyl, $C_{3-7}$ cycloalkyl, $C_{6-14}$ aryl, heteroaryl, heterocyclyl, —$OR^a$, —$SR^a$, and —$C(O)R^a$, where $R^a$ is as defined herein and the alkyl, cycloalkyl, aryl, heteroaryl, and heterocyclyl are each optionally further substituted with one or two substituents, each of which is independently halo or $C_{1-6}$ alkyl. In certain embodiments, $R^{1a}$ is $C_{2-6}$ alkenyl, optionally substituted with one or two substituents, each of which is independently selected from fluoro, chloro, cyano, nitro, methyl, trifluoromethyl, ethyl, methoxy, ethoxy, methylthio, (1S,2S,4R)-7,7-dimethylbicyclo[2.2.1]-heptyl, phenyl, chlorophenyl, furanyl, morpholinyl, acetyl, propionyl, and ethoxycarbonyl. In certain embodiments, $R^{1a}$ is $C_{2-6}$ alkenyl, optionally substituted with $C_{6-14}$ aryl. In certain embodiments, $R^{1a}$ is $C_{2-6}$ alkenyl, optionally substituted with phenyl. In certain embodiments, $R^{1a}$ is ethenyl or allyl, each optionally substituted with phenyl. In certain embodiments, $R^{1a}$ is ethenyl, allyl, or phenylethenyl. In certain embodiments, $R^{1a}$ is ethenyl, allyl, or 2-phenylethenyl.

In certain embodiments, $R^{1a}$ is $C_{2-6}$ alkynyl, optionally substituted as described herein. In certain embodiments, $R^{1a}$ is $C_{3-7}$ cycloalkyl, optionally substituted as described herein. In certain embodiments, $R^{1a}$ is $C_{3-7}$ cycloalkyl, optionally substituted with one or two $C_{1-6}$ alkyl. In certain embodiments, $R^{1a}$ is $C_{3-7}$ cycloalkyl, optionally substituted with one or two substituents, each of which is independently selected from halo, cyano, nitro, $C_{1-6}$ alkyl, $C_{3-7}$ cycloalkyl, $C_{6-14}$ aryl, heteroaryl, heterocyclyl, —$OR^a$, —$SR^a$, and —$C(O)R^a$, where $R^a$ is as defined herein and the alkyl, cycloalkyl, aryl, heteroaryl, and heterocyclyl are each optionally further substituted with one or two substituents, each of which is independently halo or $C_{1-6}$ alkyl. In certain embodiments, $R^{1a}$ is $C_{3-7}$ cycloalkyl, optionally substituted with one or two substituents, each of which is independently selected from fluoro, chloro, cyano, nitro, methyl, trifluoromethyl, ethyl, methoxy, ethoxy, methylthio, (1S,2S,4R)-7,7-dimethylbicyclo[2.2.1]-heptyl, phenyl, chlorophenyl, furanyl, morpholinyl, acetyl, propionyl, and ethoxycarbonyl. In certain embodiments, $R^{1a}$ is $C_{3-7}$ cycloalkyl, optionally substituted with one or two $C_{1-6}$ alkyl. In certain embodiments, $R^{1a}$ is $C_{3-7}$ cycloalkyl, optionally substituted with two methyl groups. In certain embodiments, $R^{1a}$ is cyclobutyl, cyclopentyl, cyclohexyl, or dimethylbicyclo-[2.2.1]heptyl (e.g., 7,7-dimethylbicyclo[2.2.1]-heptyl). In certain embodiments, $R^{1a}$ is cyclobutyl, cyclopentyl, or cyclohexyl. In certain embodiments, $R^{1a}$ is cyclobutyl, cyclopentyl, cyclohexyl, or (1S,2S,4R)-7,7-dimethylbicyclo[2.2.1]-heptyl.

In certain embodiments, $R^{1a}$ is $C_{6-14}$ aryl, optionally substituted as described herein. In certain embodiments, $R^{1a}$ is $C_{6-14}$ aryl, optionally substituted with one, two, or three substituents, each of which is independently selected from halo, nitro, cyano, —$OR^a$, —$C(O)R^a$, and $C_{1-6}$ alkyl, where the alkyl is further optionally substituted with one, two, or three halo. In certain embodiments, $R^{1a}$ is $C_{6-14}$ aryl, optionally substituted with one or two substituents, each of which is independently selected from halo, cyano, nitro, $C_{1-6}$ alkyl, $C_{3-7}$ cycloalkyl, $C_{6-14}$ aryl, heteroaryl, heterocyclyl, —$OR^a$, —$SR^a$, and —$C(O)R^a$, where $R^a$ is as defined herein and the alkyl, cycloalkyl, aryl, heteroaryl, and heterocyclyl are each optionally further substituted with one or two substituents, each of which is independently halo or $C_{1-6}$ alkyl. In certain embodiments, $R^{1a}$ is $C_{6-14}$ aryl, optionally substituted with one or two substituents, each of which is independently selected from fluoro, chloro, cyano, nitro, methyl, trifluoromethyl, ethyl, methoxy, ethoxy, methylthio, (1S,2S,4R)-7,7-dimethylbicyclo[2.2.1]-heptyl, phenyl, chlorophenyl, furanyl, morpholinyl, acetyl, propionyl, and ethoxycarbonyl. In certain embodiments, $R^{1a}$ is $C_{6-14}$ aryl, optionally substituted with one or two substituents, each independently selected from fluoro, chloro, cyano, nitro, methyl, trifluoromethyl, ethyl, methoxy, and acetyl. In certain embodiments, $R^{1a}$ is phenyl, optionally substituted with one or two substituents, each independently selected from fluoro, chloro, cyano, nitro, methyl, trifluoromethyl, ethyl, methoxy, and acetyl. In certain embodiments, $R^{1a}$ is $C_{6-14}$ aryl, optionally substituted with one or more halo or $C_{1-6}$ alkyl, wherein the alkyl is optionally substituted with one, two, or three halo. In certain embodiments, $R^{1a}$ is $C_{6-14}$ aryl, optionally substituted with fluoro, chloro, methyl, trifluoromethyl, or ethyl. In certain embodiments, $R^{1a}$ is phenyl, fluorophenyl (e.g., 2-fluorophenyl, 3-fluorophenyl, or 4-fluorophenyl), chlorophenyl (e.g., 2-chlorophenyl, 3-chlorophenyl, or 4-chlorophenyl), methylphenyl (e.g., 2-methylphenyl, 3-methylphenyl, or 4-methylphenyl), trifluoromethylphenyl (e.g., 2-trifluoromethylphenyl, 3-trifluoromethylphenyl, or 4-trifluoromethylphenyl), or ethylphenyl (e.g., 2-ethylphenyl, 3-ethylphenyl, or 4-ethylphenyl). In certain embodiments, $R^{1a}$ is phenyl, 3-fluorophenyl, 3-methylphenyl, 4-chlorophenyl, 4-methylphenyl, 4-trifluoromethylphenyl, or 4-ethylphenyl. In certain embodiments, $R^{1a}$ is phenyl, chlorophenyl (e.g., 2-chlorophenyl, 3-chlorophenyl, or 4-chlorophenyl), fluorophenyl (e.g., 2-fluorophenyl, 3-fluorophenyl, or 4-fluorophenyl), cyanophenyl (e.g., 2-cyanophenyl, 3-cyanophenyl, or 4-cyanophenyl), nitrophenyl (e.g., 2-nitrophenyl, 3-nitrophenyl, or 4-nitrophenyl), methylphenyl (e.g., 2-methylphenyl, 3-methylphenyl, or 4-methylphenyl), trifluoromethylphenyl (e.g., 2-trifluoromethylphenyl, 3-trifluoromethylphenyl, or 4-trifluoromethylphenyl), ethylphenyl (e.g., 2-ethylphenyl, 3-ethylphenyl, or 4-ethylphenyl), methoxyphenyl (e.g., 2-methoxyphenyl, 3-methoxyphenyl, or 4-methoxyphenyl), acetylphenyl (e.g., 2-acetylphenyl, 3-acetylphenyl, or 4-acetylphenyl), dichlorophenyl (e.g., 2,3-dichlorophenyl, 2,4-dichlorophenyl, 2,5-dichlorophenyl, 2,6-dichlorophenyl, 3,4-dichlorophenyl, or 3,5-dichlorophenyl). In certain embodiments, $R^{1a}$ is phenyl, 2-chlorophenyl, 3-chlorophenyl, 4-chlorophenyl, 2-fluorophenyl, 3-fluorophenyl, 4-fluorophenyl, 4-cyanophenyl, 4-nitrophenyl, 2-methylphenyl, 3-methylphenyl, 4-methylphenyl, 4-trifluoromethylphenyl, 4-ethylphenyl, 4-methoxyphenyl, 3-acetylphenyl, or 3,4-dichlorophenyl.

In certain embodiments, $R^{1a}$ is heteroaryl, optionally substituted as described herein. In certain embodiments, $R^{1a}$ is heteroaryl, optionally substituted with one, two, or three substituents, each of which is independently halo or $C_{1-6}$ alkyl. In certain embodiments, $R^{1a}$ is heteroaryl, optionally substituted with one or two substituents, each of which is independently selected from halo, cyano, nitro, $C_{1-6}$ alkyl, $C_{3-7}$ cycloalkyl, $C_{6-14}$ aryl, heteroaryl, heterocyclyl, $-OR^a$, $-SR^a$, and $-C(O)R^a$, where $R^a$ is as defined herein and the alkyl, cycloalkyl, aryl, heteroaryl, and heterocyclyl are each optionally further substituted with one or two substituents, each of which is independently halo or $C_{1-6}$ alkyl. In certain embodiments, $R^{1a}$ is heteroaryl, optionally substituted with one or two substituents, each of which is independently selected from fluoro, chloro, cyano, nitro, methyl, trifluoromethyl, ethyl, methoxy, ethoxy, methylthio, (1S,2S,4R)-7,7-dimethylbicyclo[2.2.1]-heptyl, phenyl, chlorophenyl, furanyl, morpholinyl, acetyl, propionyl, and ethoxycarbonyl. In certain embodiments, $R^{1a}$ is heteroaryl, optionally substituted with one or two methyl. In certain embodiments, $R^{1a}$ is furanyl, thienyl, isoxazolyl, pyrazolyl, 1,2,3-thiadiazolyl, pyridinyl, pyrazyl, benzofuranyl, benzo[c][1,2,5]oxadiazolyl, benzothienyl, or benzothiazolyl, each optionally substituted with one or two methyl. In certain embodiments, $R^{1a}$ is furanyl (e.g., furan-2-yl or furan-3-yl), thienyl (e.g., thien-2-yl or thien-3-yl), methyl-thienyl, isoxazolyl, dimethylpyrazolyl, methyl-1,2,3-thiadiazolyl, pyridinyl (e.g., pyridin-2-yl, pyridin-3-yl, or pyridin-4-yl), pyrazyl (e.g., 2-pyrazyl or 3-pyrazyl), benzofuranyl, benzo[c][1,2,5]oxadiazolyl, benzothienyl, or benzothiazolyl. In certain embodiments, $R^{1a}$ is furan-2-yl, thien-2-yl, 3-methyl-thien-2-yl, isoxazol-5-yl, 2,5-dimethylpyrazol-3-yl, 4-methyl-1,2,3-thiadiazol-5-yl, pyridin-2-yl, 2-pyrazyl, benzofuran-2-yl, benzo[c][1,2,5]oxadiazol-5-yl, benzothien-2-yl, or benzothiazol-2-yl.

In certain embodiments, $R^{1a}$ is heterocyclyl. In certain embodiments, $R^{1a}$ is heterocyclyl, optionally substituted with one or two substituents, each of which is independently selected from halo, cyano, nitro, $C_{1-6}$ alkyl, $C_{3-7}$ cycloalkyl, $C_{6-14}$ aryl, heteroaryl, heterocyclyl, $-OR^a$, $-SR^a$, and $-C(O)R^a$, where $R^a$ is as defined herein and the alkyl, cycloalkyl, aryl, heteroaryl, and heterocyclyl are each optionally further substituted with one or two substituents, each of which is independently halo or $C_{1-6}$ alkyl. In certain embodiments, $R^{1a}$ is heterocyclyl, optionally substituted with one or two substituents, each of which is independently selected from fluoro, chloro, cyano, nitro, methyl, trifluoromethyl, ethyl, methoxy, ethoxy, methylthio, (1S,2S,4R)-7,7-dimethylbicyclo[2.2.1]-heptyl, phenyl, chlorophenyl, furanyl, morpholinyl, acetyl, propionyl, and ethoxycarbonyl. In certain embodiments, $R^{1a}$ is morpholinyl. In certain embodiments, $R^{1a}$ is morpholin-4-yl In certain embodiments, $R^{1b}$ is hydrogen. In certain embodiments, $R^{1b}$ is $C_{1-6}$ alkyl, optionally substituted as described herein. In certain embodiments, $R^{1b}$ is methyl or ethyl. In certain embodiments, $R^{1b}$ is $C_{2-6}$ alkenyl, optionally substituted as described herein. In certain embodiments, $R^{1b}$ is $C_{2-6}$ alkynyl, optionally substituted as described herein. In certain embodiments, $R^{1b}$ is $C_{3-7}$ cycloalkyl, optionally substituted as described herein. In certain embodiments, $R^{1b}$ is $C_{6-14}$ aryl, optionally substituted as described herein. In certain embodiments, $R^{1b}$ is heteroaryl, optionally substituted as described herein. In certain embodiments, $R^{1b}$ is heterocyclyl, optionally substituted as described herein.

In certain embodiments, $R^{1c}$ is hydrogen. In certain embodiments, $R^{1c}$ is $C_{1-6}$ alkyl, optionally substituted as described herein. In certain embodiments, $R^{1c}$ is $C_{1-6}$ alkyl, optionally substituted with one, two, or three substituents, each of which is independently selected from cyano, halo, $C_{3-7}$ cycloalkyl, $C_{6-14}$ aryl, heteroaryl, heterocyclyl, $-C(O)R^a$, $-C(O)OR^a$, and $-SR^a$, where the cycloalkyl, aryl, heteroaryl, and heterocyclyl are each further optionally substituted with one, two, or three substituents, each of which is independently halo or $C_{1-6}$ alkyl. In certain embodiments, $R^{1c}$ is $C_{1-6}$ alkyl, optionally substituted with one or two substituents, each of which is independently selected from halo, cyano, nitro, $C_{1-6}$ alkyl, $C_{3-7}$ cycloalkyl, $C_{6-14}$ aryl, heteroaryl, heterocyclyl, $-OR^a$, $-SR^a$, and $-C(O)R^a$, where $R^a$ is as defined herein and the alkyl, cycloalkyl, aryl, heteroaryl, and heterocyclyl are each optionally further substituted with one or two substituents, each of which is independently halo or $C_{1-6}$ alkyl. In certain embodiments, $R^{1c}$ is $C_{1-6}$ alkyl, optionally substituted with one or two substituents, each of which is independently selected from fluoro, chloro, cyano, nitro, methyl, trifluoromethyl, ethyl, methoxy, ethoxy, methylthio, (1S,2S,4R)-7,7-dimethylbicyclo[2.2.1]-heptyl, phenyl, chlorophenyl, furanyl, morpholinyl, acetyl, propionyl, and ethoxycarbonyl. In certain embodiments, $R^{1c}$ is $C_{1-6}$ alkyl, optionally substituted with one substituent selected from chloro, cyano, ethoxy, methylthio, (1S,2S,4R)-7,7-dimethylbicyclo[2.2.1]-heptyl, phenyl, chlorophenyl, furanyl, morpholinyl, propionyl, and ethoxycarbonyl. In certain embodiments, $R^{1c}$ is methyl, ethyl, propyl (e.g., n-propyl or isopropyl), butyl (e.g., n-butyl, 2-butyl, isobutyl, or t-butyl), or pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, $R^{1c}$ is methyl, ethyl, isopropyl, isobutyl, t-butyl, 1,1-dimethylpropyl, or 2,2-dimethylpropyl. In certain embodiments, $R^{1c}$ is $C_{1-6}$ alkyl, methyl, ethyl, propyl (e.g., n-propyl or isopropyl), butyl (e.g., n-butyl, 2-butyl, isobutyl, or t-butyl), or pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl), each optionally substituted with a substituent selected from chloro, cyano, ethoxy, methylthio, (1S,2S,4R)-7,7-dimethylbicyclo[2.2.1]-heptyl, phenyl, chlorophenyl, furanyl, morpholinyl, propionyl, and ethoxycarbonyl. In certain embodiments, $R^{1c}$ is methyl, ethyl, propyl (e.g., n-propyl or isopropyl), butyl (e.g., n-butyl, 2-butyl, isobutyl, or t-butyl), pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl), chloroethyl, chloropropyl, chlorobutyl, ethoxycarbonylethyl, methylthiopropyl, cyanomethyl, (1S,2S,4R)-7,7-dimethylbicyclo[2.2.1]-heptylmethyl, benzyl, chlorobenzyl, furanylemthyl, morpholinylethyl, or propionylethyl. In certain embodiments, $R^{1c}$ is methyl, ethyl, isopropyl, isobutyl, t-butyl, 1,1-dimethylpropyl, 2,2-dimethylpropyl, 2-chloroethyl, 3-chloropropyl, 4-chlorobutyl, 2-ethoxycarbonylethyl, 3-methylthiopropyl, 1-cyanomethyl, (1S,2S,4R)-7,7-dimethylbicyclo[2.2.1]-heptylmethyl, benzyl, 3-chlorobenzyl, furan-2-ylmethyl, 2-morpholin-4-ylethyl, or 2-propionylethyl.

In certain embodiments, $R^{1c}$ is $C_{2-6}$ alkenyl, optionally substituted as described herein. In certain embodiments, $R^{1c}$ is $C_{1-6}$ alkenyl, optionally substituted with $C_{6-14}$ aryl. In certain embodiments, $R^{1c}$ is $C_{2-6}$ alkenyl, optionally substituted with one or two substituents, each of which is independently selected from halo, cyano, nitro, $C_{1-6}$ alkyl, $C_{3-7}$ cycloalkyl, $C_{6-14}$ aryl, heteroaryl, heterocyclyl, —$OR^a$, —$SR^a$, and —$C(O)R^a$, where $R^a$ is as defined herein and the alkyl, cycloalkyl, aryl, heteroaryl, and heterocyclyl are each optionally further substituted with one or two substituents, each of which is independently halo or $C_{1-6}$ alkyl. In certain embodiments, $R^{1c}$ is $C_{2-6}$ alkenyl, optionally substituted with one or two substituents, each of which is independently selected from fluoro, chloro, cyano, nitro, methyl, trifluoromethyl, ethyl, methoxy, ethoxy, methylthio, (1S,2S,4R)-7,7-dimethylbicyclo[2.2.1]-heptyl, phenyl, chlorophenyl, furanyl, morpholinyl, acetyl, propionyl, and ethoxycarbonyl. In certain embodiments, $R^{1c}$ is $C_{2-6}$ alkenyl, optionally substituted with $C_{6-14}$ aryl. In certain embodiments, $R^{1c}$ is $C_{2-6}$ alkenyl, optionally substituted with phenyl. In certain embodiments, $R^{1c}$ is ethenyl or allyl, each optionally substituted with phenyl. In certain embodiments, $R^{1c}$ is ethenyl, allyl, or phenylethenyl. In certain embodiments, $R^{1c}$ is ethenyl, allyl, or 2-phenylethenyl.

In certain embodiments, $R^{1c}$ is $C_{2-6}$ alkynyl, optionally substituted as described herein. In certain embodiments, $R^{1c}$ is $C_{3-7}$ cycloalkyl, optionally substituted as described herein. In certain embodiments, $R^{1c}$ is $C_{3-7}$ cycloalkyl, optionally substituted with one or two $C_{1-6}$ alkyl. In certain embodiments, $R^{1c}$ is $C_{3-7}$ cycloalkyl, optionally substituted with one or two substituents, each of which is independently selected from halo, cyano, nitro, $C_{1-6}$ alkyl, $C_{3-7}$ cycloalkyl, $C_{6-14}$ aryl, heteroaryl, heterocyclyl, —$OR^a$, —$SR^a$, and —$C(O)R^a$, where $R^a$ is as defined herein and the alkyl, cycloalkyl, aryl, heteroaryl, and heterocyclyl are each optionally further substituted with one or two substituents, each of which is independently halo or $C_{1-6}$ alkyl. In certain embodiments, $R^{1c}$ is $C_{3-7}$ cycloalkyl, optionally substituted with one or two substituents, each of which is independently selected from fluoro, chloro, cyano, nitro, methyl, trifluoromethyl, ethyl, methoxy, ethoxy, methylthio, (1S,2S,4R)-7,7-dimethylbicyclo[2.2.1]-heptyl, phenyl, chlorophenyl, furanyl, morpholinyl, acetyl, propionyl, and ethoxycarbonyl. In certain embodiments, $R^{1c}$ is $C_{3-7}$ cycloalkyl, optionally substituted with one or two $C_{1-6}$ alkyl. In certain embodiments, $R^{1c}$ is $C_{3-7}$ cycloalkyl, optionally substituted with two methyl groups. In certain embodiments, $R^{1c}$ is cyclobutyl, cyclopentyl, cyclohexyl, or dimethylbicyclo-[2.2.1]heptyl (e.g., 7,7-dimethylbicyclo[2.2.1]-heptyl). In certain embodiments, $R^{1c}$ is cyclobutyl, cyclopentyl, or cyclohexyl. In certain embodiments, $R^{1c}$ is cyclobutyl, cyclopentyl, cyclohexyl, or (1S,2S,4R)-7,7-dimethylbicyclo[2.2.1]-heptyl.

In certain embodiments, $R^{1c}$ is $C_{6-14}$ aryl, optionally substituted as described herein. In certain embodiments, $R^{1c}$ is $C_{6-14}$ aryl, optionally substituted with one, two, or three substituents, each of which is independently selected from halo, nitro, cyano, —$OR^a$, —$C(O)R^a$, and $C_{1-6}$ alkyl, where the alkyl is further optionally substituted with one, two, or three halo. In certain embodiments, $R^{1c}$ is $C_{6-14}$ aryl, optionally substituted with one or two substituents, each of which is independently selected from halo, cyano, nitro, $C_{1-6}$ alkyl, $C_{3-7}$ cycloalkyl, $C_{6-14}$ aryl, heteroaryl, heterocyclyl, —$OR^a$, —$SR^a$, and —$C(O)R^a$, where $R^a$ is as defined herein and the alkyl, cycloalkyl, aryl, heteroaryl, and heterocyclyl are each optionally further substituted with one or two substituents, each of which is independently halo or $C_{1-6}$ alkyl. In certain embodiments, $R^{1c}$ is $C_{6-14}$ aryl, optionally substituted with one or two substituents, each of which is independently selected from fluoro, chloro, cyano, nitro, methyl, trifluoromethyl, ethyl, methoxy, ethoxy, methylthio, (1S,2S,4R)-7,7-dimethylbicyclo[2.2.1]-heptyl, phenyl, chlorophenyl, furanyl, morpholinyl, acetyl, propionyl, and ethoxycarbonyl. In certain embodiments, $R^{1c}$ is $C_{6-14}$ aryl, optionally substituted with one or two substituents, each independently selected from fluoro, chloro, cyano, nitro, methyl, trifluoromethyl, ethyl, methoxy, and acetyl. In certain embodiments, $R^{1c}$ is phenyl, optionally substituted with one or two substituents, each independently selected from fluoro, chloro, cyano, nitro, methyl, trifluoromethyl, ethyl, methoxy, and acetyl. In certain embodiments, $R^{1c}$ is $C_{6-14}$ aryl, optionally substituted with one or more halo or $C_{1-6}$ alkyl, wherein the alkyl is optionally substituted with one, two, or three halo. In certain embodiments, $R^{1c}$ is $C_{6-14}$ aryl, optionally substituted with fluoro, chloro, methyl, trifluoromethyl, or ethyl. In certain embodiments, $R^{1c}$ is phenyl, fluorophenyl (e.g., 2-fluorophenyl, 3-fluorophenyl, or 4-fluorophenyl), chlorophenyl (e.g., 2-chlorophenyl, 3-chlorophenyl, or 4-chlorophenyl), methylphenyl (e.g., 2-methylphenyl, 3-methylphenyl, or 4-methylphenyl), trifluoromethylphenyl (e.g., 2-trifluoromethylphenyl, 3-trifluoromethylphenyl, or 4-trifluoromethylphenyl), or ethylphenyl (e.g., 2-ethylphenyl, 3-ethylphenyl, or 4-ethylphenyl). In certain embodiments, $R^{1c}$ is phenyl, 3-fluorophenyl, 3-methylphenyl, 4-chlorophenyl, 4-methylphenyl, 4-trifluoromethylphenyl, or 4-ethylphenyl. In certain embodiments, $R^{1c}$ is phenyl, chlorophenyl (e.g., 2-chlorophenyl, 3-chlorophenyl, or 4-chlorophenyl), fluorophenyl (e.g., 2-fluorophenyl, 3-fluorophenyl, or 4-fluorophenyl), cyanophenyl (e.g., 2-cyanophenyl, 3-cyanophenyl, or 4-cyanophenyl), nitrophenyl (e.g., 2-nitrophenyl, 3-nitrophenyl, or 4-nitrophenyl), methylphenyl (e.g., 2-methylphenyl, 3-methylphenyl, or 4-methylphenyl), trifluoromethylphenyl (e.g., 2-trifluoromethylphenyl, 3-trifluoromethylphenyl, or 4-trifluoromethylphenyl), ethylphenyl (e.g., 2-ethylphenyl, 3-ethylphenyl, or 4-ethylphenyl), methoxyphenyl (e.g., 2-methoxyphenyl, 3-methoxyphenyl, or 4-methoxyphenyl), acetylphenyl (e.g., 2-acetylphenyl, 3-acetylphenyl, or 4-acetylphenyl), dichlorophenyl (e.g., 2,3-dichlorophenyl, 2,4-dichlorophenyl, 2,5-dichlorophenyl, 2,6-dichlorophenyl, 3,4-dichlorophenyl, or 3,5-dichlorophenyl). In certain embodiments, $R^{1c}$ is phenyl, 2-chlorophenyl, 3-chlorophenyl, 4-chlorophenyl, 2-fluorophenyl, 3-fluorophenyl, 4-fluorophenyl, 4-cyanophenyl, 4-nitrophenyl, 2-methylphenyl, 3-methylphenyl, 4-methylphenyl, 4-trifluoromethylphenyl, 4-ethylphenyl, 4-methoxyphenyl, 3-acetylphenyl, or 3,4-dichlorophenyl.

In certain embodiments, $R^{1c}$ is heteroaryl, optionally substituted as described herein. In certain embodiments, $R^{1c}$ is heteroaryl, optionally substituted with one, two, or three substituents, each of which is independently halo or $C_{1-6}$ alkyl. In certain embodiments, $R^{1c}$ is heteroaryl, optionally substituted with one or two substituents, each of which is independently selected from halo, cyano, nitro, $C_{1-6}$ alkyl, $C_{3-7}$ cycloalkyl, $C_{6-14}$ aryl, heteroaryl, heterocyclyl, —$OR^a$, —$SR^a$, and —$C(O)R^a$, where $R^a$ is as defined herein and the alkyl, cycloalkyl, aryl, heteroaryl, and heterocyclyl are each optionally further substituted with one or two substituents, each of which is independently halo or $C_{1-6}$ alkyl. In certain embodiments, $R^{1c}$ is heteroaryl, optionally substituted with one or two substituents, each of which is independently selected from fluoro, chloro, cyano, nitro, methyl, trifluoromethyl, ethyl, methoxy, ethoxy, methylthio, (1S,2S,4R)-7,7-dimethylbicyclo[2.2.1]-heptyl, phenyl, chlorophenyl, furanyl, morpholinyl, acetyl, propionyl, and ethoxycarbonyl. In certain embodiments, $R^{1c}$ is heteroaryl, optionally substituted with one or two methyl. In certain embodiments, $R^{1c}$ is furanyl, thienyl, isoxazolyl, pyrazolyl, 1,2,3-thiadiazolyl, pyridinyl, pyrazyl, benzofuranyl, benzo[c][1,2,5]oxadiazolyl, benzothienyl, or benzothiazolyl, each optionally substituted with one or two methyl. In certain embodiments, $R^{1c}$ is furanyl (e.g., furan-2-yl or furan-3-yl), thienyl (e.g., thien-2-yl or thien-3-yl), methyl-thienyl, isoxazolyl, dimethylpyrazolyl, methyl-1,2,3-thiadiazolyl, pyridinyl (e.g., pyridin-2-yl, pyridin-3-yl, or pyridin-4-yl), pyrazyl (e.g., 2-pyrazyl or 3-pyrazyl), benzofuranyl, benzo[c][1,2,5]oxadiazolyl, benzothienyl, or benzothiazolyl. In certain embodiments, $R^{1c}$ is furan-2-yl, thien-2-yl, 3-methyl-thien-2-yl, isoxazol-5-yl, 2,5-dimethylpyrazol-3-yl, 4-methyl-1,2,3-thiadiazol-5-yl, pyridin-2-yl, 2-pyrazyl, benzofuran-2-yl, benzo[c][1,2,5] oxadiazol-5-yl, benzothien-2-yl, or benzothiazol-2-yl.

In certain embodiments, $R^{1c}$ is heterocyclyl. In certain embodiments, $R^{1c}$ is heterocyclyl, optionally substituted with one or two substituents, each of which is independently selected from halo, cyano, nitro, $C_{1-6}$ alkyl, $C_{3-7}$ cycloalkyl, $C_{6-14}$ aryl, heteroaryl, heterocyclyl, —$OR^a$, —$SR^a$, and —$C(O)R^a$, where $R^a$ is as defined herein and the alkyl, cycloalkyl, aryl, heteroaryl, and heterocyclyl are each optionally further substituted with one or two substituents, each of which is independently halo or $C_{1-6}$ alkyl. In certain embodiments, $R^{1c}$ is heterocyclyl, optionally substituted with one or two substituents, each of which is independently selected from fluoro, chloro, cyano, nitro, methyl, trifluoromethyl, ethyl, methoxy, ethoxy, methylthio, (1S,2S,4R)-7,7-dimethylbicyclo[2.2.1]-heptyl, phenyl, chlorophenyl, furanyl, morpholinyl, acetyl, propionyl, and ethoxycarbonyl. In certain embodiments, $R^{1c}$ is morpholinyl. In certain embodiments, $R^{1c}$ is morpholin-4-yl In certain embodiments, $R^{1b}$ and $R^{1c}$ together with the N atom to which they are attached independently form heteroaryl, optionally substituted as described herein. In certain embodiments, $R^{1b}$ and $R^{1c}$ together with the N atom to which they are attached independently form heterocyclyl, optionally substituted as described herein.

In certain embodiments, $R^{1d}$ is hydrogen. In certain embodiments, $R^{1d}$ is $C_{1-6}$ alkyl, optionally substituted as described herein. In certain embodiments, $R^{1d}$ is $C_{2-6}$ alkenyl, optionally substituted as described herein. In certain embodiments, $R^{1d}$ is $C_{2-6}$ alkynyl, optionally substituted as described herein. In certain embodiments, $R^{1d}$ is $C_{3-7}$ cycloalkyl, optionally substituted as described herein. In certain embodiments, $R^{1d}$ is $C_{6-14}$ aryl, optionally substituted as described herein. In certain embodiments, $R^{1d}$ is heteroaryl, optionally substituted as described herein. In certain embodiments, $R^{1d}$ is heterocyclyl, optionally substituted as described herein.

In one embodiment, provided herein is a compound selected from the group consisting of:

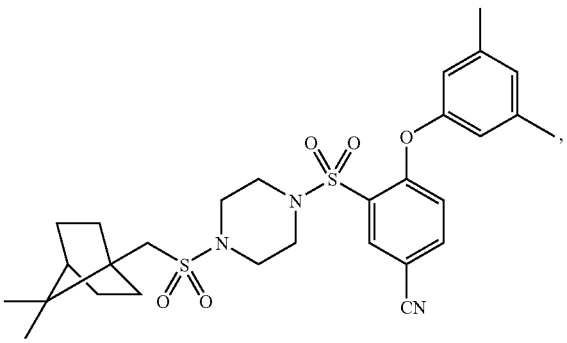

51

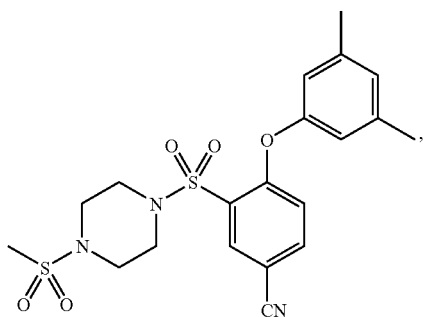

52

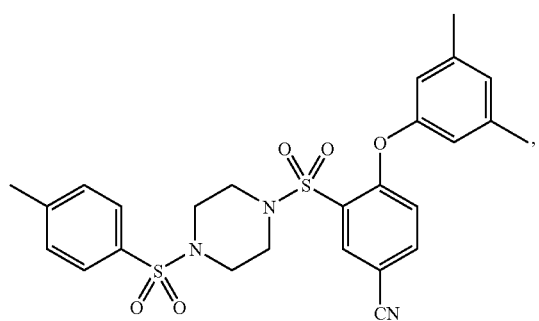

53

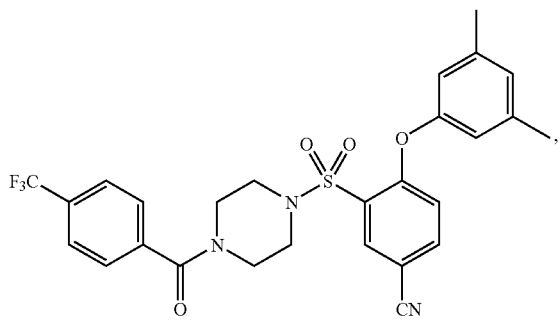

54

55 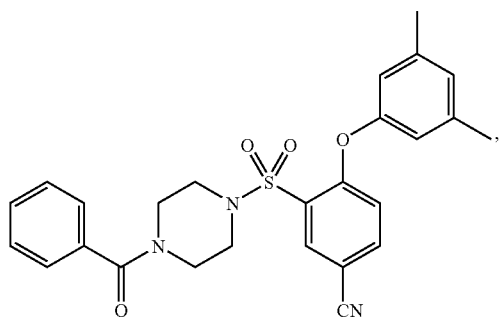
56 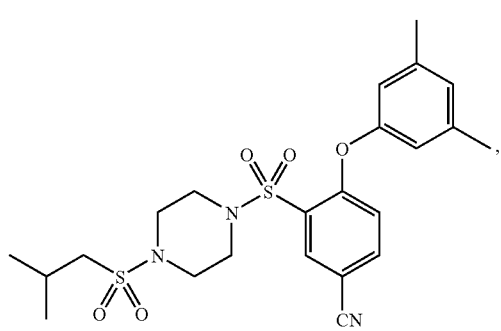
57 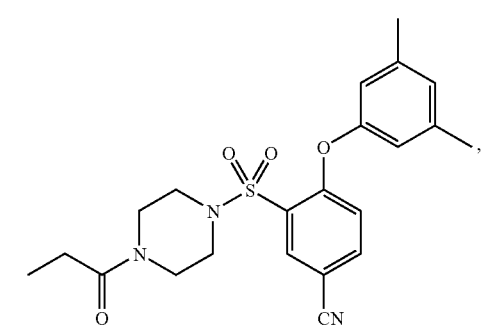
58 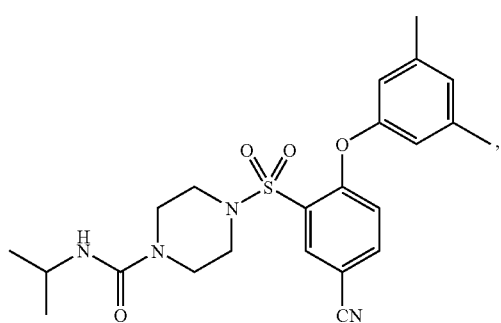
59 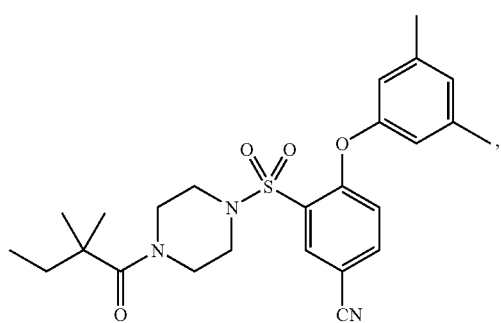
60 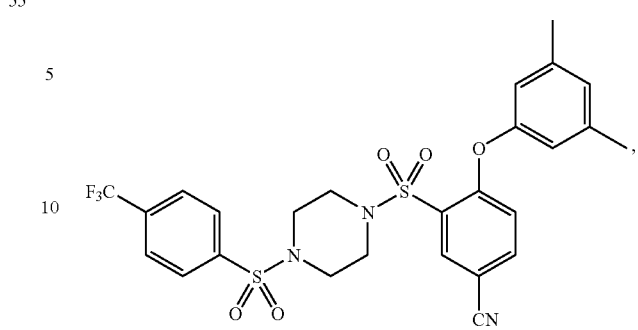
61 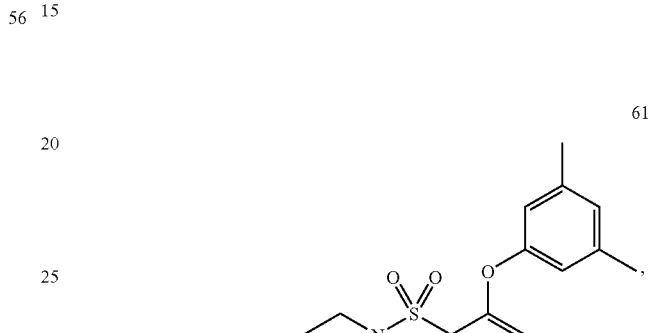
62 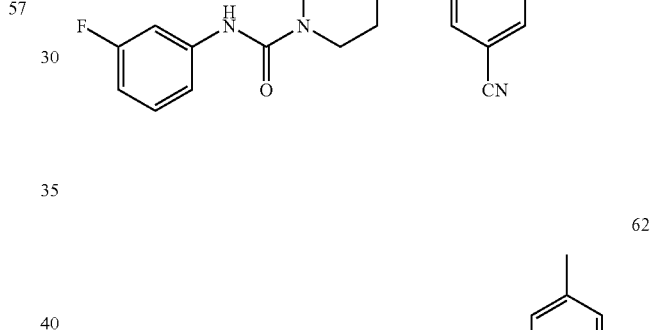
63 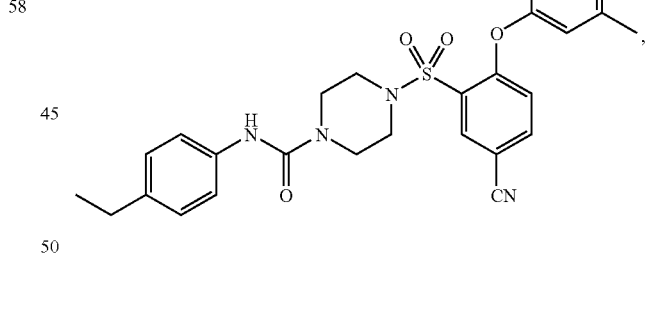
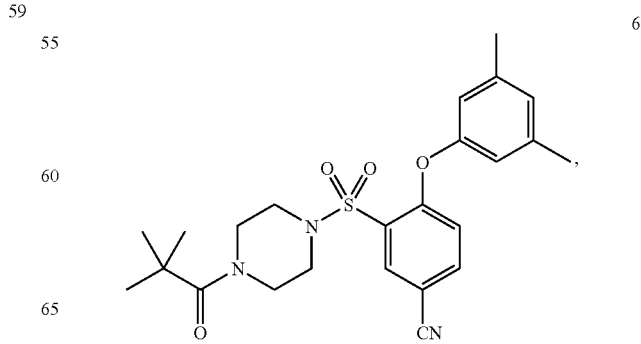

64
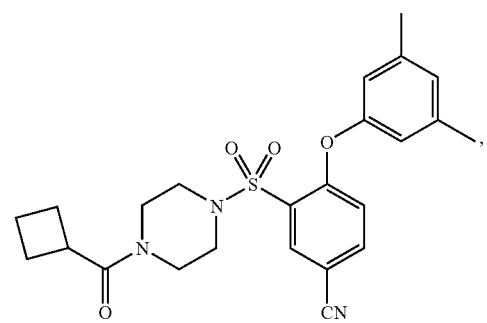
65
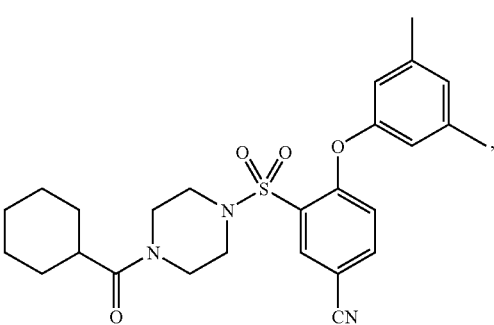
66
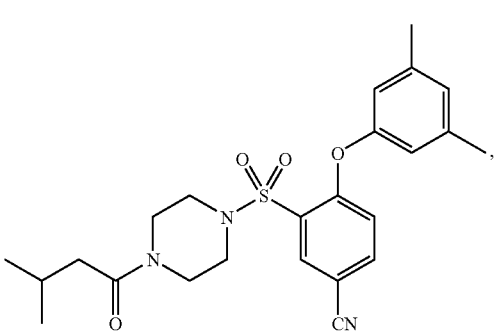
67
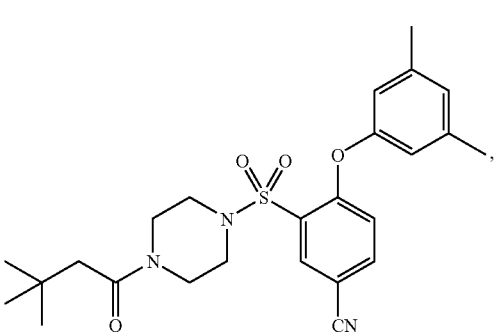
68
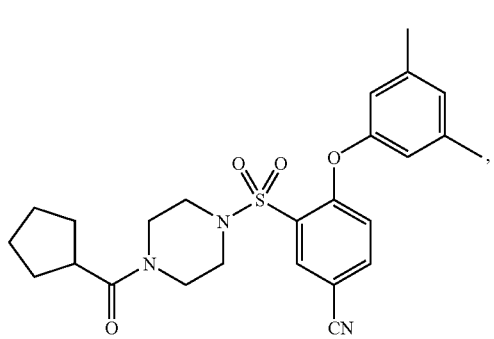
69
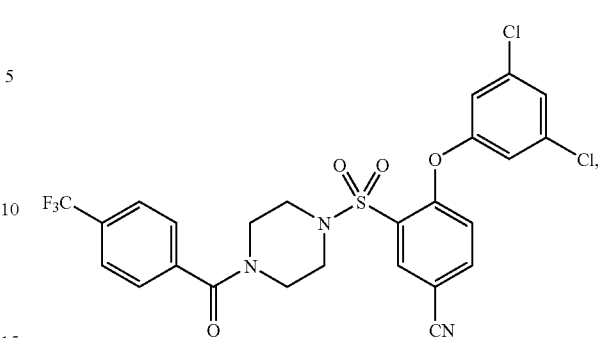
70
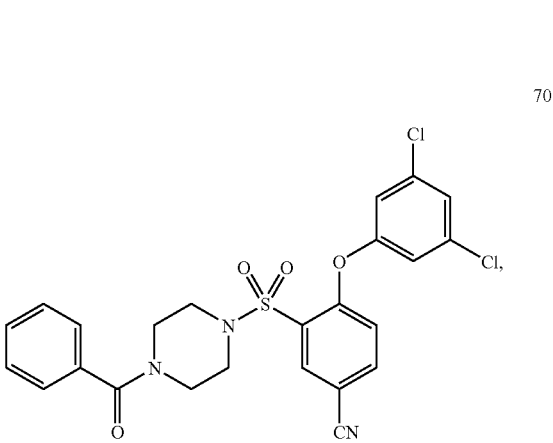
71
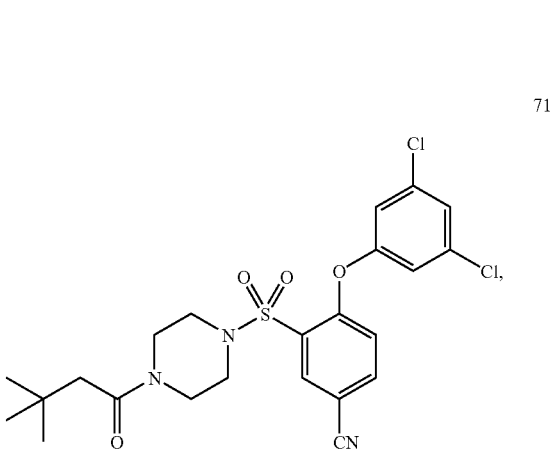
72
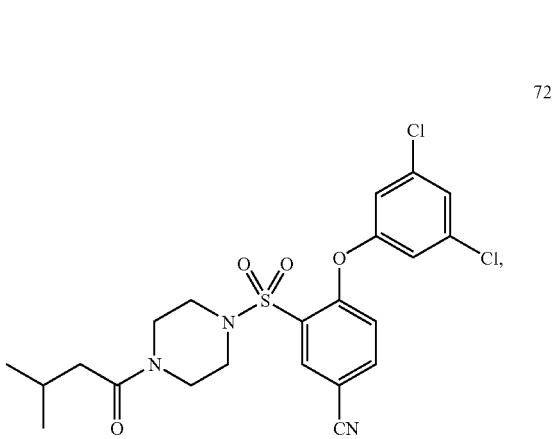

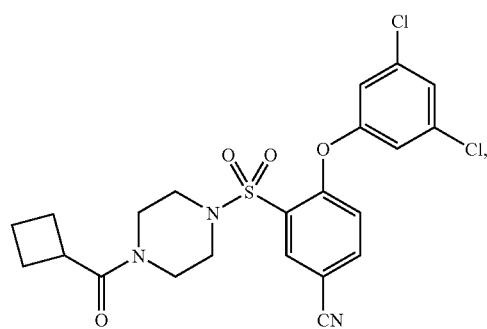
73
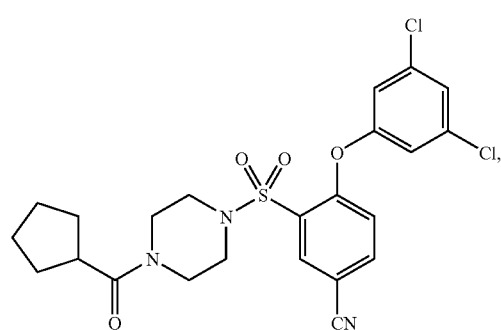
74
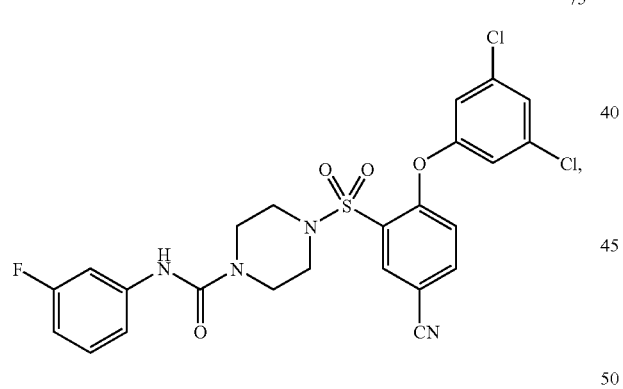
75
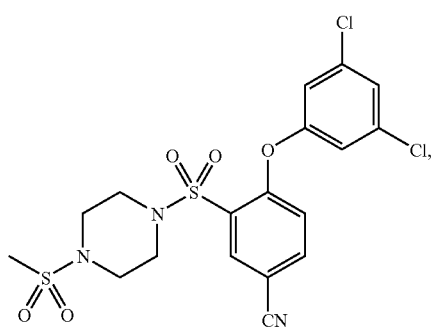
76
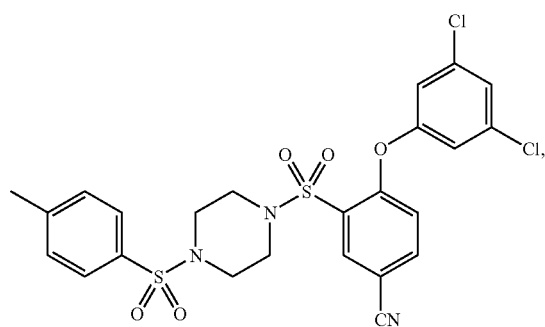
77
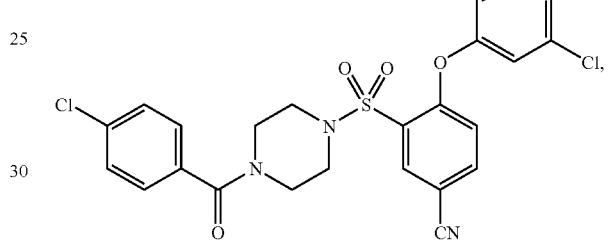
78
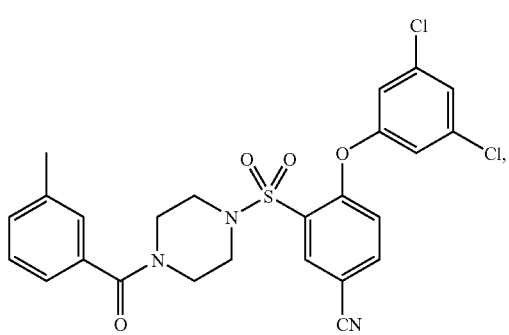
79
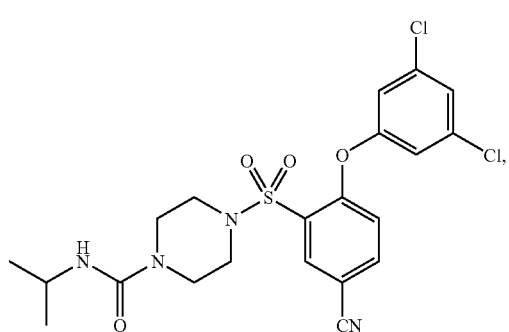
80

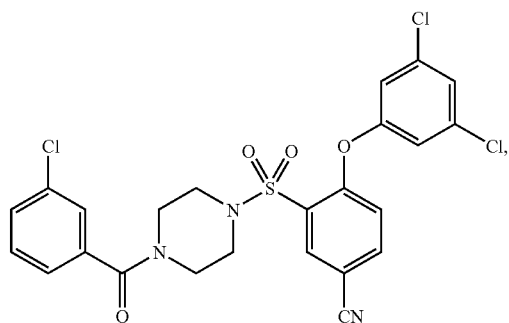
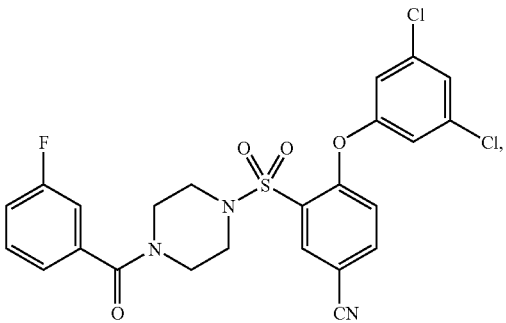
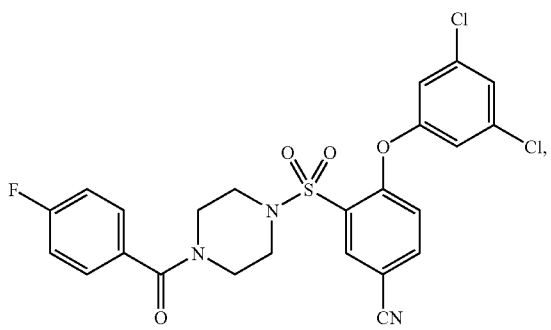
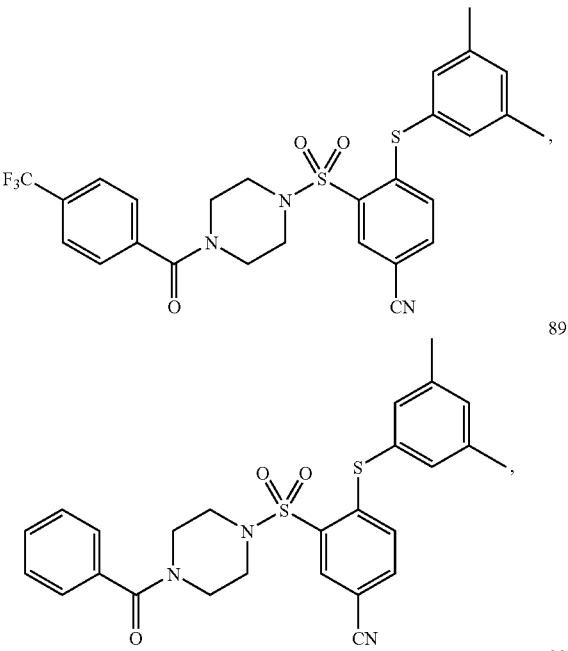
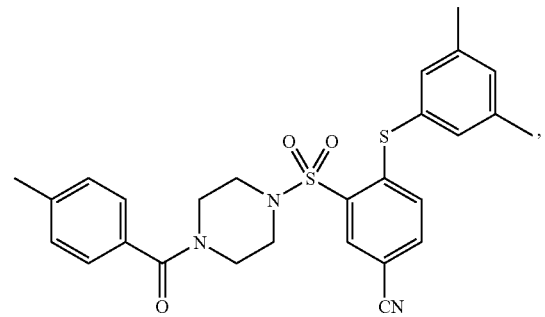

-continued
91 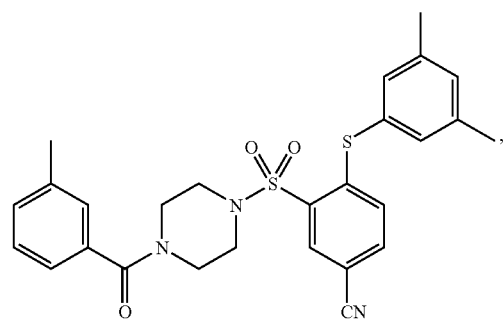
92 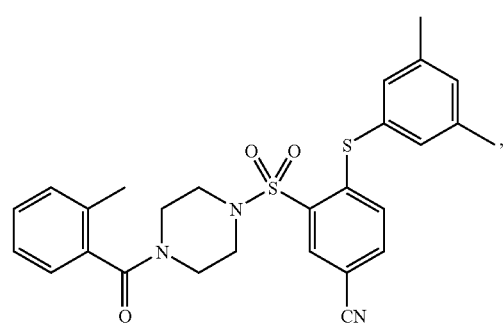
93 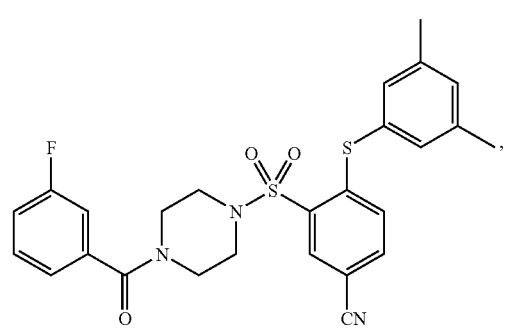
94 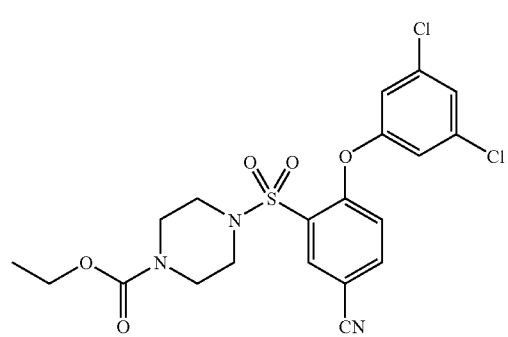
95 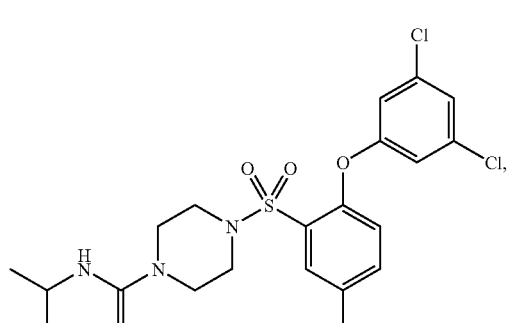
-continued
96 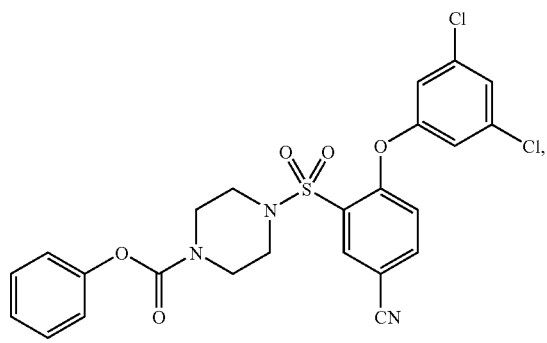
97 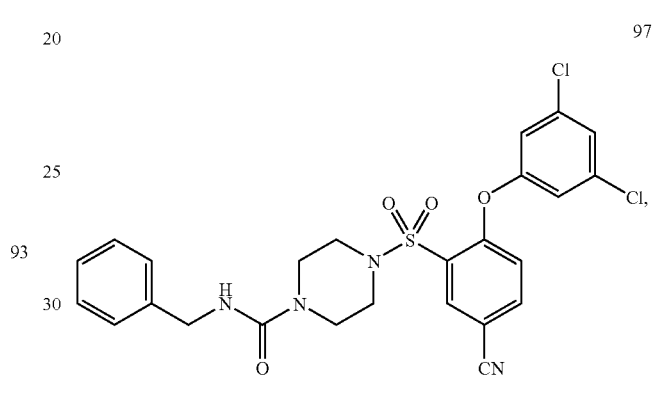
98 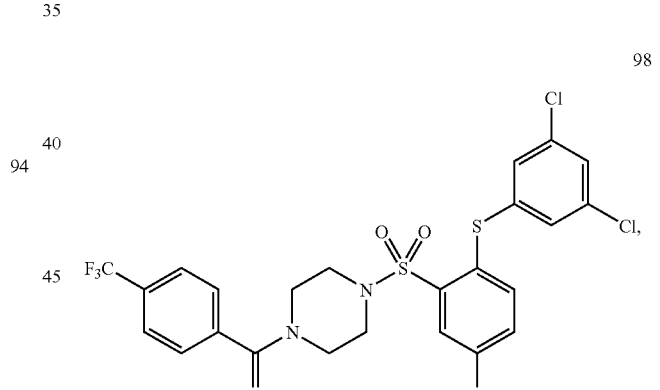
99 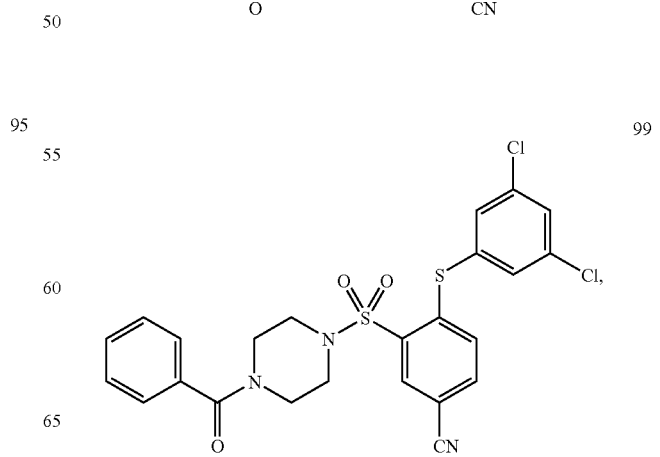

-continued
100
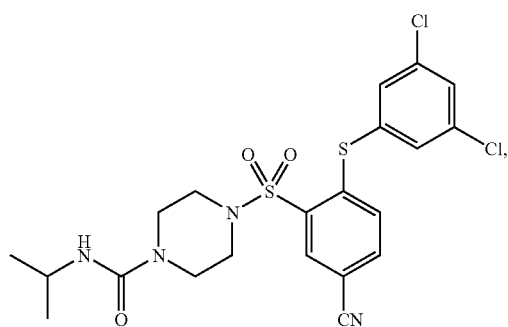
101
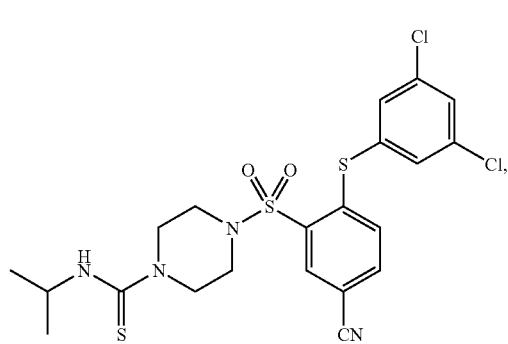
102
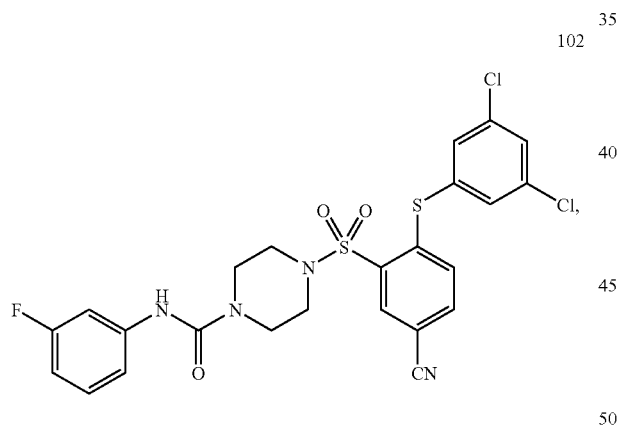
103
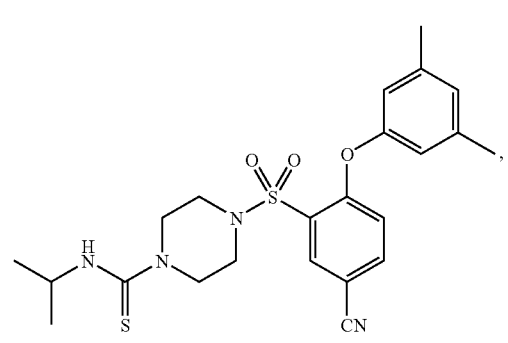
-continued
104
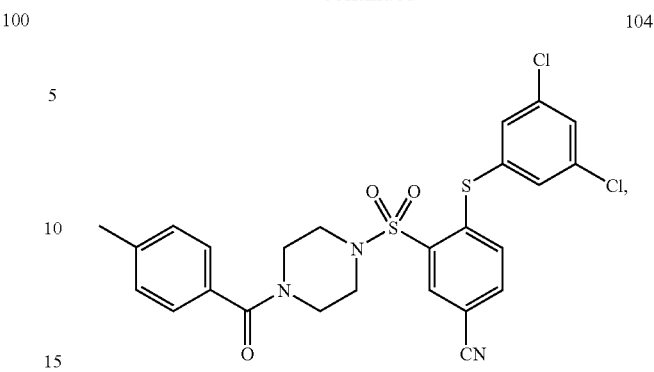
105
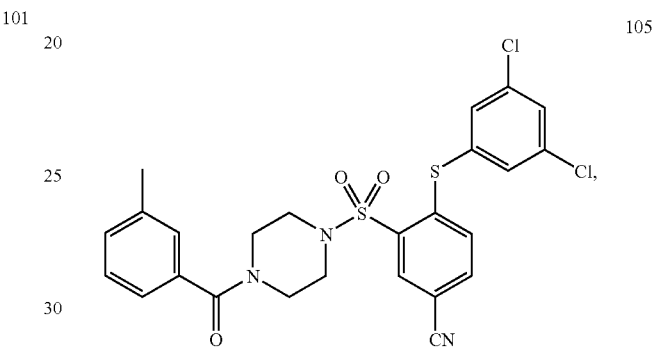
106
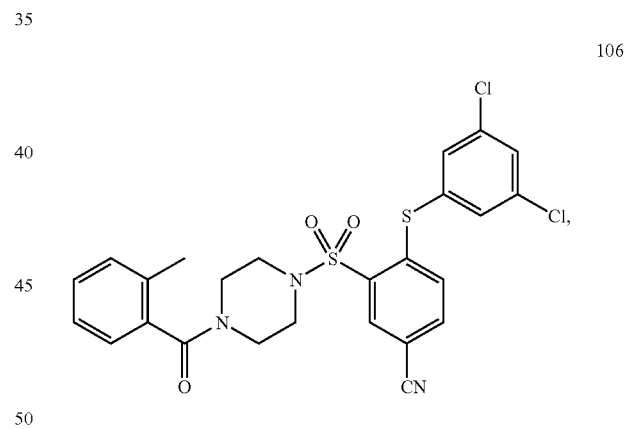
107
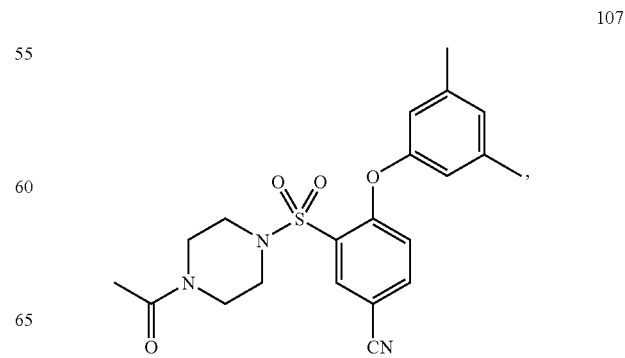

108 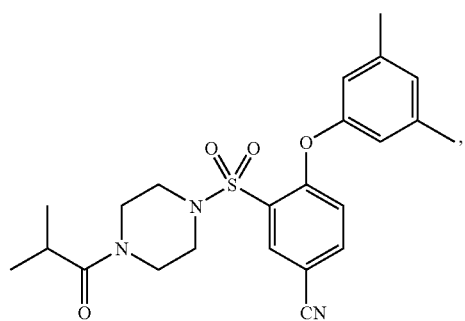
112 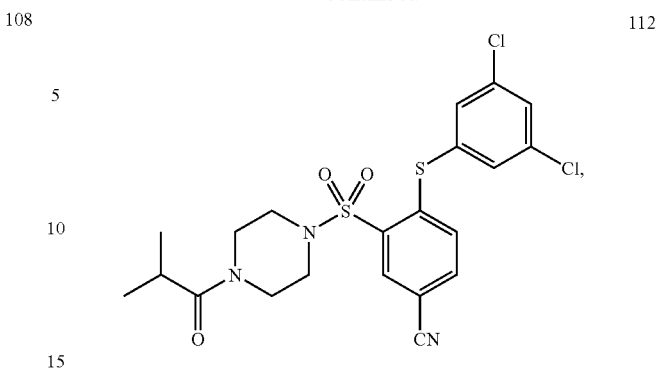
109 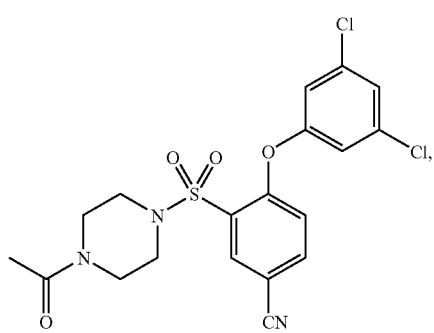
113 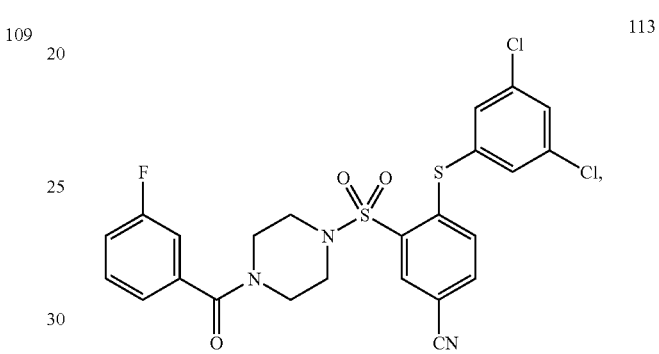
110 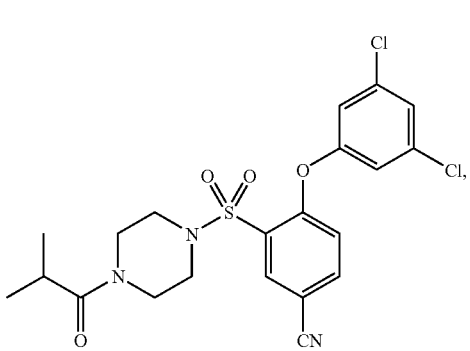
114 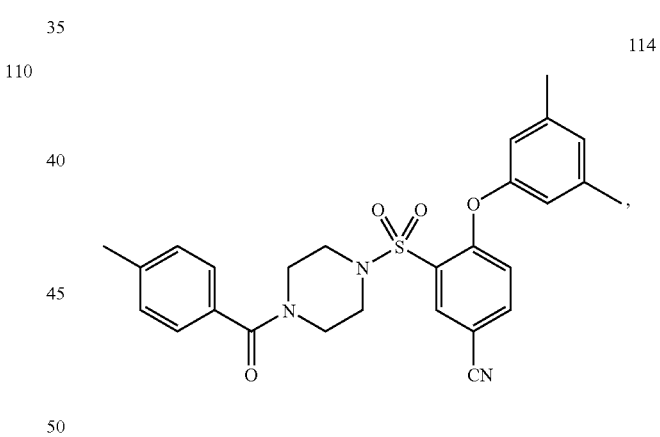
111 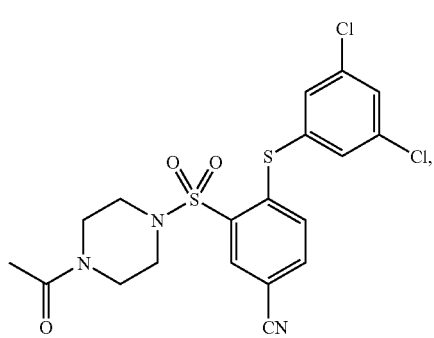
115 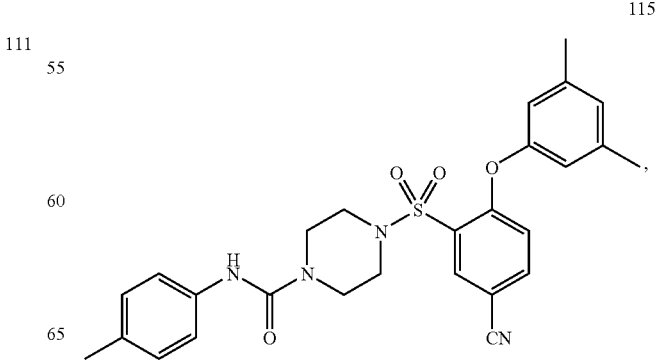

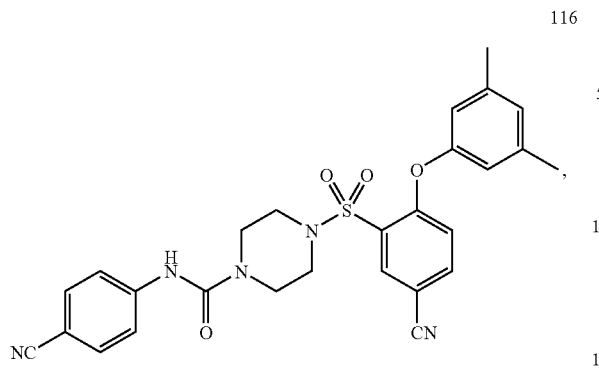
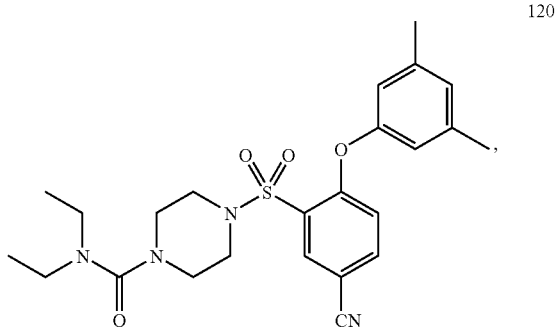

-continued
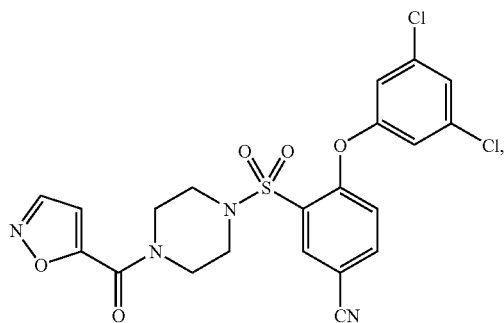
124
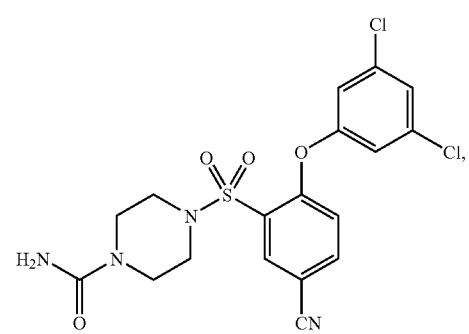
125
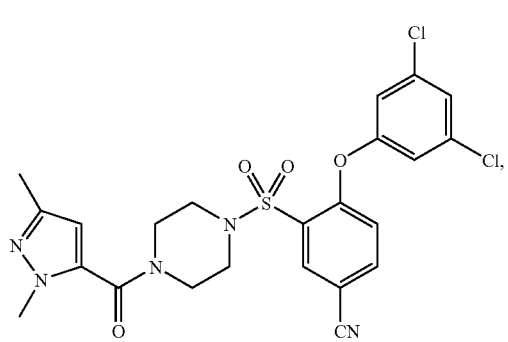
126
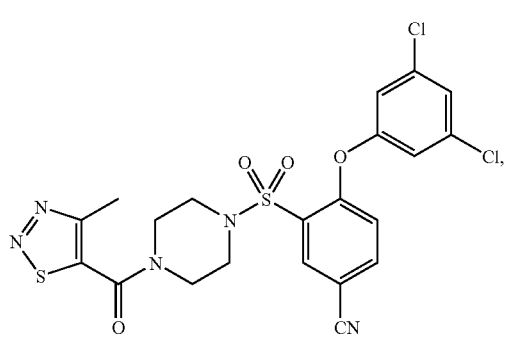
127
-continued
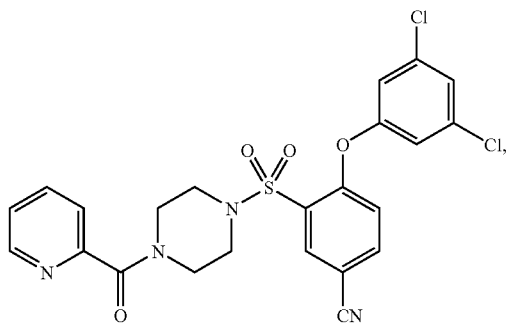
128
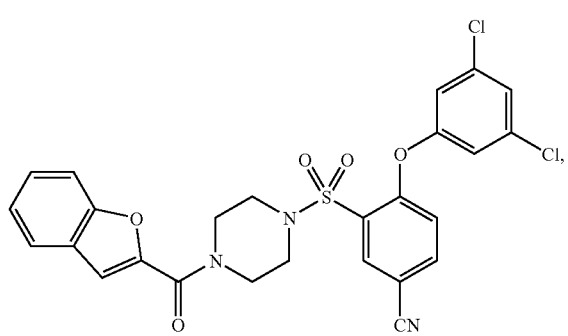
129
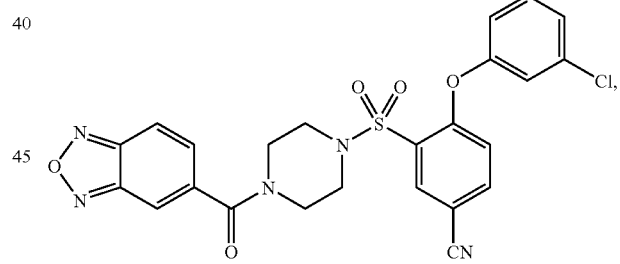
130
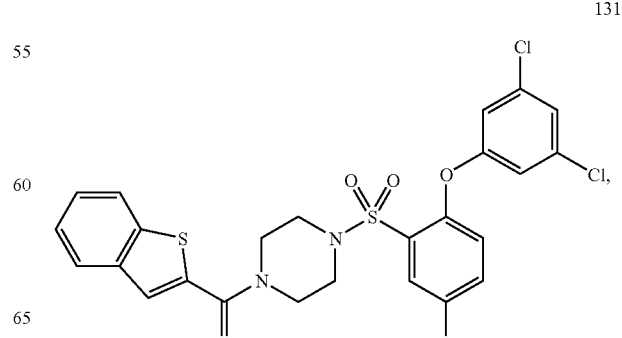
131

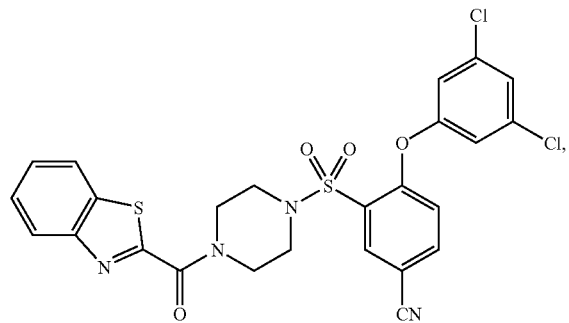
132
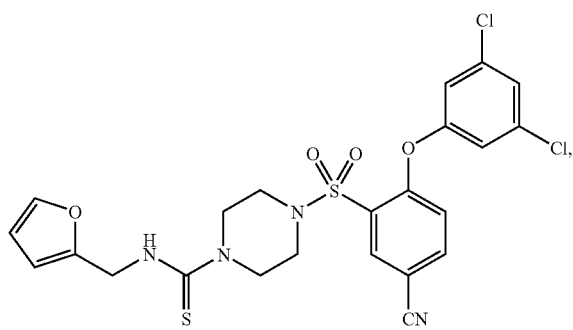
136
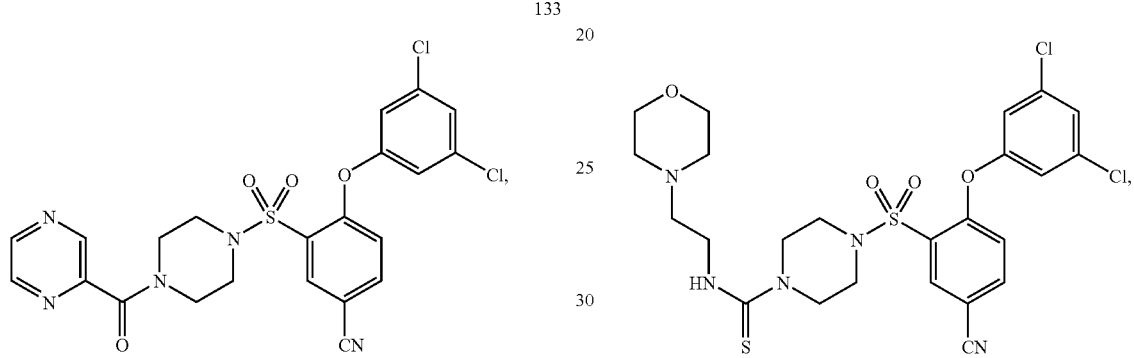
133
137
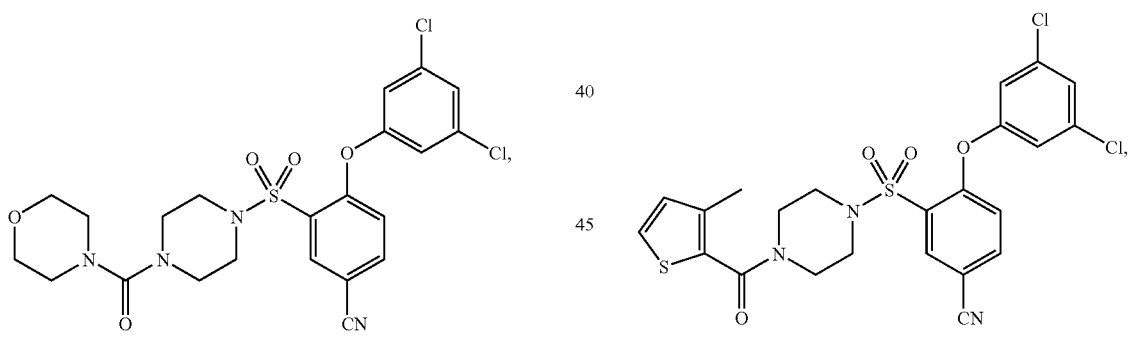
134
138
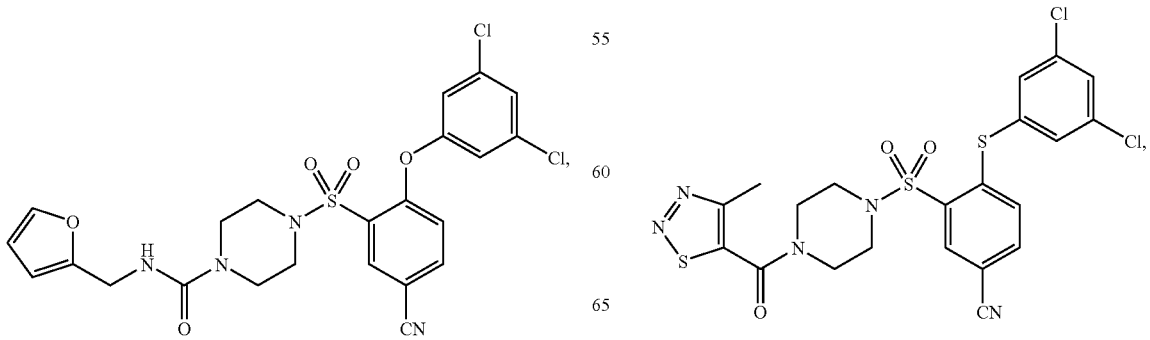
135
139

140
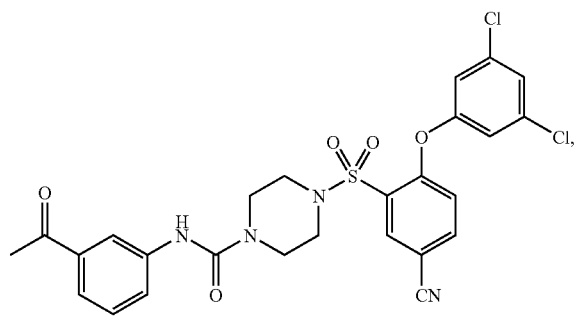
144
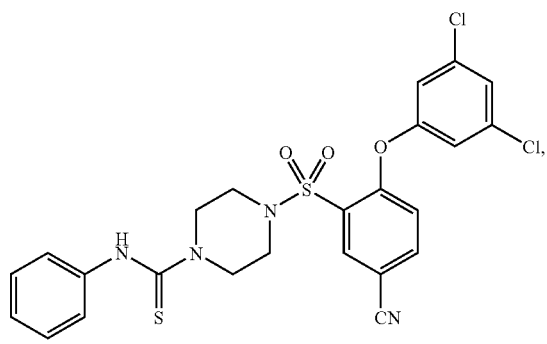
141
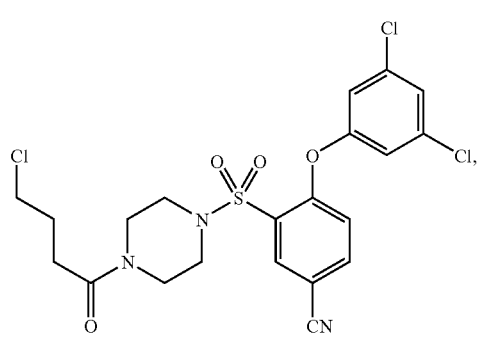
145
145
142
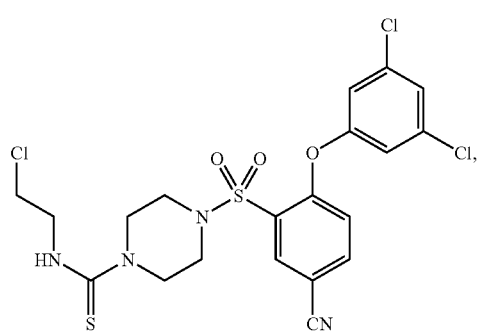
146
143
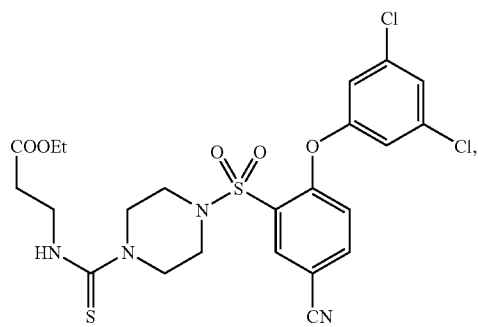
147
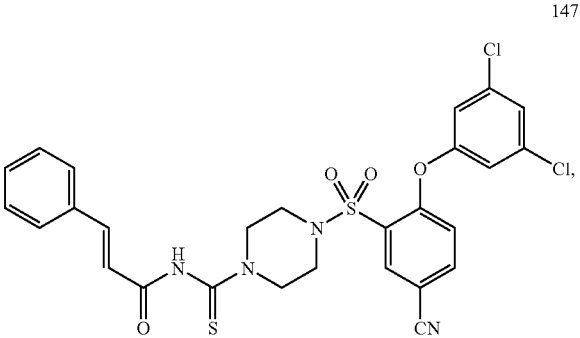

148 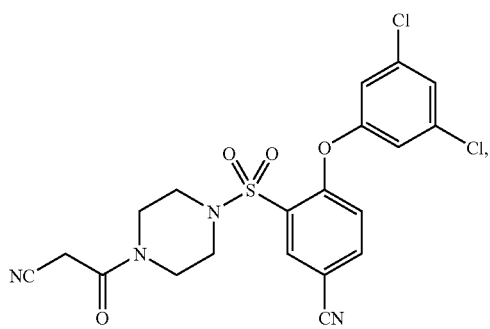
152 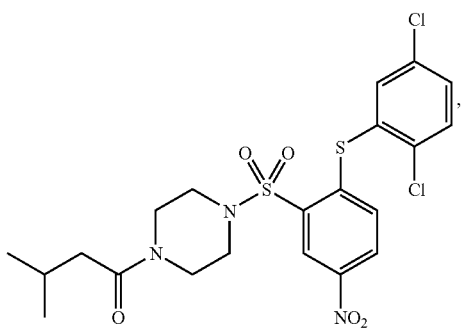
149 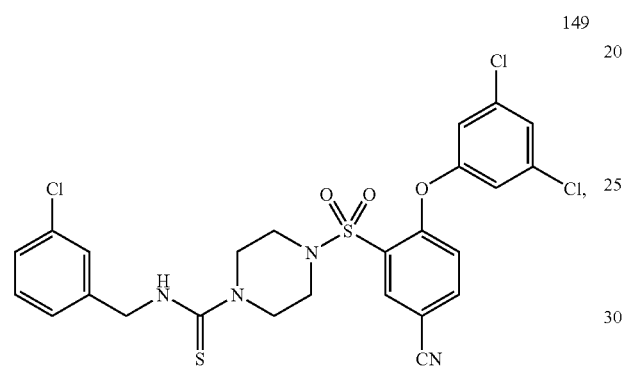
153 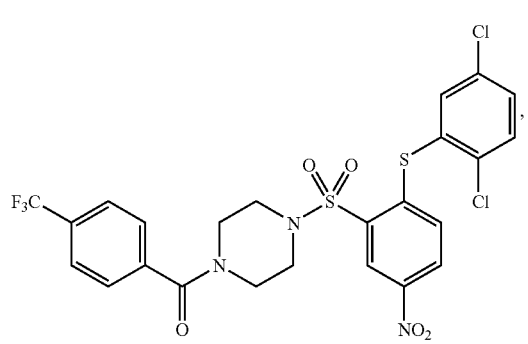
150 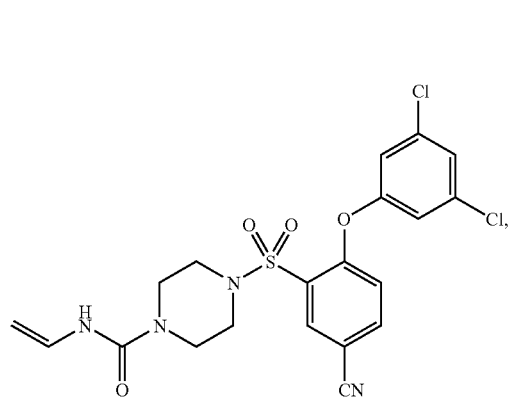
154 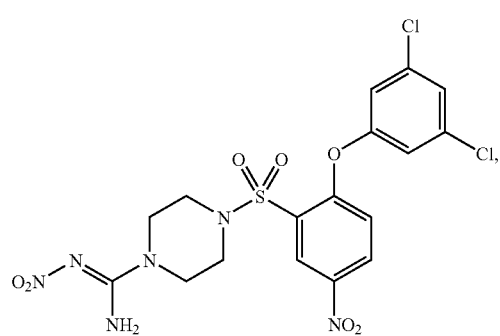
151 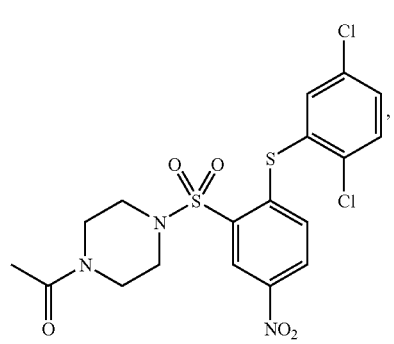
155 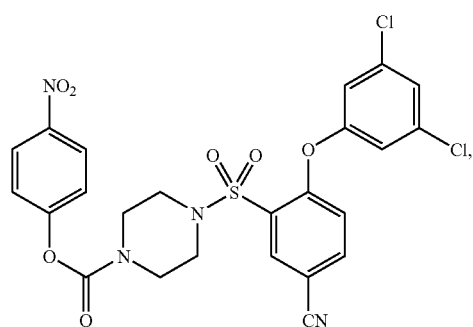

156 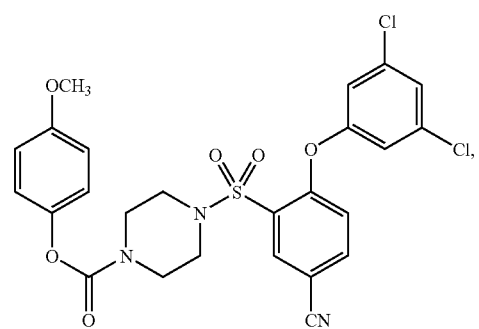
157 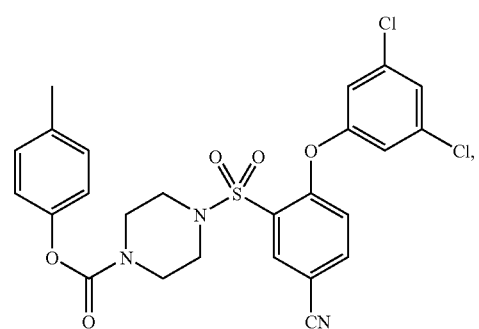
158 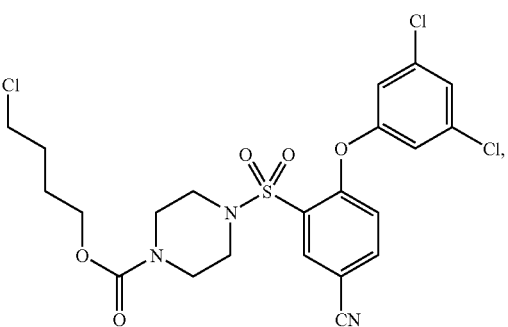
159 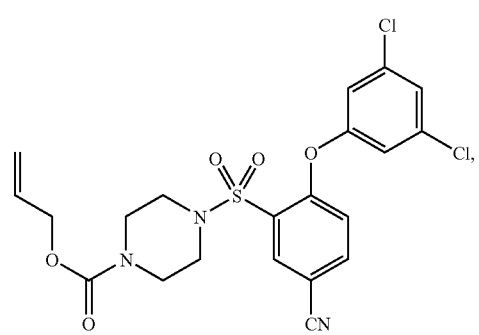
160 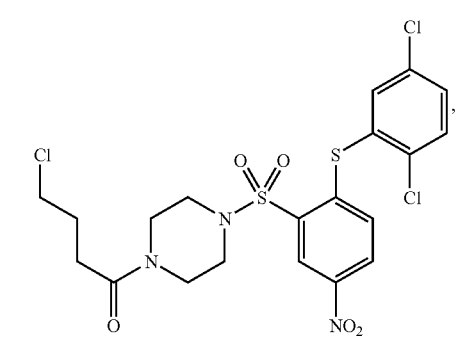
161 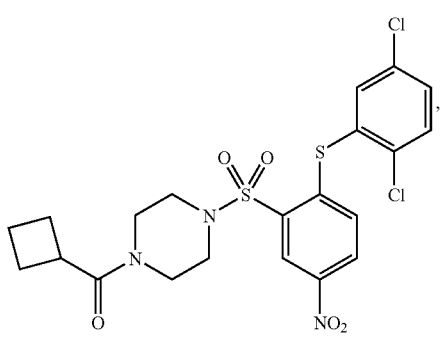
162 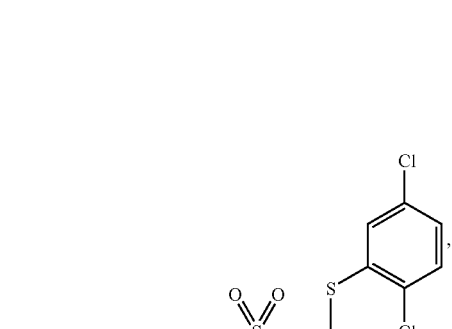
163 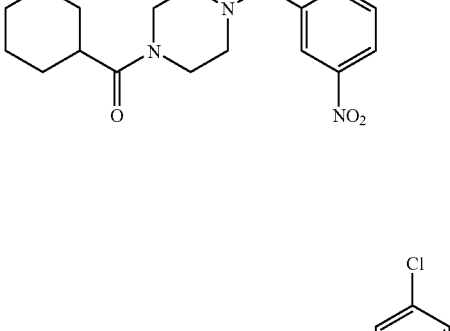
164 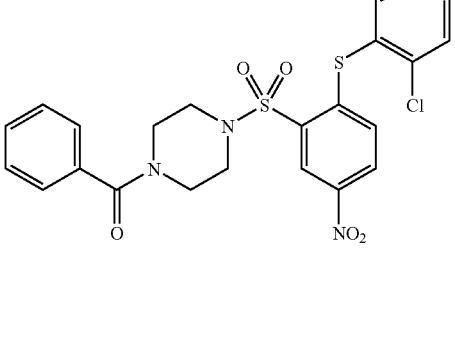
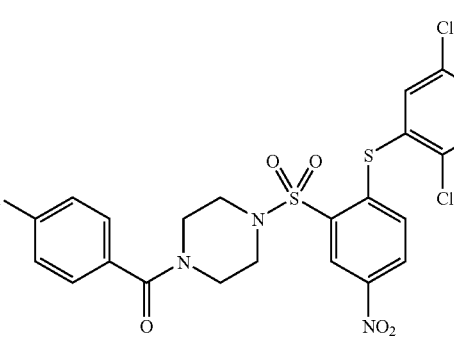

165
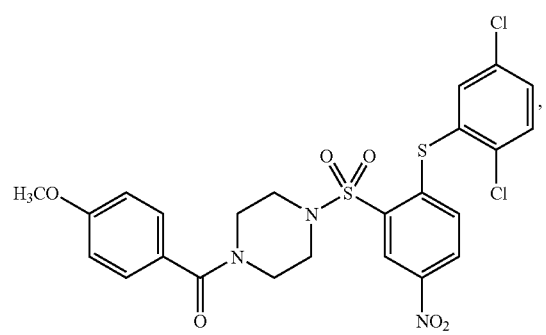
166
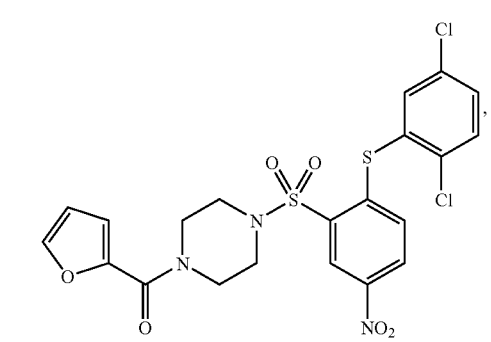
167
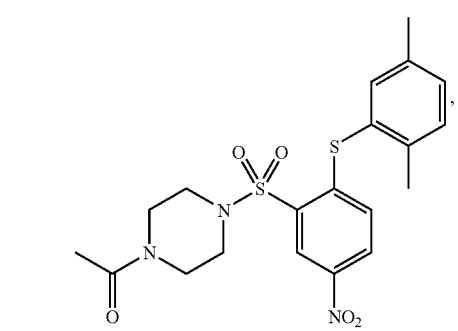
168
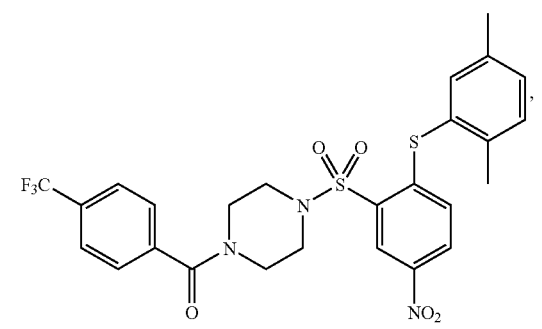
169
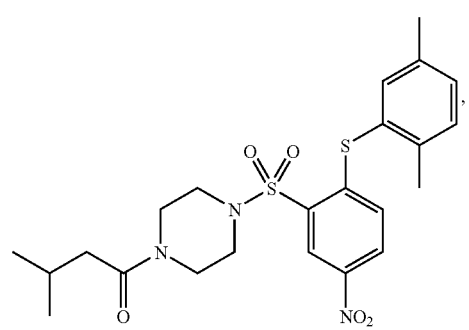
170
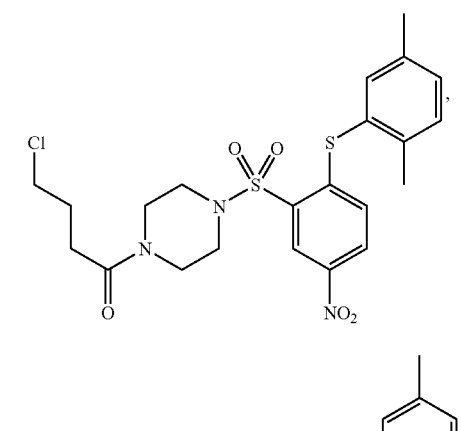
171
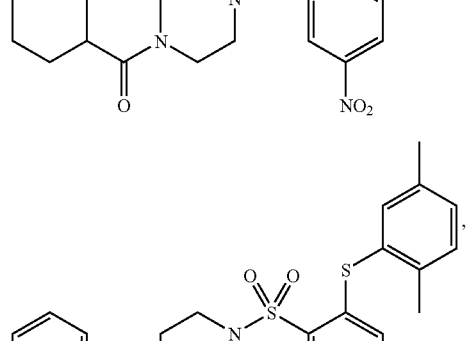
172
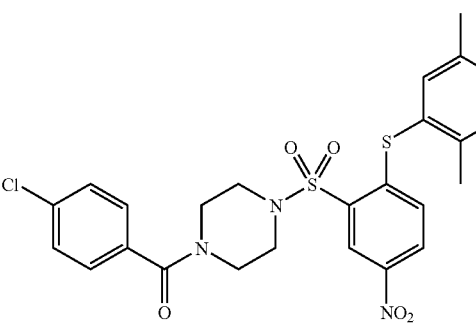
173

174
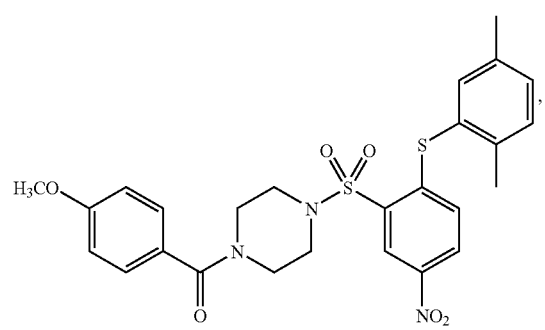
175
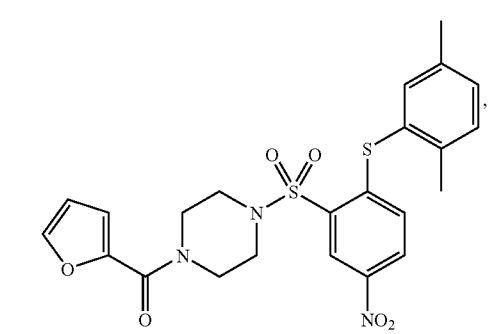
176
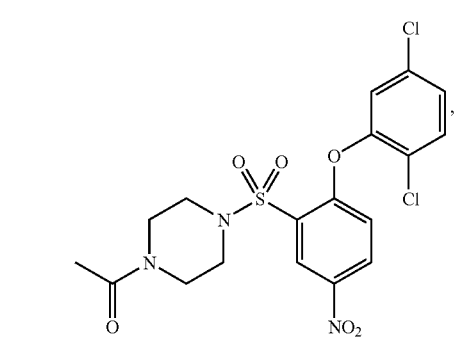
177
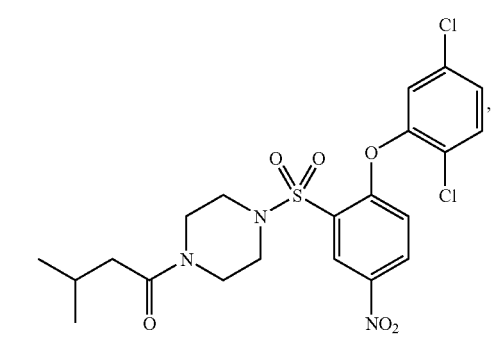
178
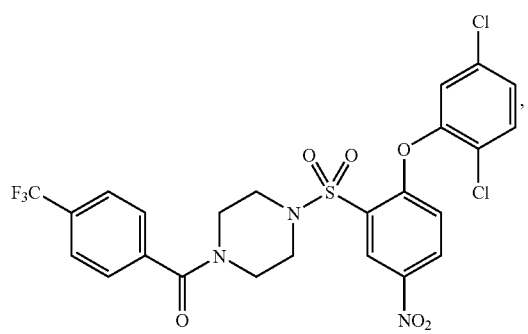
179
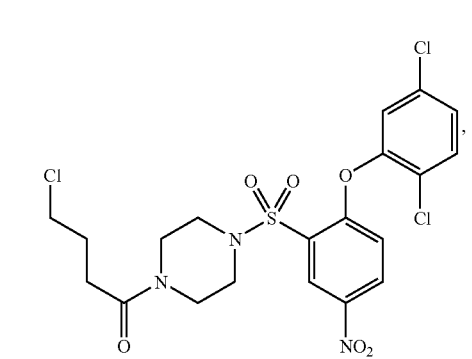
180
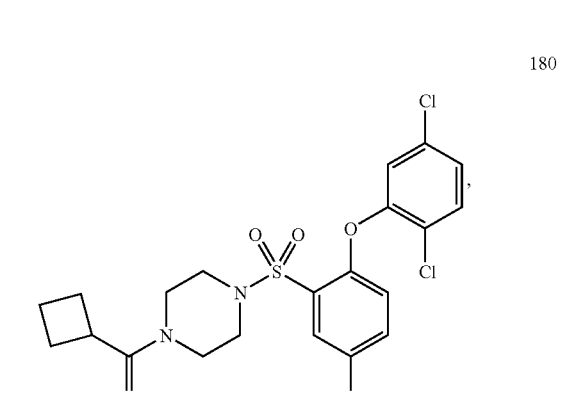
181
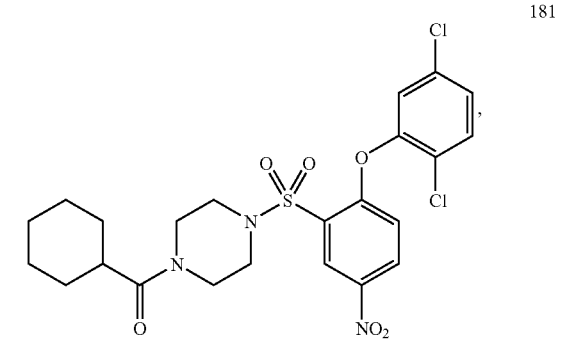

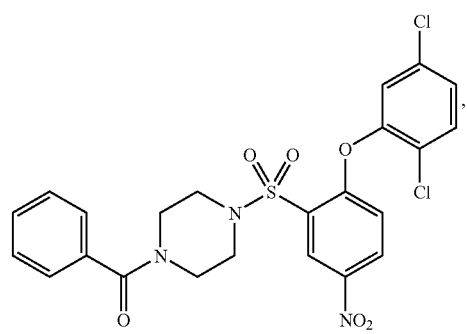
182
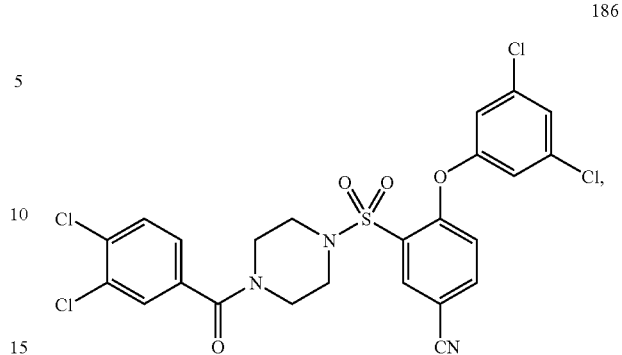
186
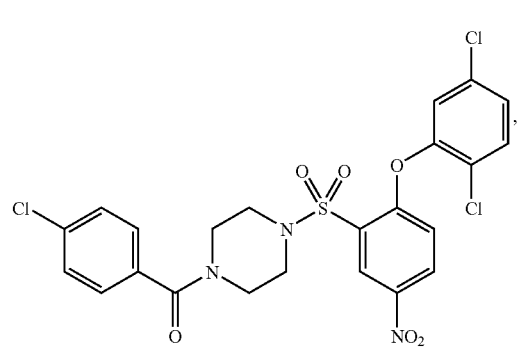
183
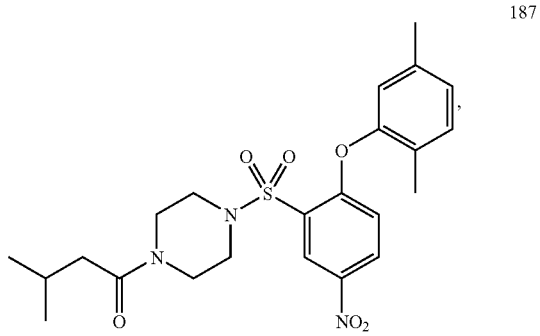
187
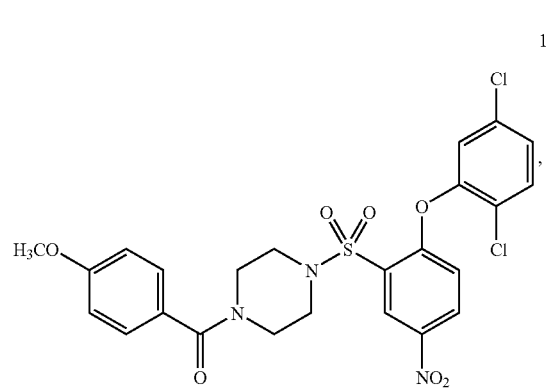
184
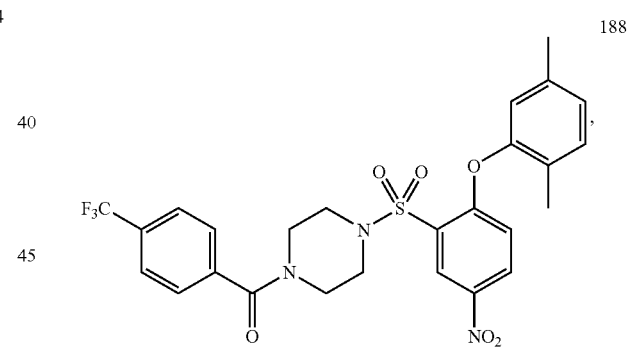
188
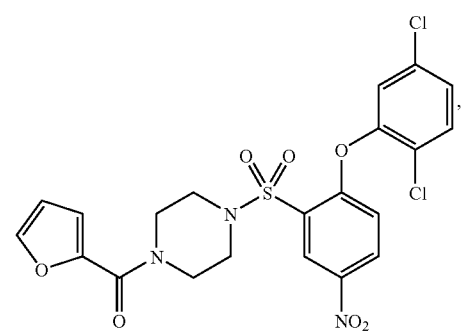
185
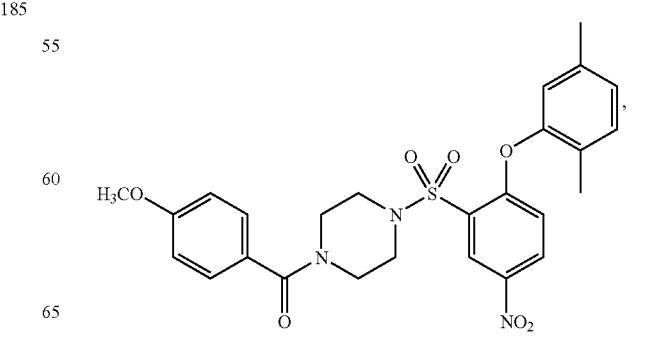
189

-continued
190
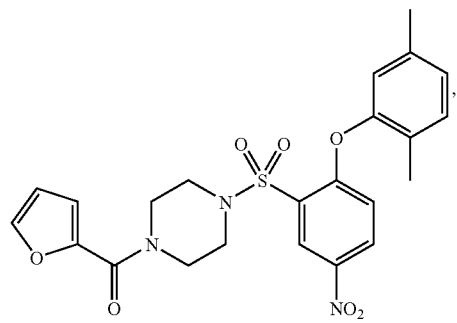
191
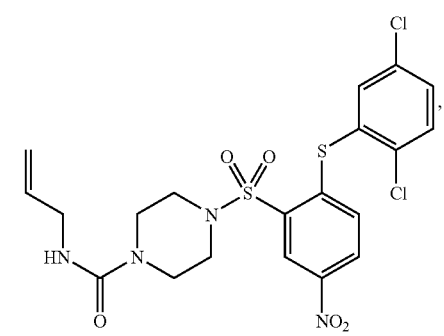
192
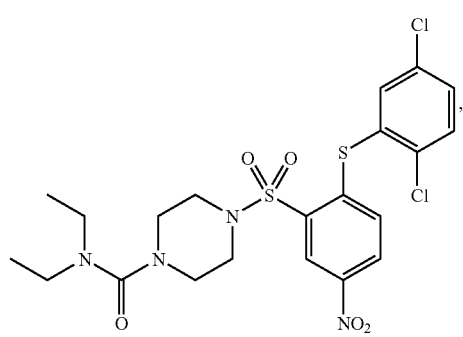
193
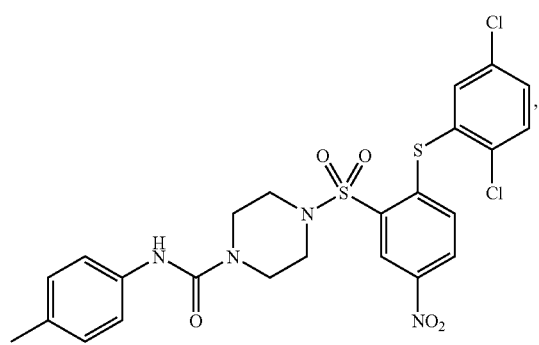
-continued
194
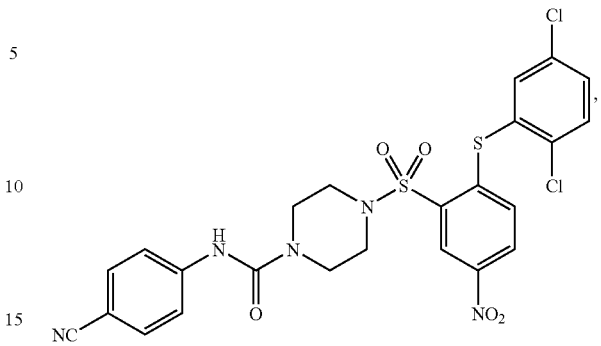
195
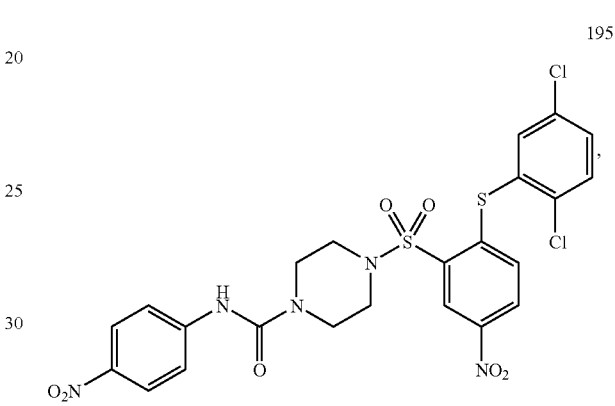
196
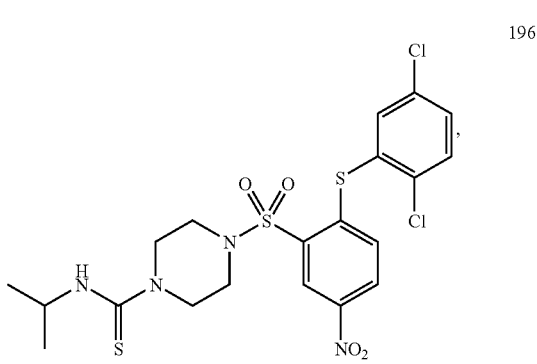
197
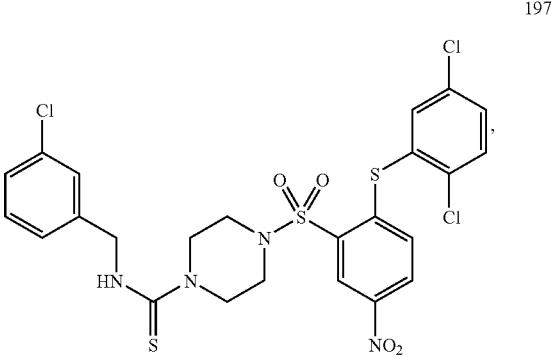

198

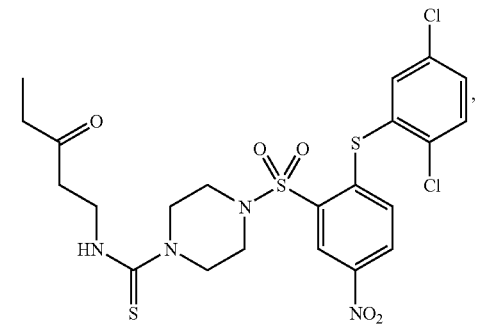

199

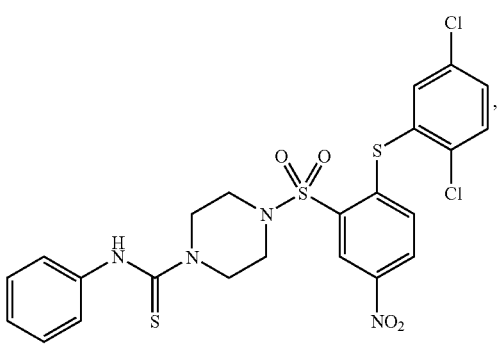

200

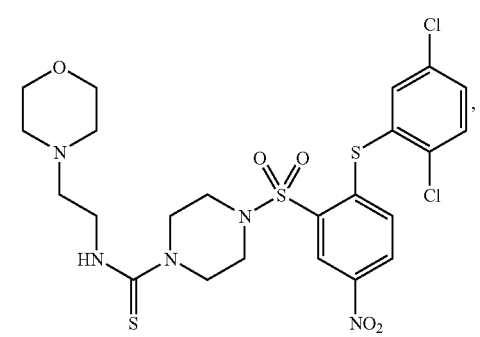

201

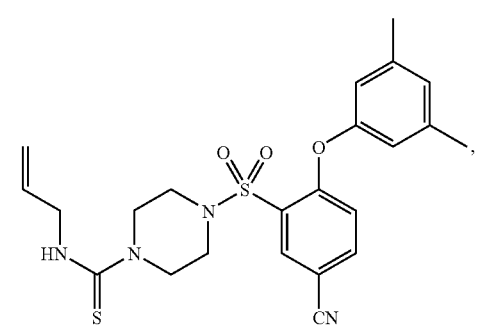

202

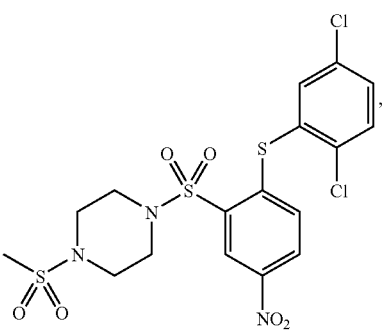

203

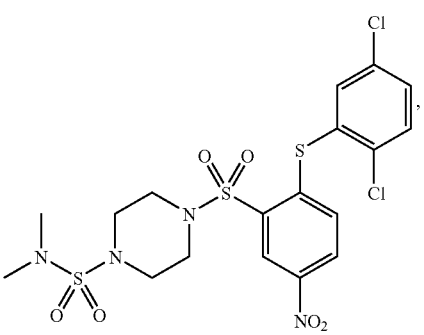

204

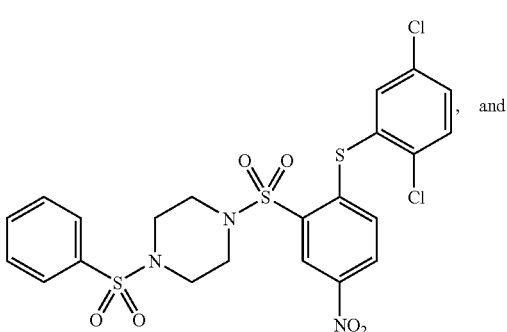

and

205

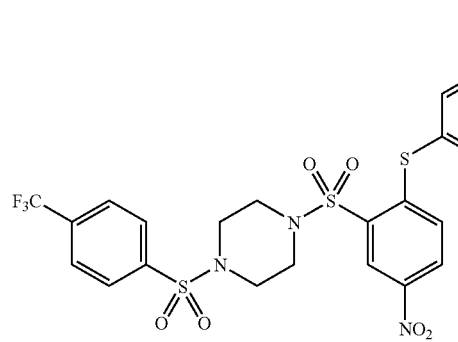

and enantiomers, mixtures of enantiomers, mixtures of two or more diastereomers, tautomers, and mixtures of two or more tautomers thereof; and pharmaceutically acceptable salts, solvates, hydrates, and prodrugs thereof.

The compounds provided herein are intended to encompass all possible stereoisomers, unless a particular stereochemistry is specified. Where the compound provided herein contains an alkenyl or alkenylene group, the compound may exist as one or mixture of geometric cis/trans (or Z/E) isomers. Where structural isomers are interconvertible, the compound may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism.

The compounds provided herein may be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When the compound provided herein contains an acidic or basic moiety, it may also be provided as a pharmaceutically acceptable salt (See, Berge et al., *J. Pharm. Sci.* 1977, 66, 1-19; and "Handbook of Pharmaceutical Salts, Properties, and Use," Stahl and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

In one embodiment, the compound provided here is a hydrochloride salt.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound provided herein may also be provided as a prodrug, which is a functional derivative of the compound, for example, of Formula I and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs*, 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

Methods of Synthesis

The compound provided herein can be prepared, isolated, or obtained by any method known to one of skill in the art. For an example, a compound of Formula I can be prepared as shown in Scheme 1, where $P^1$ is hydrogen or an amino protecting group, e.g., Boc, Cbz, or Fmoc; and $X^1$ is a leaving group, e.g., chloro, bromo, iodo, imidazole, or a carboxylate.

Compound 1 reacts with compound 2 via a nucleophilic aromatic substitution reaction to form compound 3 with release of hydrochloride. The nitro group of the compound 3 was reduced to an amino group with a reducing reagent, e.g., sodium hydrosulfite or tin (II) chloride, to form analine 4, which is subsequently converted into sulfonyl chloride 5 via the Sandmeyer reaction. Compound 5 is then coupled with amine 6, wherein amino protecting group $P^1$ is optional in some embodiments. The removal of protecting group $P^1$ leads to compound 7, which is reacted with $R^{Ya}X^1$ to form a compound of Formula I.

Pharmaceutical Compositions

Provided herein are pharmaceutical compositions comprising a compound provided herein, e.g., a compound of Formula I, as an active ingredient, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof; in combination with a pharmaceutically acceptable vehicle, carrier, diluent, or excipient, or a mixture thereof.

The compound provided herein may be administered alone, or in combination with one or more other compounds provided herein. The pharmaceutical compositions that comprise a compound provided herein, e.g., a compound of Formula I, can be formulated in various dosage forms for oral, parenteral, and topical administration. The pharmaceutical compositions can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Delivery Technology*, 2nd Edition, Rathbone et al., Eds., Marcel Dekker, Inc.: New York, N.Y., 2008).

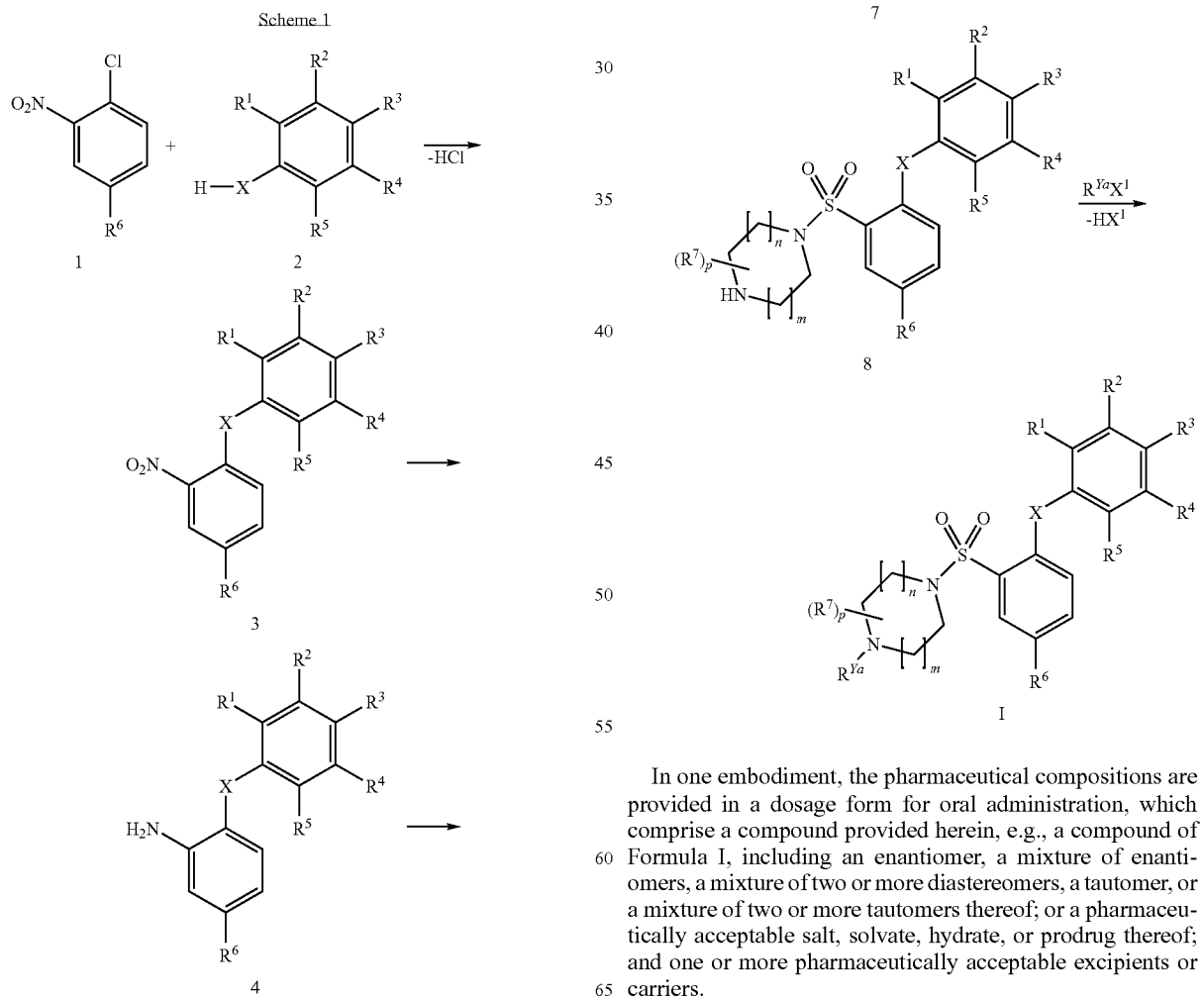

In one embodiment, the pharmaceutical compositions are provided in a dosage form for oral administration, which comprise a compound provided herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof; and one or more pharmaceutically acceptable excipients or carriers.

In another embodiment, the pharmaceutical compositions are provided in a dosage form for parenteral administration, which comprise a compound provided herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof; and one or more pharmaceutically acceptable excipients or carriers.

In yet another embodiment, the pharmaceutical compositions are provided in a dosage form for topical administration, which comprise a compound provided herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof; and one or more pharmaceutically acceptable excipients or carriers.

The pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve several functions, even within the same formulation.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl)acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein for oral administration can be formulated as immediate or modified release dosage forms, including delayed-, sustained-, pulsed-, controlled, targeted-, and programmed-release forms.

B. Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice of Pharmacy, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein can also comprise liposomes, micelles, microspheres, nano systems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid. Combinations of the various vehicles can also be used. Rectal and vaginal suppositories may be prepared by compressing or molding. The typical weight of a rectal and vaginal suppository is about 2 to about 3 g.

The pharmaceutical compositions provided herein can be administered ophthalmically in the forms of solutions, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein; a propellant as solvent; and/or a surfactant, such as sorbitan trioleate, oleic acid, or an oligolactic acid.

The pharmaceutical compositions provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical compositions provided herein; a suitable powder base, such as lactose or starch; and a performance modifier, such as l-leucine, mannitol, or magnesium stearate.

The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical compositions provided herein for inhaled/intranasal administration can further comprise a suitable flavor, such as menthol and levomenthol; and/or sweeteners, such as saccharin and saccharin sodium.

The pharmaceutical compositions provided herein for topical administration can be formulated to be immediate release or modified release, including delayed-, sustained-, pulsed-, controlled-, targeted, and programmed release.

D. Modified Release

The pharmaceutical compositions provided herein can be formulated as a modified release dosage form. As used herein, the term "modified release" refers to a dosage form in which the rate or place of release of the active ingredient(s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form can be fabricated using a matrix controlled release device known to those skilled in the art (see, Takada et al. in "Encyclopedia of Controlled Drug Delivery," Vol. 2, Mathiowitz Ed., Wiley, 1999).

In certain embodiments, the pharmaceutical compositions provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the pharmaceutical compositions provided herein are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form can be prepared by methods known to those skilled in the art, including direct compression, dry or wet granulation followed by compression, and melt-granulation followed by compression.

2. Osmotic Controlled Release Devices

The pharmaceutical compositions provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly (acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical compositions provided herein in a modified release dosage form can be fabricated as a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates can be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical compositions provided herein can also be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Methods of Use

In one embodiment, provided is a method of treating, preventing, or ameliorating one or more symptoms of a disorder, disease, or condition associated with CCR3 in a subject, which comprises administering to the subject a therapeutically effective amount of a compound provided herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof. In one embodiment, the subject is a mammal. In another embodiment, the subject is a human.

In another embodiments, provided is a method of treating, preventing, or ameliorating one or more symptoms of a disorder, disease, or condition responsive to the modulation of CCR3 activity in a subject, comprising administering to the subject a therapeutically effective amount of a compound provided herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof. In one embodiment, the subject is a mammal. In another embodiment, the subject is a human.

In yet another embodiment, provided is a method of treating, preventing, or ameliorating one or more symptoms of a disorder, disease, or condition mediated by a CCR3 receptor in a subject, comprising administering to the subject a therapeutically effective amount of a compound provided herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof. In one embodiment, the subject is a mammal. In another embodiment, the subject is a human.

In yet another embodiment, provided is a method for treating, preventing, or ameliorating one or more symptoms of an eosinophil-related disorder, disease, or condition in a subject, comprising administering to the subject a therapeutically effective amount of a compound provided herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof. In one embodiment, the subject is a mammal. In another embodiment, the subject is a human.

In yet another embodiment, provided is a method for treating, preventing, or ameliorating one or more symptoms of a basophil-related disorder, disease, or condition in a subject, comprising administering to a subject, a therapeutically effective amount of a compound provided herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof. In one embodiment, the subject is a mammal. In another embodiment, the subject is a human.

In yet another embodiment, provided is a method for treating, preventing, or ameliorating one or more symptoms of a mast cell-related disorder, disease, or condition in a subject, comprising administering to a subject a therapeutically effective amount of a compound provided herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof. In one embodiment, the subject is a mammal. In another embodiment, the subject is a human.

In yet another embodiment, provided is a method for treating, preventing, or ameliorating one or more symptoms of an inflammatory disease in a subject, comprising administering to the subject a therapeutically effective amount of a compound provided herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof. In one embodiment, the subject is a mammal. In another embodiment, the subject is a human.

The disorders, diseases, or conditions treatable with a compound provided herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof, include, but are not limited to, (1) inflammatory or allergic diseases, including systemic anaphylaxis and hypersensitivity disorders, atopic dermatitis, urticaria, drug allergies, insect sting allergies, food allergies (including celiac disease and the like), and mastocytosis; (2) inflammatory bowel diseases, including Crohn's disease, ulcerative colitis, ileitis, and enteritis; (3) vasculitis, and Behcet's syndrome; (4) psoriasis and inflammatory dermatoses, including dermatitis, eczema, atopic dermatitis, allergic contact dermatitis, urticaria, viral cutaneous pathologies including those derived from human papillomavirus, HIV or RLV infection, bacterial, flugal, and other parasital cutaneous pathologies, and cutaneous lupus erythematosus; (5) asthma and respiratory allergic diseases, including allergic asthma, exercise induced asthma, allergic rhinitis, otitis media, allergic conjunctivitis, hypersensitivity lung diseases, and chronic obstructive pulmonary disease; (6) autoimmune diseases, including arthritis (including rheumatoid and psoriatic), systemic lupus erythematosus, type I diabetes, myasthenia gravis, multiple sclerosis, Graves' disease, and glomerulonephritis; (7) graft rejection (including allograft rejection and graft-v-host disease), e.g., skin graft rejection, solid organ transplant rejection, bone marrow transplant rejection; (8) fever; (9) cardiovascular disorders, including acute heart failure, hypotension, hypertension, angina pectoris, myocardial infarction, cardiomyopathy, congestive heart failure, atherosclerosis, coronary artery disease, restenosis, and vascular stenosis; (10) cerebrovascular disorders, including traumatic brain injury, stroke, ischemic reperfusion injury and aneurysm; (11) cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood, and lymphatic system; (12) fibrosis, connective tissue disease, and sarcoidosis, (13) genital and reproductive conditions, including erectile dysfunction; (14) gastrointestinal disorders, including gastritis, ulcers, nausea, pancreatitis, and vomiting; (15) neurologic disorders, including Alzheimer's disease; (16) sleep disorders, including insomnia, narcolepsy, sleep apnea syndrome, and Pickwick Syndrome; (17) pain; (18) renal disorders; (19) ocular disorders, including glaucoma; and (20) infectious diseases, including HIV.

In certain embodiments, the disorder, disease, or condition is selected from the group consisting of asthma, allergic asthma, exercise induced asthma, allergic rhinitis, perennial allergic rhinitis, seasonal allergic rhinitis, atopic dermatitis, contact hypersensitivity, contact dermatitis, conjunctivitis, allergic conjunctivitis, eosinophilic bronchitis, food allergies, eosinophilic gastroenteritis, inflammatory bowel disease, ulcerative colitis, Crohn's disease, mastocytosis, hyper IgE syndrome, systemic lupus erythematous, psoriasis, acne, multiple sclerosis, allograft rejection, reperfusion injury, chronic obstructive pulmonary disease, Churg-Strauss syndrome, sinusitis, basophilic leukemia, chronic urticaria, basophilic leukocytosis, psoriasis, eczema, COPD (chronic obstructive pulmonary disorder), arthritis, rheumatoid arthritis, psoriatic arthritis, and osteoarthritis.

In certain embodiments, the disorder, disease, or condition is asthma, exercise induced asthma, allergic rhinitis, atopic dermatitis, chronic obstructive plumonary disease, or allergic conjunctivitis.

Depending on the disorder, disease, or condition to be treated, and the subject's condition, the compounds or pharmaceutical compositions provided herein can be administered by oral, parenteral (e.g., intramuscular, intraperitoneal, intravenous, ICV, intracistemal injection or infusion, subcutaneous injection, or implant), inhalation, nasal, vaginal, rectal, sublingual, or topical (e.g., transdermal or local) routes of administration and can be formulated, alone or together, in suitable dosage unit with pharmaceutically acceptable excipients, carriers, adjuvants, and vehicles appropriate for each route of administration. Also provided is administration of the compounds or pharmaceutical compositions provided herein in a depot formulation, in which the active ingredient is released over a predefined time period.

In the treatment, prevention, or amelioration of one or more symptoms of asthma, allergic rhinitis, eczema, psoriasis, atopic dermatitis, fever, sepsis, systemic lupus erythematosus, diabetes, rheumatoid arthritis, multiple sclerosis, atherosclerosis, transplant rejection, inflammatory bowel disease, cancer, or other conditions, disorders or diseases associated with a CCR3 receptor, an appropriate dosage level generally is ranging from about 0.001 to 100 mg per kg subject body weight per day (mg/kg per day), from about 0.01 to about 75 mg/kg per day, from about 0.1 to about 50 mg/kg per day, from about 0.5 to about 25 mg/kg per day, or from about 1 to about 20 mg/kg per day, which can be administered in single or multiple doses. Within this range, the dosage can be ranging from about 0.005 to about 0.05, from about 0.05 to about 0.5, from about 0.5 to about 5.0, from about 1 to about 15, from about 1 to about 20, or from about 1 to about 50 mg/kg per day. In certain embodiments, the dosage level is ranging from about 0.001 to about 100 mg/kg per day. In certain embodiments, the dosage level is ranging from about 0.01 to about 75 mg/kg per day. In certain embodiments, the dosage level is ranging from about 0.1 to about 50 mg/kg per day. In certain embodiments, the dosage level is ranging from about 0.5 to about 25 mg/kg per day. In certain embodiments, the dosage level is ranging from about 1 to about 20 mg/kg per day.

For oral administration, the pharmaceutical compositions provided herein can be formulated in the form of tablets containing from about 1.0 to about 1,000 mg of the active ingredient, in one embodiment, about 1, about 5, about 10, about 15, about 20, about 25, about 50, about 75, about 100, about 150, about 200, about 250, about 300, about 400, about 500, about 600, about 750, about 800, about 900, and about 1,000 mg of the active ingredient for the symptomatic adjustment of the dosage to the patient to be treated. The pharmaceutical compositions can be administered on a regimen of 1 to 4 times per day, including once, twice, three times, and four times per day.

It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Also provided herein are methods of modulating CCR3 activity, comprising contacting a CCR3 receptor with a compound provided herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof. In one embodiment, the CCR3 receptor is expressed by a cell.

The compounds provided herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof, can also be combined or used in combination with other agents useful in the treatment, prevention, or amelioration of one or more symptoms of the disorders, diseases, or conditions for which the compounds provided herein are useful, including asthma, allergic rhinitis, eczema, psoriasis, atopic dermatitis, fever, sepsis, systemic lupus erythematosus, diabetes, rheumatoid arthritis, multiple sclerosis, atherosclerosis, transplant rejection, inflammatory bowel disease, cancer, infectious diseases, and those pathologies noted above.

In certain embodiments, the compounds provided herein can be combined with one or more steroidal drugs known in the art, including, but not limited to the group including, aldosterone, beclometasone, betamethasone, deoxycorticosterone acetate, fludrocortisone, hydrocortisone (cortisol), prednisolone, prednisone, methylprednisolone, dexamethasone, and triamcinolone.

In certain embodiments, the compounds provided herein can be combined with one or more antibacterial agents known in the art, including, but not limited to the group including amikacin, amoxicillin, ampicillin, arsphenamine, azithromycin, aztreonam, azlocillin, bacitracin, carbenicillin, cefaclor, cefadroxil, cefamandole, cefazolin, cephalexin, cefdinir, cefditorin, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clindamycin, cloxacillin, colistin, dalfopristin, demeclocycline, dicloxacillin, dirithromycin, doxycycline, erythromycin, enrofloxacin, ertepenem, ethambutol, flucloxacillin, fosfomycin, furazolidone, gatifloxacin, geldanamycin, gentamicin, herbimycin, imipenem, isoniazid, kanamycin, levofloxacin, linezolid, lomefloxacin, loracarbef, mafenide, moxifloxacin, meropenem, metronidazole, mezlocillin, minocycline, mupirocin, nafcillin, neomycin, netilmicin, nitrofurantoin, norfloxacin, ofloxacin, oxytetracycline, penicillin, piperacillin, platensimycin, polymyxin B, prontocil, pyrazinamide, quinupristine, rifampin, roxithromycin, spectinomycin, streptomycin, sulfacetamide, sulfamethizole, sulfamethoxazole, teicoplanin, telithromycin, tetracycline, ticarcillin, tobramycin, trimethoprim, troleandomycin, trovafloxacin, and vancomycin.

In certain embodiments, the compounds provided herein can be combined with one or more antifungal agents known in the art, including, but not limited to the group including amorolfine, amphotericin B, anidulafungin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, nystatin, oxyconazole, ravuconazole, posaconazole, rimocidin, sertaconazole, sulconazole, terbinafine, terconazole, tioconazole, and voriconazole.

In certain embodiments, the compounds provided herein can be combined with one or more anticoagulants known in the art, including, but not limited to the group including acenocoumarol, argatroban, bivalirudin, lepirudin, fondaparinux, heparin, phenindione, warfarin, and ximelagatran.

In certain embodiments, the compounds provided herein can be combined with one or more thrombolytics known in the art, including, but not limited to the group including anistreplase, reteplase, t-PA (alteplase activase), streptokinase, tenecteplase, and urokinase.

In certain embodiments, the compounds provided herein can be combined with one or more non-steroidal anti-inflammatory agents known in the art, including, but not limited to, aceclofenac, acemetacin, amoxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, ketoprofen, ketorolac, lornoxicam, loxoprofen, lumiracoxib, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, and tolmetin.

In certain embodiments, the compounds provided herein can be combined with one or more antiplatelet agents known in the art, including, but not limited to, abciximab, cilostazol, clopidogrel, dipyridamole, ticlopidine, and tirofibin.

The compounds provided herein can also be administered in combination with other classes of compounds, including, but not limited to, (1) alpha-adrenergic agents; (2) antiarrhythmic agents; (3) anti-atherosclerotic agents, such as ACAT inhibitors; (4) antibiotics, such as anthracyclines, bleomycins, mitomycin, dactinomycin, and plicamycin; (5) anticancer agents and cytotoxic agents, e.g., alkylating agents, such as nitrogen mustards, alkyl sulfonates, nitrosoureas, ethylenimines, and triazenes; (6) anticoagulants, such as acenocoumarol, argatroban, bivalirudin, lepirudin, fondaparinux, heparin, phenindione, warfarin, and ximelagatran; (7) anti-diabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thiozolidinediones (e.g., troglitazone, rosiglitazone, and pioglitazone), and PPAR-gamma agonists; (8) antifungal agents, such as amorolfine, amphotericin B, anidulafungin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, nystatin, oxyconazole, ravuconazole, posaconazole, rimocidin, sertaconazole, sulconazole, terbinafine, terconazole, tioconazole, and voriconazole; (9) antiinflammatories, e.g., non-steroidal anti-inflammatory agents, such as aceclofenac, acemetacin, amoxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, ketoprofen, ketorolac, lornoxicam, loxoprofen, lumiracoxib, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, and tolmetin; (10) antimetabolites, such as folate antagonists, purine analogues, and pyrimidine analogues; (11) anti-platelet agents, such as GPIIb/IIIa blockers (e.g., abciximab, eptifibatide, and tirofiban), P2Y(AC) antagonists (e.g., clopidogrel, ticlopidine and CS-747), cilostazol, dipyridamole, and aspirin; (12) antiproliferatives, such as methotrexate, FK506 (tacrolimus), and mycophenolate mofetil; (13) anti-TNF antibodies or soluble TNF receptor, such as etanercept, rapamycin, and leflunimide; (14) aP2 inhibitors; (15) beta-adrenergic agents, such as carvedilol and metoprolol; (16) bile acid sequestrants, such as questran; (17) calcium channel blockers, such as amlodipine besylate; (18) chemotherapeutic agents; (19) cyclooxygenase-2 (COX-2) inhibitors, such as celecoxib and rofecoxib; (20) cyclosporins; (21) cytotoxic drugs, such as azathioprine and cyclophosphamide; (22) diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, ticrynafen, chlorthalidone, furosenide, muzolimine, bumetanide, triamterene, amiloride, and spironolactone; (23) endothelin converting enzyme (ECE) inhibitors, such as phosphoramidon; (24) enzymes, such as L-asparaginase; (25) Factor VIIa Inhibitors and Factor Xa Inhibitors; (26) farnesyl-protein transferase inhibitors; (27) fibrates; (28) growth factor inhibitors, such as modulators of PDGF activity; (29) growth hormone secretagogues; (30) HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, atavastatin, or visastatin); neutral endopeptidase (NEP) inhibitors; (31) hormonal agents, such as glucocorticoids (e.g., cortisone), estrogens/antiestrogens, androgens/antiandrogens, progestins, and luteinizing hormone-releasing hormone antagonists, and octreotide acetate; (32) immunosuppressants; (33) mineralocorticoid receptor antagonists, such as spironolactone and eplerenone; (34) microtubule-disruptor agents, such as ecteinascidins; (35) microtubule-stabilizing agents, such as pacitaxel, docetaxel, and epothilones A-F; (36) MTP Inhibitors; (37) niacin; (38) phosphodiesterase inhibitors, such as PDE III inhibitors (e.g., cilostazol) and PDE V inhibitors (e.g., sildenafil, tadalafil, and vardenafil); (39) plant-derived products, such as vinca alkaloids, epipodophyllotoxins, and taxanes; (40) platelet activating factor (PAF) antagonists; (41) platinum coordination complexes, such as cisplatin, satraplatin, and carboplatin; (42) potassium channel openers; (43) prenyl-protein transferase inhibitors; (44) protein tyrosine kinase inhibitors; (45) renin inhibitors; (46) squalene synthetase inhibitors; (47) steroids, such as aldosterone, beclometasone, betamethasone, deoxycorticosterone acetate, fludrocortisone, hydrocortisone (cortisol), prednisolone, prednisone, methylprednisolone, dexamethasone, and triamcinolone; (48) TNF-alpha inhibitors, such as tenidap; (49) thrombin inhibitors, such as hirudin; (50) thrombolytic agents, such as anistreplase, reteplase, tenecteplase, tissue plasminogen activator (tPA), recombinant tPA, streptokinase, urokinase, prourokinase, and anisoylated plasminogen streptokinase activator complex (APSAC); (51) thromboxane receptor antagonists, such as ifetroban; (52) topoisomerase inhibitors; (53) vasopeptidase inhibitors (dual NEP-ACE inhibitors), such as omapatrilat and gemopatrilat; and (54) other miscellaneous agents, such as, hydroxyurea, procarbazine, mitotane, hexamethylmelamine, and gold compounds.

Such other agents, or drugs, can be administered, by a route and in an amount commonly used therefor, simultaneously or sequentially with the compounds provided herein, e.g., a compound of Formula I, including a single enantiomer, a mixture of enantiomers, or a mixture of diastereomers thereof; or a pharmaceutically acceptable salt, solvate, or prodrug thereof. When a compound provided herein is used contemporaneously with one or more other drugs, a pharmaceutical composition containing such other drugs in addition to the compound provided herein can be utilized, but is not required. Accordingly, the pharmaceutical compositions provided herein include those that also contain one or more other active ingredients or therapeutic agents, in addition to a compound provided herein.

The weight ratio of a compound provided herein to the second active ingredient can be varied, and will depend upon the effective dose of each ingredient. Generally, an effective dose of each will be used. Thus, for example, when a compound provided herein is combined with a NSAID, the weight ratio of the compound to the NSAID can range from about 1,000:1 to about 1:1,000, or about 200:1 to about 1:200. Combinations of a compound provided herein and other active ingredients will generally also be within the aforementioned range, but in each case, an effective dose of each active ingredient should be used.

The compounds provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

Provided herein also are kits which, when used by the medical practitioner, can simplify the administration of appropriate amounts of active ingredients to a subject. In certain embodiments, the kit provided herein includes a container and a dosage form of a compound provided herein, including a single enantiomer or a mixture of diastereomers thereof; or a pharmaceutically acceptable salt, solvate, or prodrug thereof.

In certain embodiments, the kit includes a container comprising a dosage form of the compound provided herein, including a single enantiomer or a mixture of diastereomers thereof; or a pharmaceutically acceptable salt, solvate, or prodrug thereof, in a container comprising one or more other therapeutic agent(s) described herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL (microliters); mM (millimolar); µM (micromolar); Hz (Hertz); MHz (megahertz); mmol (millimoles); hr or hrs (hours); min (minutes); MS (mass spectrometry); ESI (electrospray ionization); TLC (thin layer chromatography); HPLC (high pressure liquid chromatography); THF (tetrahydrofuran); $CDCl_3$ (deuterated chloroform); DMSO (dimethylsulfoxide); DMSO-$d_6$ (deuterated dimethylsulfoxide); EtOAc (ethyl acetate); and MeOH (methanol).

For all of the following examples, standard work-up and purification methods known to those skilled in the art can be utilized. Unless otherwise indicated, all temperatures are expressed in ° C. (degrees Centigrade). All reactions are conducted at room temperature unless otherwise noted. Synthetic methodologies illustrated herein are intended to exemplify the applicable chemistry through the use of specific examples and are not indicative of the scope of the disclosure.

Example 1

Preparation of 4-(3,5-dimethylphenoxy)-3-(4-propionylpiperazin-1-ylsulfonyl)benzonitrile 57

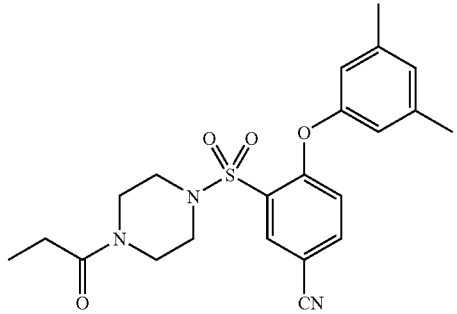

Compound 57 was synthesized as shown in Scheme 2.

Scheme 2

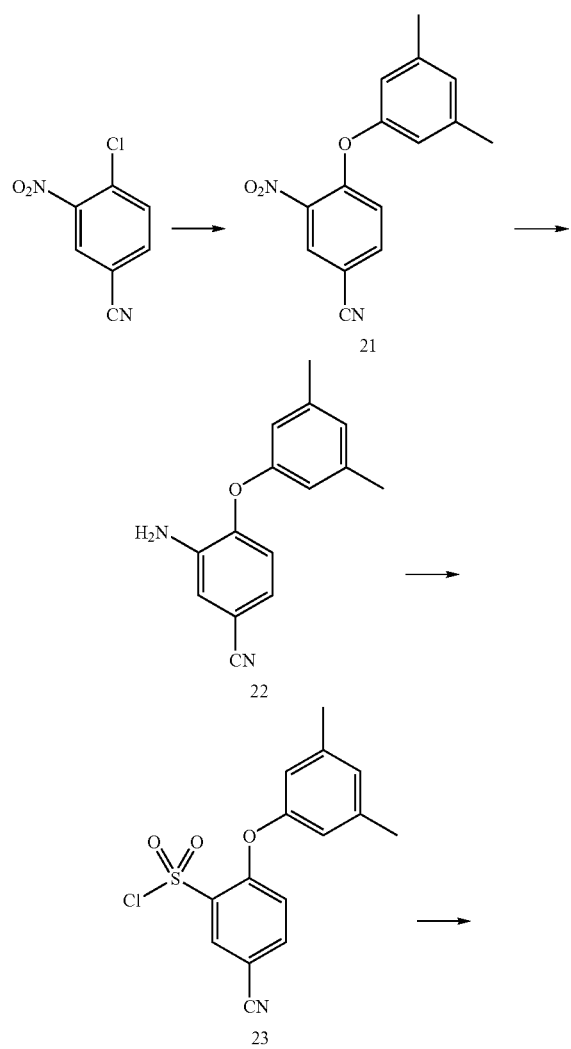

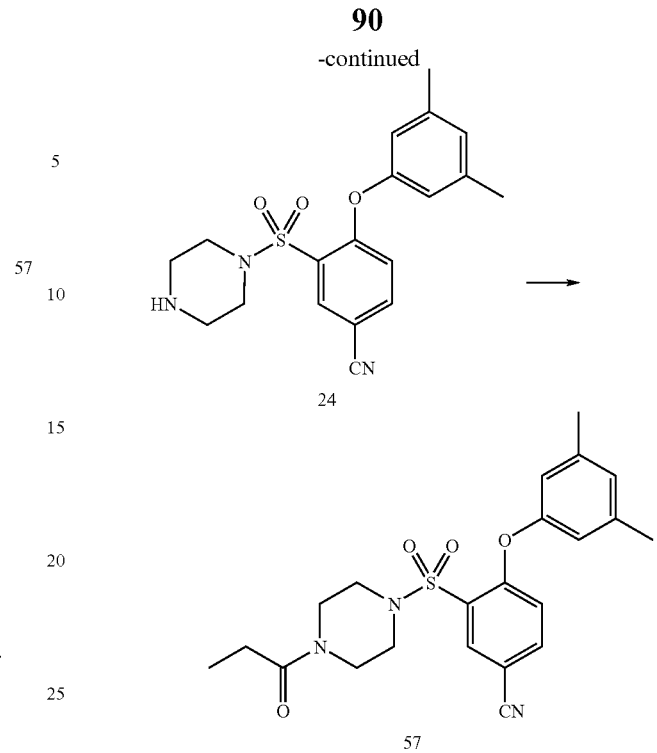

4-(3,5-Dimethylphenoxy)-3-nitrobenzonitrile 21. To a solution of 4-chloro-3-nitrobenzonitrile (12.00 g, 65.75 mmol) in THF was added potassium carbonate (45.58 g, 328.70 mmol) and 3,5-dimethylphenol (9.658 g, 78.88 mmol). The reaction mixture was refluxed for 17 hrs, whereupon the starting material was consumed (TLC, 25% EtOAc in hexanes). The reaction mixture was then cooled to room temperature, and potassium carbonate was filtered and washed with copious amounts of EtOAc. The filtrate was washed sequentially with saturated sodium bicarbonate solution, water, and saturated sodium chloride solution, dried over anhydrous MgSO$_4$, filtered, and concentrated in vacuo to give the crude product as a yellow solid. The solid was triturated with hexanes and filtered to afford compound 21 as a whitish-yellow powder. (15.022 g, 85.2% yield, 100% HPLC purity). $^1$H NMR (500 MHz, DMSO-d$_6$): δ 8.65 (d, J=2 Hz, 1H), 8.06 (dd, J$_1$=9 Hz, J$_2$=2 Hz, 1H), 7.12 (d, J=9 Hz, 1H), 6.97 (s, 1H), 6.84 (s, 2H), 2.29 (s, 6H).

3-Amino-4-(3,5-dimethylphenoxy)benzonitrile 22. A solution of compound 21 (15.00 g, 55.91 mmol) in THF (250 mL) was added a solution of sodium hydrosulfite (58.41 g, 335.5 mmol) in water (75 mL). The reaction mixture was stirred at 90° C. After 24 hrs, the starting material was consumed as monitored with TLC (10% EtOAc in hexanes) and reaction mixture was removed from heat. The reaction mixture was concentrated in vacuo until product precipitated in remaining water. The precipitate was collected via vacuum filtration and washed with water. The product was dried overnight in vacuum at 40° C. to afford compound 22. (12.681 g, 95.2% yield, 99.9% HPLC purity). $^1$H NMR (500 MHz, DMSO-d$_6$): δ 7.08 (d, J=2 Hz, 1H), 6.91 (dd, J$_1$=8 Hz, J$_2$=2 Hz, 1H), 6.80 (s, 1H), 6.73 (d, J=8 Hz, 1H), 6.63 (s, 2H), 5.47 (s, 2H), 2.24 (s, 6H).

5-Cyano-2-(3,5-dimethylphenoxy)benzene-1-sulfonyl chloride 23. Compound 22 (12.00 g, 50.36 mmol) was added to H$_2$O (50.0 mL) and concentrated HCl (100 mL) at room temperature. The reaction mixture was then stirred in an ice bath. Sodium nitrite (10.434 g, 151.1 mmol) in H$_2$O (50 mL)

was added to the reaction mixture dropwise at 0° C. The reaction mixture was allowed to stir in the ice bath for an hour. In a separate flask, sulfur dioxide was bubbled through acetic acid (430 mL) for 45 min. Cupric chloride dihydrate (4.305 g, 25.2 mmol) was then added to this sulfur dioxide saturated solution, and stirred for an additional 30 min. This saturated sulfur dioxide solution was then stirred in an ice bath for an additional five min. The reaction mixture containing compound 22 was then added dropwise to the cupric chloride solution. After the addition was complete, the solution was stirred for an additional hour and then poured slowly onto an ice water slurry and stirred for an hour. The resulting precipitate was then filtered and the yellow solid was rinsed with water to afford compound 23 (13.944 g, 86.1% yield). $^1$H NMR (500 MHz, DMSO-$d_6$): δ 8.06 (d, J=2 Hz, 1H), 7.71 (dd, $J_1$=8 Hz, $J_2$=2 Hz, 1H), 6.85 (s, 1H), 6.81 (d, J=9 Hz, 1H), 6.66 (s, 2H), 2.26 (s, 6H).

4-(3,5-Dimethylphenoxy)-3-(piperazin-1-ylsulfonyl)benzonitrile 24. To a solution of piperazine (16.144 g, 186.4 mmol) in $CH_2Cl_2$ (80 mL) stirred in an ice-brine bath was added dropwise of a solution of compound 23 (3.009 g, 9.35 mmol) in $CH_2Cl_2$ (270 mL) over the course of two days. The reaction was then stirred for 74 hrs, whereupon the starting material was consumed (TLC, 5% MeOH in $CH_2Cl_2$). The reaction mixture was partitioned between $CH_2Cl_2$ and water. The organic layer was then washed with saturated sodium chloride solution and dried over anhydrous $MgSO_4$. The organic layer was then concentrated in vacuo, redissolved in a minimal amount of $CH_2Cl_2$, and chromatographed over normal phase silica (MeOH/$CH_2Cl_2$). The fractions containing the desired product were combined and concentrated in vacuo to yield an light yellow oil. The oil was then triturated with $CH_2Cl_2$/diisopropyl ether and vacuum filtered to afford compound 24 as a white powder (2.032 g, 58.5% yield, 95.5% HPLC purity). $^1$H NMR (500 MHz, DMSO-$d_6$): δ 8.21 (d, J=2 Hz, 1H), 8.03 (dd, $J_1$=9 Hz, $J_2$=2 Hz, 1H), 7.01 (m, 1H), 6.96 (d, J=11 Hz, 1H), 6.80 (d, J=9 Hz, 2H), 3.19 (m, 2H), 3.11 (m, 2H), 2.70 (m, 2H), 2.46 (m, 2H), 2.30 (s, 1H), 2.27 (s, 6H).

4-(3,5-Dimethylphenoxy)-3-(4-propionylpiperazin-1-ylsulfonyl)benzonitrile 57. To a solution of compound 24 (0.102 g, 0.27 mmol) in $CH_2Cl_2$ (2 mL) was added propionyl chloride (0.035 g, 0.38 mmol) and triethylamine (0.039 g, 0.38 mmol). The reaction mixture was stirred at room temperature for 20 hrs, whereupon the starting material was consumed (TLC, 1% MeOH in $CH_2Cl_2$). The reaction mixture was concentrated in vacuo, redissolved in a minimal amount of $CH_2Cl_2$, and chromatographed over normal phase silica (MeOH/$CH_2Cl_2$). The fractions containing the desired product were combined and concentrated in vacuo to yield a white powder, which was then triturated with $CH_2Cl_2$/diisopropyl ether and vacuum filtered to yield the desired product as a powder. The powder was redissolved in $CH_2Cl_2$ and chromatographed for a second time over normal phase silica (MeOH/$CH_2Cl_2$). The fractions containing the desired product were combined and concentrated in vacuo to yield a white powder. The powder was triturated with diisopropyl ether and vacuum filtered to yield compound 57 (0.061 g, 52.1% yield, 96.6% HPLC purity). $^1$H NMR (500 MHz, CDCl$_3$): 8.27 (d, J=2 Hz, 1H), 7.67 (dd, $J_1$=9 Hz, $J_2$=2 Hz, 1H), 6.94 (s, 1H), 6.90 (d, J=9 Hz, 1H), 6.68 (s, 2H), 3.71 (m, 2H), 3.54 (m, 2H), 3.35 (m, 4H), 2.34 (s, 6H), 2.32 (m, 2H), 1.13 (t, J=7 Hz, 3H); MS (ESI, EI$^+$): m/z=428 (MH$^+$).

The following compounds were made according to the procedures as described in this example.

4-(3,5-Dimethylphenoxy)-3-(4-(4-(trifluoromethyl)benzoyl)piperazin-1-ylsulfonyl)benzonitrile 54. HPLC purity: 96.6%; $^1$H NMR (500 MHz, DMSO-$d_6$): 8.23 (d, J=2 Hz, 1H), 8.05 (dd, $J_1$=9 Hz, $J_2$=2 Hz, 1H), 7.80 (d, J=8 Hz, 2H), 7.62 (d, J=8 Hz, 2H), 7.03 (d, J=9 Hz, 1H), 6.97 (s, 1H), 6.86 (s, 2H), 3.71 (m, 2H), 3.35 (m, 4H), 3.26 (m, 2H), 2.30 (s, 6H); MS (ESI, EI$^+$): m/z=544 (MH$^+$).

3-(4-Benzoylpiperazin-1-ylsulfonyl)-4-(3,5-dimethylphenoxy)benzonitrile 55. HPLC purity: 95.5%; $^1$H NMR (500 MHz, DMSO-$d_6$): 8.23 (d, J=2 Hz, 1H), 8.05 (dd, $J_1$=9 Hz, $J_2$=2 Hz, 1H), 7.42 (m, 5H), 7.02 (d, J=9 Hz, 1H), 6.97 (s, 1H), 6.87 (s, 2H), 3.68 (m, 2H), 3.38 (m, 2H), 3.30 (m, 4H), 2.30 (s, 6H); MS (ESI, EI$^+$): m/z=478 (MH$^+$).

3-(4-(2,2-Dimethylbutanoyl)piperazin-1-ylsulfonyl)-4-(3,5-dimethylphenoxy)benzonitrile 59. HPLC purity: 92.2%; $^1$H NMR (500 MHz, CDCl$_3$): 8.27 (d, J=2 Hz, 1H), 7.67 (dd, $J_1$=9 Hz, $J_2$=2 Hz, 1H), 6.93 (s, 1H), 6.90 (d, J=9 Hz, 1H), 6.67 (s, 2H), 3.72 (m, 4H), 3.34 (m, 4H), 2.33 (s, 6H), 1.60 (m, 2H), 1.21 (s, 6H), 0.85 (t, J=7 Hz, 3H); MS (ESI, EI$^+$): m/z=470 (MH$^+$).

4-(3,5-Dimethylphenoxy)-3-(4-pivaloylpiperazin-1-ylsulfonyl)benzonitrile 63. HPLC purity: 98.8%; $^1$H NMR (500 MHz, CDCl$_3$): 8.27 (d, J=2 Hz, 1H), 7.67 (dd, $J_1$=9 Hz, $J_2$=2 Hz, 1H), 6.93 (s, 1H), 6.90 (d, J=9 Hz, 1H), 6.68 (s, 2H), 3.72 (m, 4H), 3.34 (m, 4H), 2.33 (s, 6H), 1.25 (s, 9H); MS (ESI, EI$^+$): m/z=456 (MH$^+$).

3-(4-(Cyclobutanecarbonyl)piperazin-1-ylsulfonyl)-4-(3,5-dimethylphenoxy)benzonitrile 64. HPLC purity: 97.4%; $^1$H NMR (500 MHz, CDCl$_3$): 8.26 (d, J=2 Hz, 1H), 7.67 (dd, $J_1$=9 Hz, $J_2$=2 Hz, 1H), 6.93 (s, 1H), 6.90 (d, J=9 Hz, 1H), 6.67 (s, 2H), 3.69 (m, 2H), 3.42 (m, 2H), 3.30 (m, 4H), 3.21 (m, 1H), 2.33 (s, 6H), 2.29 (m, 2H), 2.12 (m, 2H), 1.96 (m, 1H), 1.85 (m, 1H); MS (ESI, EI$^+$): m/z=454 (MH$^+$).

3-(4-(Cyclohexanecarbonyl)piperazin-1-ylsulfonyl)-4-(3,5-dimethylphenoxy)benzonitrile 65. HPLC purity: 97.9%; $^1$H NMR (500 MHz, CDCl$_3$): 8.27 (d, J=2 Hz, 1H), 7.67 (dd, $J_1$=9 Hz, $J_2$=2 Hz, 1H), 6.94 (s, 1H), 6.90 (d, J=9 Hz, 1H), 6.68 (s, 2H), 3.70 (m, 2H), 3.57 (m, 2H), 3.34 (m, 4H), 2.41 (m, 1H), 2.33 (s, 6H), 1.79 (m, 2H), 1.66 (m, 3H), 1.50 (m, 2H), 1.24 (m, 3H); MS (ESI, EI$^+$): m/z=482 (MH$^+$).

4-(3,5-Dimethylphenoxy)-3-(4-(3-methylbutanoyl)piperazin-1-ylsulfonyl)benzonitrile 66. HPLC purity: 100%; $^1$H NMR (500 MHz, CDCl$_3$): 8.27 (d, J=2 Hz, 1H), 7.67 (dd, $J_1$=9 Hz, $J_2$=2 Hz, 1H), 6.94 (s, 1H), 6.90 (d, J=9 Hz, 1H), 6.68 (s, 2H), 3.72 (m, 2H), 3.55 (m, 2H), 3.34 (m, 4H), 2.33 (s, 6H), 2.19 (d, J=7 Hz, 2H), 2.09 (m, 1H), 0.95 (d, J=7 Hz, 6H); MS (ESI, EI$^+$): m/z=456 (MH$^+$).

3-(4-(3,3-Dimethylbutanoyl)piperazin-1-ylsulfonyl)-4-(3,5-dimethylphenoxy)benzonitrile 67. HPLC purity: 98.5%; $^1$H NMR (500 MHz, CDCl$_3$): 8.27 (d, J=2 Hz, 1H), 7.67 (dd, $J_1$=9 Hz, $J_2$=2 Hz, 1H), 6.94 (s, 1H), 6.90 (d, J=9 Hz, 1H), 6.68 9s, 2H), 3.73 (m, 2H), 3.58 (m, 2H), 3.35 (m, 4H), 2.33 (s, 6H), 2.24 (s, 2H), 1.03 (s, 9H).

3-(4-(Cyclopentanecarbonyl)piperazin-1-ylsulfonyl)-4-(3,5-dimethylphenoxy)benzonitrile 68. HPLC purity: 95.3%; $^1$H NMR (500 MHz, CDCl$_3$): 8.27 (d, J=2 Hz, 1H), 7.67 (dd, $J_1$=9 Hz, $J_2$=2 Hz, 1H), 6.94 (s, 1H), 6.90 (d, J=9 Hz, 1H), 6.68 (s, 2H), 3.72 (m, 2H), 3.60 (m, 2H), 3.34 (m, 4H), 2.84 (m, 1H), 2.33 (s, 6H), 1.78 (m, 4H), 1.70 (m, 2H), 1.58 (m, 2H); MS (ESI, EI$^+$): m/z=468 (MH$^+$).

4-(3,5-Dichlorophenoxy)-3-(4-(4-(trifluoromethyl)benzoyl)piperazin-1-ylsulfonyl)benzonitrile 69. HPLC purity: 99.1%; $^1$H NMR (500 MHz, CDCl$_3$): 8.29 (d, J=2 Hz, 1H), 7.81 (dd, $J_1$=9 Hz, $J_2$=2 Hz, 1H), 7.70 (d, J=8 Hz, 2H), 7.50 (d, J=8 Hz, 2H), 7.30 (t, J=2 Hz, 1H), 7.04 (d, J=9 Hz, 1H), 6.98 (s, 2H), 3.89 (m, 2H), 3.48 (m, 4H), 3.29 (m, 2H); MS (ESI, EI$^+$): m/z=589 (MH$^+$).

3-(4-Benzoylpiperazin-1-ylsulfonyl)-4-(3,5-dichlorophenoxy)benzonitrile 70. HPLC purity: 96.8%; $^1$H NMR (500 MHz, CDCl$_3$): 8.29 (d, J=2 Hz, 1H), 7.80 (dd, $J_1$=9 Hz, $J_2$=2 Hz, 1H), 7.45 (m, 3H), 7.37 (m, 2H), 7.30 (s, 1H), 7.04 (d, J=9 Hz, 1H), 6.99 (s, 2H), 3.85 (m, 2H), 3.64 (m, 2H), 3.36 (m, 4H); MS (ESI, EI$^+$): m/z=517 (MH$^+$).

4-(3,5-Dichlorophenoxy)-3-(4-(3,3-dimethylbutanoyl)piperazin-1-ylsulfonyl)benzonitrile 71. HPLC purity: 99.3%; $^1$H NMR (500 MHz, CDCl$_3$): 8.30 (d, J=2 Hz, 1H), 7.80 (dd, J$_1$=9 Hz, J$_2$=2 Hz, 1H), 7.29 (s, 1H), 7.02 (d, J=9 Hz, 1H), 6.97 (s, 2H), 3.73 (m, 2H), 3.59 (m, 2H), 3.31 (m, 4H), 2.24 (s, 2H), 1.03 (s, 9H); MS (ESI, EI$^+$): m/z=511 (MH$^+$).

4-(3,5-Dichlorophenoxy)-3-(4-(3-methylbutanoyl)piperazin-1-ylsulfonyl)benzonitrile 72. HPLC purity: 99.1%; $^1$H NMR (500 MHz, CDCl$_3$): 8.30 (d, J=2 Hz, 1H), 7.80 (dd, J$_1$=9 Hz, J$_2$=2 Hz, 1H), 7.30 (t, J=2 Hz, 1H), 7.02 (d, J=9 Hz, 1H), 6.98 (d, J=2 Hz, 2H), 3.72 (m, 2H), 3.57 (m, 2H), 3.31 (m, 4H), 2.19 (d, J=7 Hz, 2H), 2.09 (m, 1H), 0.95 (d, J=7 Hz, 6H); MS (ESI, EI$^+$): m/z=497 (MH$^+$).

3-(4-(Cyclobutanecarbonyl)piperazin-1-ylsulfonyl)-4-(3,5-dichlorophenoxy)benzonitrile 73. HPLC purity: 96.6%; $^1$H NMR (500 MHz, CDCl$_3$): 8.29 (d, J=2 Hz, 1H), 7.79 (dd, J$_1$=8 Hz, J$_2$=2 Hz, 1H), 7.30 (t, J=2 Hz, 1H), 7.02 (d, J=9 Hz, 1H), 6.97 (d, J=2 Hz, 2H), 3.70 (m, 2H), 3.43 (m, 2H), 3.28 (m, 4H), 3.22 (m, 1H), 2.32 (m, 2H), 2.14 (m, 2H), 1.97 (m, 1H), 1.86 (m, 1H); MS (ESI, EI$^+$): m/z=495 (MH$^+$).

3-(4-(Cyclopentanecarbonyl)piperazin-1-ylsulfonyl)-4-(3,5-dichlorophenoxy)benzonitrile 74. HPLC purity: 97.5%; $^1$H NMR (500 MHz, CDCl$_3$): 8.30 (d, J=2 Hz, 1H), 7.80 (dd, J$_1$=8 Hz, J$_2$=2 Hz, 1H), 7.30 (t, J=2 Hz, 1H), 7.03 (d, J=9 Hz, 1H), 6.98 (d, J=2 Hz, 2H), 3.72 (m, 2H), 3.61 (m, 2H), 3.31 (m, 4H), 2.84 (m, 1H), 1.80 (m, 4H), 1.74 (m, 2H), 1.57 (m, 2H); MS (ESI, EI$^+$): m/z=509 (MH$^+$).

3-(4-(4-Chlorobenzoyl)piperazin-1-ylsulfonyl)-4-(3,5-dichlorophenoxy)benzonitrile 78. HPLC purity: 94.4%; $^1$H NMR (500 MHz, CDCl$_3$): 8.29 (d, J=2 Hz, 1H), 7.81 (dd, J$_1$=8 Hz, J$_2$=2 Hz, 1H), 7.40 (m, 2H), 7.33 (m, 2H), 7.30 (t, J=2 Hz, 1H), 7.04 (d, J=9 Hz, 1H), 6.98 (s, 2H), 3.70 (m, 4H), 3.35 (m, 4H); MS (ESI, EI$^+$): m/z=551 (MH$^+$).

3-(4-(3-Chlorobenzoyl)piperazin-1-ylsulfonyl)-4-(3,5-dichlorophenoxy)benzonitrile 81. HPLC purity: 92.5%; $^1$H NMR (500 MHz, CDCl$_3$): 8.30 (d, J=2 Hz, 1H), 7.81 (dd, J$_1$=9 Hz, J$_2$=2 Hz, 1H), 7.42 (m, 1H), 7.35 (m, 2H), 7.30 (t, J=2 Hz, 1H), 7.26 (m, 1H), 7.04 (d, J=9 Hz, 1H), 6.99 (d, J=2 Hz, 2H), 3.85 (m, 2H), 3.55 (m, 2H), 3.38 (m, 4H); MS (ESI, EI$^+$): m/z=551 (MH$^+$).

4-(3,5-Dichlorophenoxy)-3-(4-(4-methylbenzoyl)piperazin-1-ylsulfonyl)benzonitrile 82. HPLC purity: 91.7%; $^1$H NMR (500 MHz, CDCl$_3$): 8.29 (d, J=2 Hz, 1H), 7.80 (dd, J$_1$=9 Hz, J$_2$=2 Hz, 1H), 7.29 (m, 3H), 7.21 (d, J=8 Hz, 2H), 7.03 (d, J=9 Hz, 1H), 6.98 (d, J=2 Hz, 2H), 3.70 (m, 4H), 3.33 (m, 4H), 2.38 (s, 3H); MS (ESI, EI$^+$): m/z=531 (MH$^+$).

4-(3,5-Dichlorophenoxy)-3-(4-(2-methylbenzoyl)piperazin-1-ylsulfonyl)benzonitrile 83. HPLC purity: 90.1%; $^1$H NMR (500 MHz, CDCl$_3$): 8.29 (d, J=2 Hz, 1H), 7.80 (dd, J$_1$=9 Hz, J$_2$=2 Hz, 1H), 7.30 (m, 2H), 7.22 (m, 2H), 7.11 (d, J=7 Hz, 1H), 7.03 (d, J=9 Hz, 1H), 6.98 (d, J=2 Hz, 2H), 3.99 (m, 1H), 3.83 (m, 1H), 3.47 (m, 1H), 3.36 (m, 3H), 3.22 (m, 2H), 2.27 (s, 3H); MS (ESI, EI$^+$): m/z=531 (MH$^+$).

3-(4-(2-Chlorobenzoyl)piperazin-1-ylsulfonyl)-4-(3,5-dichlorophenoxy)benzonitrile 84. HPLC purity: 98.6%; $^1$H NMR (500 MHz, CDCl$_3$): 8.30 (d, J=2 Hz, 1H), 7.80 (dd, J$_1$=9 Hz, J$_2$=2 Hz, 1H), 7.41 (m, 1H), 7.35 (m, 3H), 7.26 (m, 1H), 7.02 (d, J=9 Hz, 1H), 6.99 (d, J=2 Hz, 2H), 4.11 (m, 1H), 3.73 (m, 1H), 3.53 (m, 1H), 3.33 (m, 5H); MS (ESI, EI$^+$): m/z=551 (MH$^+$).

4-(3,5-Dichlorophenoxy)-3-(4-(2-fluorobenzoyl)piperazin-1-ylsulfonyl)benzonitrile 85. HPLC purity: 98.6%; $^1$H NMR (500 MHz, CDCl$_3$): 8.30 (d, J=2 Hz, 1H), 7.80 (dd, J$_1$=9 Hz, J$_2$=2 Hz, 1H), 7.43 (m, 1H), 7.41 (m, 1H), 7.30 (s, 1H), 7.23 (m, 1H), 7.10 (t, J=9 Hz, 1H), 7.03 (d, J=9 Hz, 1H), 7.00 (d, J=2 Hz, 2H), 3.90 (m, 2H), 3.43 (m, 4H), 3.33 (m, 2H); MS (ESI, EI$^+$): m/z=535 (MH$^+$).

4-(3,5-Dichlorophenoxy)-3-(4-(3-fluorobenzoyl)piperazin-1-ylsulfonyl)benzonitrile 86. HPLC purity: 98%; $^1$H NMR (500 MHz, CDCl$_3$): 8.29 (d, J=2 Hz, 1H), 7.81 (dd, J$_1$=9 Hz, J$_2$=2 Hz, 1H), 7.41 (m, 1H), 7.30 (s, 1H), 7.16 (m, 2H), 7.09 (d, J=9 Hz, 1H), 7.04 (d, J=9 Hz, 1H), 6.99 (s, 2H), 3.85 (m, 2H), 3.55 (m, 2H), 3.36 (m, 4H); MS (ESI, EI$^+$): m/z=535 (MH$^+$).

4-(3,5-Dichlorophenoxy)-3-(4-(4-fluorobenzoyl)piperazin-1-ylsulfonyl)benzonitrile 87. HPLC purity: 98%; $^1$H NMR (500 MHz, CDCl$_3$): 8.29 (d, J=2 Hz, 1H), 7.81 (dd, J$_1$=9 Hz, J$_2$=2 Hz, 1H), 7.40 (m, 2H), 7.30 (s, 1H), 7.11 (t, J=9 Hz, 2H), 7.04 (d, J=9 Hz, 1H), 6.98 (s, 2H), 3.71 (m, 4H), 3.35 (m, 4H); MS (ESI, EI$^+$): m/z=535 (MH$^+$).

4-(3,5-Dimethylphenylthio)-3-(4-(4-(trifluoromethyl)benzoyl)piperazin-1-ylsulfonyl)benzonitrile 88. HPLC purity: 98.9%; $^1$H NMR (500 MHz, CDCl$_3$): 8.18 (d, J=2 Hz, 1H), 7.70 (d, J=8 Hz, 2H), 7.52 (d, J=8 Hz, 2H), 7.48 (dd, J$_1$=8 Hz, J$_2$=2 Hz, 1H), 7.15 (m, 3H), 6.95 (d, J=8 Hz, 1H), 3.92 (m, 2H), 3.54 (m, 2H), 3.48 (m, 2H), 3.36 (m, 2H), 2.36 (s, 6H); MS (ESI, EI$^+$): m/z=560 (MH$^+$).

3-(4-Benzoylpiperazin-1-ylsulfonyl)-4-(3,5-dimethylphenylthio)benzonitrile 89. HPLC purity: 98.7%; $^1$H NMR (500 MHz, CDCl$_3$): 8.18 (d, J=2 Hz, 1H), 7.47 (dd, J$_1$=9 Hz, J$_2$=2 Hz, 1H), 7.42 (m, 5H), 7.14 (s, 3H), 6.95 (d, J=8 Hz, 1H), 3.90 (m, 2H), 3.60 (m, 2H), 3.40 (m, 4H), 2.36 (s, 6H); MS (ESI, EI$^+$): m/z=492 (MH$^+$).

4-(3,5-Dimethylphenylthio)-3-(4-(4-methylbenzoyl)piperazin-1-ylsulfonyl)benzonitrile 90. $^1$H NMR (500 MHz, CDCl$_3$): 8.17 (d, J=2 Hz, 1H), 7.47 (dd, J$_1$=8 Hz, J$_2$=2 Hz, 1H), 7.29 (d, J=8 Hz, 2H), 7.22 (d, J=8 Hz, 1H), 7.15 (m, 3H), 6.94 (d, J=8 Hz, 1H), 3.77 (m, 4H), 3.39 (m, 4H), 2.37 (d, J=8 Hz, 9H); MS (ESI, EI$^+$): m/z=506 (MH$^+$).

4-(3,5-Dimethylphenylthio)-3-(4-(3-methylbenzoyl)piperazin-1-ylsulfonyl)benzonitrile 91. $^1$H NMR (500 MHz, CDCl$_3$): 8.18 (d, J=2 Hz, 1H), 7.47 (dd, J$_1$=9 Hz, J$_2$=2 Hz, 1H), 7.26 (m, 3H), 7.15 (m, 4H), 6.95 (d, J=8 Hz, 1H), 3.88 (m, 2H), 3.60 (m, 2H), 3.40 (m, 4H), 2.36 (s, 9H); MS (ESI, EI$^+$): m/z=506 (MH$^+$).

4-(3,5-Dimethylphenylthio)-3-(4-(2-methylbenzoyl)piperazin-1-ylsulfonyl)benzonitrile 92. $^1$H NMR (500 MHz, CDCl$_3$): 8.18 (d, J=2 Hz, 1H), 7.48 (dd, J$_1$=8 Hz, J$_2$=2 Hz, 1H), 7.29 (m, 1H), 7.23 (m, 2H), 7.14 (m, 4H), 6.96 (d, J=8 Hz, 1H), 4.02 (m, 1H), 3.87 (m, 1H), 3.52 (m, 1H), 3.37 (m, 4H), 3.26 (m, 1H), 2.36 (s, 6H), 2.29 (s, 3H); MS (ESI, EI$^+$): m/z=506 (MH$^+$).

Example 2

Preparation of 4-(5-cyano-2-(3,5-dimethylphenoxy)phenylsulfonyl)-N-isopropylpiperazine-1-carboxamide 58

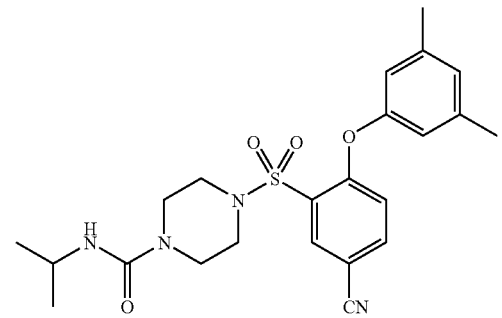

58

Compound 58 was synthesized as shown in Scheme 3.
4-(5-Cyano-2-(3,5-dimethylphenoxy)phenylsulfonyl)-N-isopropylpiperazine-1-carboxamide 58. To a solution of compound 24 (0.100 g, 0.27 mmol) in CH$_2$Cl$_2$ (3 mL) was added isopropyl isocyanate (0.032 g, 0.38 mmol) and triethylamine (0.039 g, 0.38 mmol). Reaction was stirred for 20 hrs at room temperature, whereupon the starting material was consumed (TLC, 1% MeOH in CH$_2$Cl$_2$). The reaction mixture was then concentrated in vacuo, redissolved in a minimal amount of CH$_2$Cl$_2$, and chromatographed over normal phase silica (MeOH/CH$_2$Cl$_2$). The fractions containing the desired product were combined and concentrated in vacuo to yield a white powder, which was then triturated with CH$_2$Cl$_2$/hexanes and vacuum filtered to yield a powder. The powder was redissolved in CH$_2$Cl$_2$ and chromatographed for a second time over normal phase silica (MeOH/CH$_2$Cl$_2$). The fractions containing the desired product were combined and concentrated in vacuo to yield a white powder, which was then triturated with hexanes and vacuum filtered to afford compound 58 as a white powder (0.014 g, 11.3% yield, 99.1% HPLC purity). $^1$H NMR (500 MHz, CDCl$_3$): 8.27 (d, J=2 Hz, 1H), 7.67 (dd, J$_1$=9 Hz, J$_2$=2 Hz, 1H) 6.93 (s, 1H), 6.89 (s, J=9 Hz, 1H), 6.69 (s, 2H), 4.17 (m, 1H), 3.95 (m, 1H), 3.44 (m, 4H), 3.35 (m, 4H), 2.34 (s, 6H), 1.14 (d, J=7 Hz, 6H); MS (ESI, EI$^+$): m/z=457 (MH$^+$).

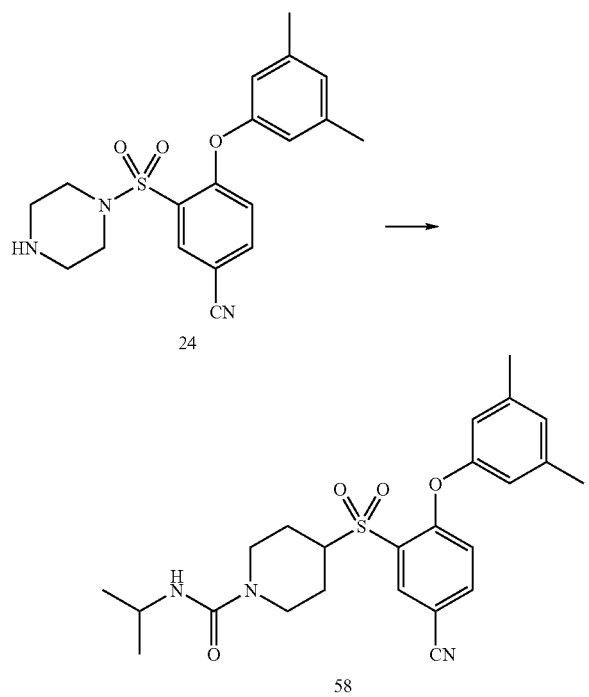

The following compounds were made according to the procedures as described in this example.

4-(5-Cyano-2-(3,5-dimethylphenoxy)phenylsulfonyl)-N-(3-fluorophenyl)piperazine-1-carboxamide 61. HPLC purity: 99.2%; $^1$H NMR (500 MHz, CDCl$_3$): 8.28 (d, J=2 Hz, 1H), 7.68 (dd, J$_1$=9 Hz, J$_2$=2 Hz, 1H), 7.25 (m, 1H), 7.20 (m, 1H), 6.97 (dd, J$_1$=8 Hz, J$_2$=2 Hz, 1H), 6.94 (s, 1H), 6.91 (d, J=9 Hz, 1H), 6.74 (m, 1H), 6.70 (s, 2H), 6.43 (s, 1H), 3.59 (m, 4H), 3.42 (m, 4H), 2.33 (s, 6H); MS (ESI, EI$^+$): m/z=509 (MH$^+$).

4-(5-Cyano-2-(3,5-dimethylphenoxy)phenylsulfonyl)-N-(4-ethylphenyl)piperazine-1-carboxamide 62. HPLC purity: 98.7%; $^1$H NMR (500 MHz, CDCl$_3$): 8.28 (d, J=2 Hz, 1H), 7.68 (dd, J$_1$=9 Hz, J$_2$=2 Hz, 1H), 7.20 (m, 2H), 7.11 (d, J=8 Hz, 2H), 6.93 (s, 1H), 6.90 (d, J=9 Hz, 1H), 6.70 (s, 2H), 6.28 (s, 1H), 3.57 (m, 4H), 3.41 (m, 4H), 2.59 (q, J$_1$=15 Hz, J$_2$=8 Hz, 2H), 2.33 (s, 6H), 1.20 (t, J=8 Hz, 3H); MS (ESI, EI$^+$): m/z=519 (MH$^+$).

4-(5-Cyano-2-(3,5-dichlorophenoxy)phenylsulfonyl)-N-(3-fluorophenyl)piperazine-1-carboxamide 75. HPLC purity: 97%; $^1$H NMR (500 MHz, CDCl$_3$): 8.31 (d, J=2 Hz, 1H), 7.80 (dd, J$_1$=9 Hz, J$_2$=2 Hz, 1H) 7.30 (t, J=2 Hz, 1H), 7.27 (m, 1H), 7.23 (m, 1H), 7.03 (d, J=9 Hz, 1H), 7.00 (d, J=2 Hz, 2H), 6.97 (m, 1H), 6.75 (m, 1H), 6.37 (s, 1H), 3.61 (m, 4H), 3.40 (m, 4H); MS (ESI, EI+): m/z=550 (MH$^+$).

4-(5-Cyano-2-(3,5-dichlorophenoxy)phenylsulfonyl)-N-isopropylpiperazine-1-carboxamide 80. HPLC purity: 99.4%; $^1$H NMR (500 MHz, CDCl$_3$): 8.30 (d, J=2 Hz, 1H), 7.79 (dd, J$_1$=9 Hz, J$_2$=2 Hz, 1H), 7.29 (t, J=2 Hz, 1H), 7.02 (d, J=9 Hz, 1H), 6.98 (d, J=2 Hz, 2H), 4.18 (d, J=7 Hz, 1H), 3.95 (m, 1H), 3.45 (m, 4H), 3.32 (m, 4H), 1.15 (d, J=7 Hz, 6H); MS (ESI, EI$^+$): m/z=498 (MH$^+$).

Ethyl 4-(5-cyano-2-(3,5-dichlorophenylthio)phenylsulfonyl)piperazine-1-carboxylate 94. $^1$H NMR (500 MHz, CDCl$_3$): 8.29 (d, J=2 Hz, 1H), 7.79 (dd, J$_1$=9 Hz, J$_2$=2 Hz, 1H), 7.29 (t, 2 Hz, 1H), 7.02 (d, J=9 Hz, 1H), 6.98 (s, 2H), 4.14 (m, 2H), 3.57 (m, 4H), 3.30 (m, 4H), 1.25 (t, J=7 Hz, 3H); MS (ESI, EI+): m/z=525 (MH$^+$).

Example 3

Preparation of 4-(3,5-dimethylphenoxy)-3-(4-(4-(trifluoromethyl)phenylsulfonyl)piperazin-1-ylsulfonyl)benzonitrile 60

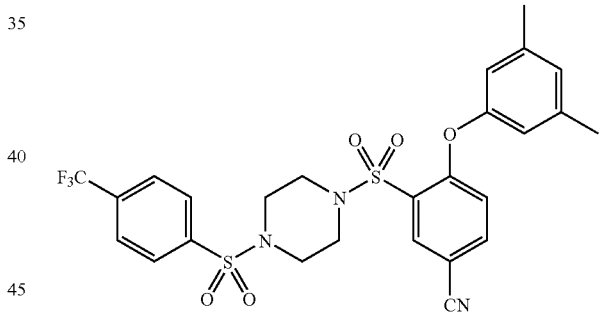

Compound 60 was synthesized as shown in Scheme 4.

4-(3,5-Dimethylphenoxy)-3-(4-(4-(trifluoromethyl)phenylsulfonyl)piperazin-1-ylsulfonyl)benzonitrile 60. To a solution of compound 24 (0.099 g, 0.27 mmol) in CH$_2$Cl$_2$ (3 mL) was added 4-(trifluoromethyl)benzenesulfonyl chloride (0.093 g, 0.38 mmol) and triethylamine (0.039 g, 0.38 mmol). The reaction mixture was stirred for 18 hrs, whereupon the starting material was consumed (TLC, 1% MeOH in CH$_2$Cl$_2$). The reaction mixture was then concentrated in vacuo, redissolved in a minimal amount of CH$_2$Cl$_2$, and chromatographed over normal phase silica (MeOH/CH$_2$Cl$_2$). The fractions containing the desired product were combined and concentrated in vacuo to yield a white solid. The solid was triturated with diisopropyl ether/hexanes and vacuum filtered to afford compound 60 as a white powder. (0.065 g, 42.2% yield, 95.7% HPLC purity). $^1$H NMR (500 MHz, CDCl$_3$): 8.23 (d, J=2 Hz, 1H), 7.86 (m, 4H), 7.67 (dd, J$_1$=9 Hz, J$_2$=2 Hz, 1H), 6.95 (s, 1H), 6.89 (d, J=9 Hz, 1H), 6.68 (s, 2H), 3.48 (m, 4H), 3.15 (m, 4H), 2.35 (s, 6H); MS (ESI, EI$^+$): m/z=580 (MH$^+$).

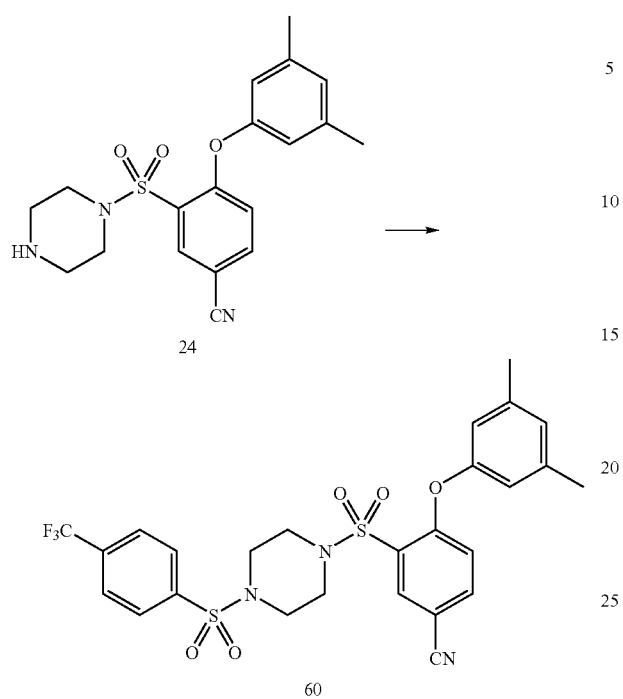

Scheme 4

The following compounds were made according to the procedures as described in this example.

3-(4-((7,7-Dimethylbicyclo[2.2.1]heptan-1-yl)methylsulfonyl)piperazin-1-ylsulfonyl)-4-(3,5-dimethylphenoxy)benzonitrile 51. HPLC purity: 99.3%; ¹H NMR (500 MHz, CDCl₃): δ 8.27 (d, J=2 Hz, 1H), 7.68 (dd, J₁=9 Hz, J₂=2 Hz, 1H), 6.94 (s, 1H), 6.90 (d, J=9 Hz, 1H), 6.71 (s, 2H), 3.43 (m, 5H), 3.32 (d, J=15 Hz, 1H), 2.75 (d, J=15 Hz, 1H), 2.41 (m, 4H), 2.34 (s, 6H), 2.12 (t, J=4 Hz, 1H), 2.05 (m, 1H), 1.94 (d, J=19 Hz, 1H), 1.63 (m, 1H), 1.56 (s, 1H), 1.43 (m, 1H), 1.10 (s, 3H), 0.87 (s, 3H); MS (ESI, EI⁺): m/z=586 (MH⁺).

4-(3,5-Dimethylphenoxy)-3-(4-(methylsulfonyl)piperazin-1-ylsulfonyl)benzonitrile 52. HPLC purity: 97.2%; ¹H NMR (500 MHz, DMSO-d₆): δ 8.25 (d, J=2 Hz, 1H), 8.04 (dd, J₁=9 Hz, J₂=2 Hz, 1H), 7.00 (d, J=9 Hz, 1H), 6.98 (s, 1H), 6.87 (s, 2H), 3.36 (t, J=4 Hz, 4H), 3.19 (t, J=5 Hz, 4H), 2.90 (s, 3H), 2.30 (s, 6H); MS (ESI, EI⁺): m/z=450 (MH⁺).

4-(3,5-Dimethylphenoxy)-3-(4-tosylpiperazin-1-ylsulfonyl)benzonitrile 53. HPLC purity: 98.2%; ¹H NMR (500 MHz, DMSO-d₆): δ 8.19 (d, J=2 Hz, 1H), 8.01 (dd, J₁=9 Hz, J₂=2 Hz, 1H), 7.60 (d, J=8 Hz, 2H), 7.45 (d, J=8 Hz, 2H), 6.94 (d, J=9 Hz, 2H), 6.77 (s, 2H), 3.35 (m, 4H), 2.92 (m, 4H), 2.41 (s, 3H), 2.29 (s, 6H); MS (ESI, EI⁺): m/z=526 (MH⁺).

4-(3,5-Dimethylphenoxy)-3-(4-(isobutylsulfonyl)piperazin-1-ylsulfonyl)benzonitrile 56. HPLC purity: 97.9%; ¹H NMR (500 MHz, CDCl₃): 8.26 (d, J=2 Hz, 1H), 7.68 (dd, J₁=9 Hz, J₂=2 Hz, 1H), 6.94 (s, 1H), 6.90 (d, J=9 Hz, 1H), 6.70 (s, 2H), 3.46 (m, 4H), 3.35 (m, 4H), 2.75 (d, J=7 Hz, 2H), 2.34 (s, 6H), 2.28 (m, 1H), 1.11 (s, J=7 Hz, 6H); MS (ESI, EI⁺): m/z=492 (MH⁺).

4-(3,5-Dichlorophenoxy)-3-(4-(methylsulfonyl)piperazin-1-ylsulfonyl)benzonitrile 76. HPLC purity: 88.5%; ¹H NMR (500 MHz, CDCl₃): 8.30 (d, J=2 Hz, 1H), 7.81 (dd, J₁=9 Hz, J₂=2 Hz, 1H), 7.31 (s, 1H), 7.03 (d, J=9 Hz, 1H), 7.00 (d, J=2 Hz, 2H), 3.46 (m, 4H), 3.35 (m, 4H), 2.82 (s, 3H); MS (ESI, EI⁺): m/z=491 (MH⁺).

4-(3,5-Dichlorophenoxy)-3-(4-tosylpiperazin-1-ylsulfonyl)benzonitrile 77. HPLC purity: 91.7%; ¹H NMR (500 MHz, CDCl₃): 8.25 (d, J=2 Hz, 1H), 7.78 (dd, J₁=9 Hz, J₂=2 Hz, 1H), 7.61 (d, J=8 Hz, 2H), 7.36 (d, J=8 Hz, 2H), 7.30 (t, J=2 Hz, 1H), 7.00 (d, J=9 Hz, 1H), 6.97 (d J=2 Hz, 2H), 3.43 (m, 4H), 3.09 (m, 4H), 2.46 (s, 3H); MS (ESI, EI⁺): m/z=567 (MH⁺).

4-(3,5-Dichlorophenoxy)-3-(4-(3-methylbenzoyl)piperazin-1-ylsulfonyl)benzonitrile 79. HPLC purity: 90.2%; ¹H NMR (500 MHz, CDCl₃): 8.29 (d, J=2 Hz, 1H), 7.80 (dd, J₁=9 Hz, J₂=2 Hz, 1H), 7.30 (m, 1H), 7.25 (m, 2H), 7.19 (s, 1H) 7.14 (d, J=7 Hz, 1H), 7.04 (d, J=9 Hz, 1H), 6.99 (d, J=2 Hz, 2H), 3.85 (m, 2H), 3.57 (m, 2H), 3.36 (m, 4H), 2.37 (s, 3H); MS (ESI, EI⁺): m/z=531 (MH⁺).

4-(3,5-Dimethylphenylthio)-3-(4-(3-fluorobenzoyl)piperazin-1-ylsulfonyl)benzonitrile 93. ¹H NMR (500 MHz, CDCl₃): 8.18 (d, J=2 Hz, 1H), 7.48 (dd, J₁=8 Hz, J₂=2 Hz, 1H), 7.28 (s, 1H), 7.23 (m, 1H), 7.14 (s, 3H), 6.98 (m, 1H), 6.94 (d, J=8 Hz, 1H), 6.75 (m, 1H), 6.42 (s, 1H), 3.64 (m, 4H), 3.44 (m, 4H), 2.36 (s, 6H); MS (ESI, EI⁺): m/z=525 (MH⁺).

Example 4

Preparation of 1-(2-(2,5-dichlorophenoxy)-5-nitrophenylsulfonyl)piperazine

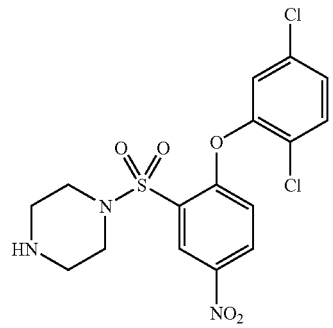

Compound 40 was synthesized as shown in Scheme 5.

Scheme 5

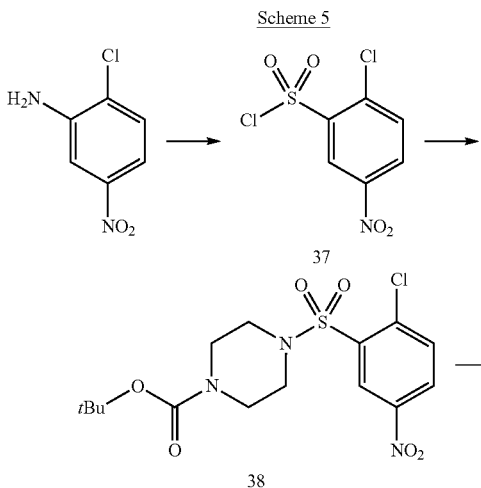

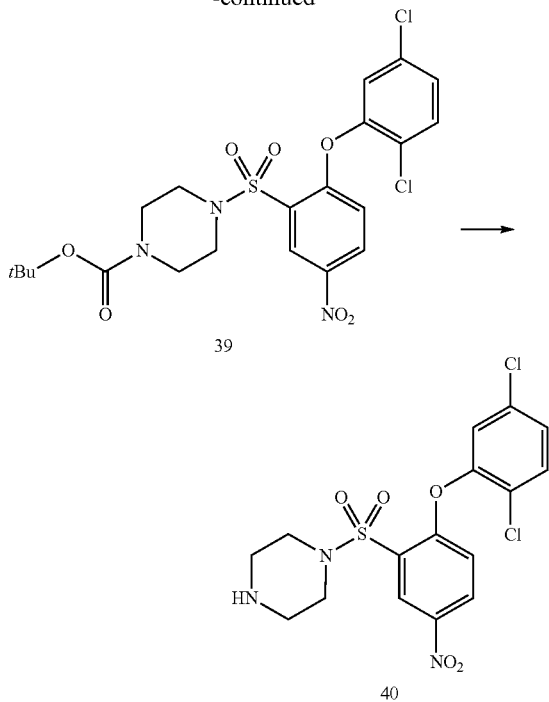

2-Chloro-5-nitrobenzene-1-sulfonyl chloride 37. To an ice-bath chilled solution of conc. HCl (100 mL) was added 2-chloro-5-nitroaniline (10 g) portion-wise. When complete dissolution was achieved, an aqueous solution of sodium nitrite (6.0 g in 50 mL water) was added dropwise and the resulting reaction mixture was stirred at 0° C. for 1 hr. The above obtained diazonium ion solution was then carefully added to an ice-bath chilled mixture of cupric chloride dihydrate (5 g) in acetic acid (500 mL) pre-saturated with sulfur dioxide gas. After stirring the resulting reaction mixture at 0° C. for 1 hr, it was carefully added portion-wise to an ice-water slurry with vigorous stirring. The separated solids were collected by suction, rinsed with water, and dried under vacuum to furnish the desired product 37 as a cream colored powder (8.2 g, 55%). $^1$H NMR (500 MHz, DMSO-d$_6$): δ 8.61 (d, J=3 Hz, 1H), 8.16 (dd, J$_1$=9 Hz, J$_2$=3 Hz, 1H), 7.70 (d, J=9 Hz, 1H).

Tert-butyl 4-(2-chloro-5-nitrophenylsulfonyl)piperazine-1-carboxylate 38. A solution of compound 37 (0.600 g, 2.34 mmol) in DCM (20.00 mL) was added tert-butyl 1-piperazinecarboxylate (0.566 g, 3.04 mmol) and TEA (0.422 mL, 3.04 mmol). The reaction was monitored with TLC (25% EtOAc in hexanes, R$_f$=0.53). The reaction mixture was complete after stirring at room temperature for 1 hr, as indicated by the absence of the starting material (TLC). Water was added and aqueous layer was extracted twice with DCM. Combined extracts were sequentially washed with water and brine, dried over MgSO$_4$, filtered, and evaporated in vacuo to afford a yellow solid. The solid was triturated with DCM and hexanes, and then filtered to yield compound 38 as a yellow solid (0.789 g, 100% HPLC purity, 83% yield). $^1$H NMR (500 MHz, DMSO-d$_6$): δ 8.60 (d, J=3 Hz, 1H), 8.47 (dd, J$_1$=3 Hz, J$_2$=8 Hz, 1H), 8.01 (d, J=8 Hz, 1H), 3.37 (m, 4H), 3.23 (m, 4H), 1.37 (s, 9H).

Tert-butyl 4-(2-(2,5-dichlorophenoxy)-5-nitrophenylsulfonyl)piperazine-1-carboxylate 39. To a solution of 2,5-dichlorophenol (0.414 g, 2.54 mmol) in THF (20.00 mL) stirred in an ice bath was added NaH (0.101 g, 2.54 mmol) slowly. After addition, the mixture was stirred for 5 min. Compound 38 (0.790 g, 1.95 mmol) was then added and the resulting reaction mixture was heated to 75° C. overnight. The reaction was monitored by HPLC. However, the reaction was not complete after 16 hrs (HPLC), so THF was evaporated and 18-crown-6 (1.057 g, 4.00 mmol), DMF (15 mL), and K$_2$CO$_3$ (0.553 g, 4.00 mmol) were added. The reaction mixture was heated to 100° C. for another 16 hrs, at which time HPLC indicated that the reaction was complete by absence of starting material. The reaction mixture was cooled to room temperature, and water (0.250 mL) was added. The reaction mixture was extracted thrice with EtOAc. Combined extracts were washed sequentially with 1N NaOH, water, and brine, dried over MgSO$_4$, filtered, and evaporated in vacuo. The residual was dissolved in a minimal amount of DCM and purified with chromatography using a gradient of 5 to 30% EtOAc in hexanes. Pure fractions were combined and evaporated in vacuo. The resulting solid was triturated with DCM and hexanes, and then filtered to afford compound 39 as a white/yellow powder (0.120 g, 100% HPLC purity, 10.0% yield). $^1$H NMR (500 MHz, DMSO-d$_6$): δ 8.59 (d, J=2 Hz, 1H), 8.42 (dd, J$_1$=2 Hz, J$_2$=8 Hz, 1H), 7.76 (d, J=8 Hz, 1H), 7.66 (d, J=3 Hz, 1H), 7.50 (dd, J$_1$=2 Hz, J$_2$=8 Hz, 1H), 7.10 (d, J=8 Hz, 1H), 3.40 (m, 4H), 3.25 (m, 4H), 1.37 (s, 9H).

1-(2-(2,5-Dichlorophenoxy)-5-nitrophenylsulfonyl)piperazine 40. To a solution of compound 39 (0.100 g, 0.19 mmol) in DCM (6.00 mL) was added 1N HCl in 1,4-dioxane (0.570 mL). The reaction was monitored with TLC (25% EtOAc in hexanes, R$_f$=0.0). The reaction was complete after stirring at room temperature for 16 hrs, as indicated by the absence of the starting material). The reaction mixture was concentrated and the residual was redissolved in MeOH (2.00 mL). Et$_2$O (4.00 mL) was then added and the mixture was stirred until precipitate formed (10 min). The solid was collected by filtration to yield compound 40 as a white solid (0.080 g, 100% HPLC purity, 83% yield). $^1$H NMR (500 MHz, DMSO-d$_6$): δ 9.39 (s, 2H), 8.61 (d, J=2 Hz, 1H), 8.45 (dd, J$_1$=3 Hz, J$_2$=9 Hz, 1H), 7.78 (d, J=9 Hz, 1H), 7.73 (d, J=2 Hz, 1H), 7.53 (dd, J$_1$=2 Hz, J$_2$=8 Hz, 1H), 7.12 (d, J=8 Hz, 1H), 3.57 (m, 4H), 3.16 (m, 4H).

The following compounds were made according to the procedures as described in this example, and followed by modification as described herein, e.g., in Examples 1 to 3.

1-(4-(2-(2,5-Dichlorophenylthio)-5-nitrophenylsulfonyl)piperazin-1-yl)ethanone 151. HPLC purity: 99.5%; $^1$H NMR (500 MHz, DMSO-d$_6$): δ 8.51 (d, J=2 Hz, 1H), 8.28 (dd, J$_1$=2 Hz, J$_2$=8 Hz, 1H), 8.00 (d, J=2 Hz, 1H), 7.81 (d, J=8 Hz, 1H), 7.74 (dd, J$_1$=2 Hz, J$_2$=8 Hz, 1H), 7.01 (d, J=8 Hz, 1H), 3.54 (m, 4H), 3.35 (m, 2H), 3.25 (m, 2H), 1.99 (s, 3H); melting point: 190-193° C.

1-(4-(2-(2,5-Dichlorophenylthio)-5-nitrophenylsulfonyl)piperazin-1-yl)-3-methylbutan-1-one 152. HPLC purity: 100%; $^1$H NMR (500 MHz, DMSO-d$_6$): δ 8.51 (d, J=2 Hz, 1H), 8.28 (dd, J$_1$=2 Hz, J$_2$=8 Hz, 1H), 8.00 (d, J=2 Hz, 1H), 7.81 (d, J=8 Hz, 1H), 7.74 (dd, J$_1$=2 Hz, J$_2$=8 Hz, 1H), 7.01 (d, J=8 Hz, 1H), 3.57 (m, 4H), 3.34 (m, 2H), 3.25 (m, 2H), 2.17 (d, J=8 Hz, 2H), 1.93 (m, 1H), 0.86 (d, J=8 Hz, 6H); melting point: 180-183° C.

(4-(2-(2,5-Dichlorophenylthio)-5-nitrophenylsulfonyl)piperazin-1-yl)(4-(trifluoromethyl)phenyl)methanone 153. HPLC purity: 100%; $^1$H NMR (500 MHz, DMSO-d$_6$): δ 8.51 (d, J=2 Hz, 1H), 8.30 (dd, J$_1$=2 Hz, J$_2$=8 Hz, 1H), 8.01 (d, J=2 Hz, 1H), 7.83 (s, 1H), 7.80 (d, J=8 Hz, 2H), 7.74 (dd, J$_1$=2 Hz, J$_2$=8 Hz, 1H), 7.62 (d, J=8 Hz, 2H), 7.03 (d, J=8 Hz, 1H), 3.75 (m, 2H), 3.35-3.40 (m, 6H); melting point: 190-193° C.

4-Chloro-1-(4-(2-(2,5-dichlorophenylthio)-5-nitrophenylsulfonyl)piperazin-1-yl)butan-1-one 160. HPLC purity:

98.5%; $^1$H NMR (500 MHz, DMSO-$d_6$): δ 8.51 (d, J=2 Hz, 1H), 8.28 (dd, $J_1$=2 Hz, $J_2$=8 Hz, 1H), 8.00 (d, J=2 Hz, 1H), 7.81 (d, J=8 Hz, 1H), 7.74 (dd, $J_1$=2 Hz, $J_2$=8 Hz, 1H), 7.01 (d, J=8 Hz, 1H), 3.63 (t, J=8 Hz, 2H), 3.56 (m, 4H), 3.33 (m, 2H), 3.27 (m, 2H), 2.45 (m, 2H), 1.91 (m, 2H); melting point: 179-182° C.

Cyclobutyl(4-(2-(2,5-dichlorophenylthio)-5-nitrophenylsulfonyl)piperazin-1-yl)methanone 161. HPLC purity: 99.6%; $^1$H NMR (500 MHz, DMSO-$d_6$): δ 8.50 (d, J=2 Hz, 1H), 8.28 (dd, $J_1$=2 Hz, $J_2$=8 Hz, 1H), 7.99 (d, J=2 Hz, 1H), 7.81 (d, J=8 Hz, 1H), 7.73 (dd, $J_1$=2 Hz, $J_2$=8 Hz, 1H), 7.01 (d, J=8 Hz, 1H), 3.54 (m, 2H), 3.42 (m, 2H), 3.24-3.31 (m, 5H), 2.12 (m, 2H), 2.06 (m, 2H), 1.85 (m, 1H), 1.69 (m, 1H); melting point: 189-192° C.

Cyclohexyl(4-(2-(2,5-dichlorophenylthio)-5-nitrophenylsulfonyl)piperazin-1-yl)methanone 162. HPLC purity: 99.3%; $^1$H NMR (500 MHz, DMSO-$d_6$): δ 8.51 (d, J=2 Hz, 1H), 8.28 (dd, $J_1$=2 Hz, $J_2$=8 Hz, 1H), 8.00 (d, J=2 Hz, 1H), 7.80 (d, J=8 Hz, 1H), 7.73 (dd, $J_1$=2 Hz, $J_2$=8 Hz, 1H), 7.01 (d, J=8 Hz, 1H), 3.59 (m, 4H), 3.25 (m, 2H), 2.53 (m, 1H), 1.65 (m, 2H), 1.59 (m, 3H), 1.25 (m, 4H), 1.13 (m, 1H); melting point: 207-210° C.

(4-(2-(2,5-Dichlorophenylthio)-5-nitrophenylsulfonyl)piperazin-1-yl)(phenyl)methanone 163. HPLC purity: 99%; $^1$H NMR (500 MHz, DMSO-$d_6$): δ 8.51 (d, J=2 Hz, 1H), 8.29 (dd, $J_1$=2 Hz, $J_2$=8 Hz, 1H), 8.02 (d, J=2 Hz, 1H), 7.82 (d, J=8 Hz, 1H), 7.74 (dd, $J_1$=2 Hz, $J_2$=8 Hz, 1H), 7.44 (m, 3H), 7.39 (m, 2H), 7.02 (d, J=8 Hz, 1H), 3.72 (m, 2H), 3.38 (m, 6H).

(4-Chlorophenyl)(4-(2-(2,5-dichlorophenylthio)-5-nitrophenylsulfonyl)-piperazin-1-yl)methanone 164. HPLC purity: 100%; $^1$H NMR (500 MHz, DMSO-$d_6$): δ 8.51 (d, J=2 Hz, 1H), 8.29 (dd, $J_1$=2 Hz, $J_2$=8 Hz, 1H), 8.01 (d, J=2 Hz, 1H), 7.82 (d, J=8 Hz, 1H), 7.74 (dd, $J_1$=2 Hz, $J_2$=8 Hz, 1H), 7.48 (d, J=8 Hz, 2H), 7.42 (d, J=8 Hz, 2H), 7.02 (d, J=8 Hz, 1H), 3.71 (m, 2H), 3.37 (m, 6H); melting point: 172-175° C.

(4-Methoxyphenyl)(4-(2-(2,5-dichlorophenylthio)-5-nitrophenylsulfonyl)-piperazin-1-yl)methanone 165. HPLC purity: 100%; $^1$H NMR (500 MHz, DMSO-$d_6$): δ 8.51 (d, J=2 Hz, 1H), 8.29 (dd, $J_1$=2 Hz, $J_2$=8 Hz, 1H), 8.02 (d, J=2 Hz, 1H), 7.82 (d, J=8 Hz, 1H), 7.74 (dd, $J_1$=2 Hz, $J_2$=8 Hz, 1H), 7.35 (d, J=8 Hz, 1H), 7.02 (d, J=8 Hz, 1H), 6.95 (d, J=8 Hz, 2H), 3.78 (s, 3H), 3.60 (m, 4H), 3.37 (m, 4H); melting point: 185-188° C.

(4-(2-(2,5-Dichlorophenylthio)-5-nitrophenylsulfonyl)piperazin-1-yl)(furan-2-yl)methanone 166. HPLC purity: 99%; $^1$H NMR (500 MHz, DMSO-$d_6$): δ 8.52 (d, J=2 Hz, 1H), 8.28 (dd, $J_1$=2 Hz, $J_2$=8 Hz, 1H), 8.02 (d, J=2 Hz, 1H), 7.82 (d, J=2 Hz, 1H), 7.80 (s, 1H), 7.73 (dd, $J_1$=2 Hz, $J_2$=8 Hz, 1H), 7.00 (m, 2H), 6.62 (m, 1H), 3.78 (m, 4H), 3.40 (m, 4H); melting point: 199-202° C.

1-(4-(2-(2,5-Dimethylphenylthio)-5-nitrophenylsulfonyl)piperazin-1-yl)ethanone 167. HPLC purity: 99%; $^1$H NMR (500 MHz, DMSO-$d_6$): δ 8.50 (d, J=2 Hz, 1H), 8.26 (dd, $J_1$=2 Hz, $J_2$=8 Hz, 1H), 7.47 (s, 1H), 7.41 (d, J=8 Hz, 1H), 7.35 (d, J=8 Hz, 1H), 6.81 (d, J=8 Hz, 1H), 3.55 (m, 4H), 3.35 (m, 2H), 3.24 (m, 2H), 2.32 (s, 3H), 2.24 (s, 3H), 2.00 (s, 3H); melting point: 151-153° C.

(4-(2-(2,5-Dimethylphenylthio)-5-nitrophenylsulfonyl)piperazin-1-yl)(4-(trifluoromethyl)phenyl)methanone 168. HPLC purity: 99%; $^1$H NMR (500 MHz, DMSO-$d_6$): δ 8.50 (d, J=2 Hz, 1H), 8.27 (dd, $J_1$=2 Hz, $J_2$=8 Hz, 1H), 7.81 (d, J=8 Hz, 2H), 7.63 (d, J=8 Hz, 2H), 7.48 (s, 1H), 7.42 (d, J=8 Hz, 1H), 7.36 (d, J=8 Hz, 1H), 6.82 (d, J=8 Hz, 1H), 3.76 (m, 2H), 3.35-3.41 (m, 6H), 2.33 (s, 3H), 2.26 (s, 3H); melting point: 200-203° C.

1-(4-(2-(2,5-Dimethylphenylthio)-5-nitrophenylsulfonyl)piperazin-1-yl)-3-methylbutan-1-one 169. HPLC purity: 99%; $^1$H NMR (500 MHz, DMSO-$d_6$): δ 8.50 (d, J=2 Hz, 1H), 8.25 (dd, $J_1$=2 Hz, $J_2$=8 Hz, 1H), 7.47 (s, 1H), 7.42 (d, J=8 Hz, 1H), 7.35 (d, J=8 Hz, 1H), 6.81 (d, J=8 Hz, 1H), 3.57 (m, 4H), 3.32 (m, 2H), 3.25 (m, 2H), 2.32 (s, 3H), 2.23 (s, 3H), 2.19 (d, J=8 Hz, 2H), 1.94 (m, 1H), 0.87 (d, J=8 Hz, 6H); melting point: 157-160° C.

4-Chloro-1-(4-(2-(2,5-dimethylphenylthio)-5-nitrophenylsulfonyl)piperazin-1-yl)butan-1-one 170. HPLC purity: 99%; $^1$H NMR (500 MHz, DMSO-$d_6$): δ 8.50 (d, J=2 Hz, 1H), 8.26 (dd, $J_1$=2 Hz, $J_2$=8 Hz, 1H), 7.47 (s, 1H), 7.41 (d, J=8 Hz, 1H), 7.35 (d, J=8 Hz, 1H), 6.81 (d, J=8 Hz, 1H), 3.64 (t, $J_1$=$J_2$=7 Hz, 2H), 3.57 (m, 4H), 3.33 (m, 2H), 3.27 (m, 2H), 2.46 (t, $J_1$=$J_2$=7 Hz, 2H), 2.32 (s, 3H), 2.24 (s, 3H), 1.93 (m, 2H); melting point: 156-159° C.

Cyclohexyl(4-(2-(2,5-dimethylphenylthio)-5-nitrophenylsulfonyl)piperazin-1-yl)methanone 171. HPLC purity: 100%; $^1$H NMR (500 MHz, DMSO-$d_6$): δ 8.50 (d, J=2 Hz, 1H), 8.26 (dd, $J_1$=2 Hz, $J_2$=8 Hz, 1H), 7.47 (s, 1H), 7.42 (d, J=8 Hz, 1H), 7.35 (d, J=8 Hz, 1H), 6.81 (d, J=8 Hz, 1H), 3.62 (s, 2H), 3.55 (s, 2H), 3.24 (s, 2H), 2.56 (m, 1H), 2.32 (s, 3H), 2.23 (s, 3H), 1.67 (m, 2H), 1.59 (m, 3H), 1.27 (m, 4H), 1.12 (m, 1H); melting point: 170-173° C.

(4-(2-(2,5-Dimethylphenylthio)-5-nitrophenylsulfonyl)piperazin-1-yl)(phenyl)methanone 172. HPLC purity: 99.9%; $^1$H NMR (500 MHz, DMSO-$d_6$): δ 8.50 (d, J=2 Hz, 1H), 8.27 (dd, $J_1$=2 Hz, $J_2$=8 Hz, 1H), 7.35-7.48 (m, 8H), 6.82 (d, J=8 Hz, 1H), 3.70 (m, 2H), 3.38 (m, 6H), 2.33 (s, 3H), 2.25 (s, 3H); melting point: 190-193° C.

(4-Chlorophenyl)(4-(2-(2,5-dimethylphenylthio)-5-nitrophenylsulfonyl)-piperazin-1-yl)methanone 173. HPLC purity: 100%; $^1$H NMR (500 MHz, DMSO-$d_6$): δ 8.50 (d, J=2 Hz, 1H), 8.27 (dd, $J_1$=2 Hz, $J_2$=8 Hz, 1H), 7.49 (t, $J_1$=$J_2$=8 Hz, 3H), 7.44 (t, $J_1$=$J_2$=8 Hz, 3H), 7.35 (d, J=8 Hz, 1H), 6.82 (d, J=8 Hz, 1H), 3.71 (m, 2H), 3.37 (m, 6H), 2.33 (s, 3H), 2.25 (s, 3H); melting point: 205-207° C.

(4-(2-(2,5-Dimethylphenylthio)-5-nitrophenylsulfonyl)piperazin-1-yl)(4-methoxyphenyl)methanone 174. HPLC purity: 100%; $^1$H NMR (500 MHz, DMSO-$d_6$): δ 8.50 (d, J=2 Hz, 1H), 8.27 (dd, $J_1$=2 Hz, $J_2$=8 Hz, 1H), 7.48 (s, 1H), 7.42 (d, J=8 Hz, 1H), 7.37 (m, 3H), 6.97 (d, J=8 Hz, 2H), 5.82 (d, J=8 Hz, 1H), 3.78 (s, 3H), 3.60 (m, 4H), 3.36 (m, 4H), 2.33 (s, 3H), 2.25 (s, 3H); melting point: 163-167° C.

(4-(2-(2,5-Dimethylphenylthio)-5-nitrophenylsulfonyl)piperazin-1-yl)(furan-2-yl)methanone 175. HPLC purity: 96%; $^1$H NMR (500 MHz, DMSO-$d_6$): δ 8.51 (d, J=2 Hz, 1H), 8.26 (dd, $J_1$=2 Hz, $J_2$=8 Hz, 1H), 7.83 (s, 1H), 7.48 (s, 1H), 7.41 (d, J=8 Hz, 1H), 7.36 (d, J=8 Hz, 1H), 7.02 (d, J=2 Hz, 1H), 6.81 (d, J=8 Hz, 1H), 6.62 (dd, $J_1$=2 Hz, $J_2$=8 Hz, 1H), 3.79 (m, 4H), 3.40 (m, 4H), 2.32 (s, 3H), 2.24 (s, 3H); melting point: 160-163° C.

1-(4-(2-(2,5-Dichlorophenoxy)-5-nitrophenylsulfonyl)piperazin-1-yl)ethanone 176. HPLC purity: 98.7%; $^1$H NMR (500 MHz, DMSO-$d_6$): δ 8.59 (d, J=2 Hz, 1H), 8.43 (dd, $J_1$=2 Hz, $J_2$=8 Hz, 1H), 7.76 (d, J=8 Hz, 1H), 7.66 (d, J=2 Hz, 1H), 7.50 (dd, $J_1$=2 Hz, $J_2$=8 Hz, 1H), 7.11 (d, J=8 Hz, 1H), 3.51 (m, 4H), 3.31 (m, 2H), 3.23 (m, 2H), 1.98 (s, 3H); melting point: 270-273° C.

1-(4-(2-(2,5-Dichlorophenoxy)-5-nitrophenylsulfonyl)piperazin-1-yl)-3-methylbutan-1-one 177. HPLC purity: 100%; $^1$H NMR (500 MHz, DMSO-$d_6$): δ 8.59 (d, J=2 Hz, 1H), 8.43 (dd, $J_1$=2 Hz, $J_2$=8 Hz, 1H), 7.76 (d, J=8 Hz, 1H), 7.65 (d, J=2 Hz, 1H), 7.50 (dd, $J_1$=2 Hz, $J_2$=8 Hz, 1H), 7.11 (d, J=8 Hz, 1H), 3.54 (m, 4H), 3.29 (m, 2H), 3.22 (m, 2H), 2.16 (d, J=8 Hz, 2H), 1.92 (m, 1H), 0.86 (d, J=8 Hz, 6H); melting point: 157-160° C.

(4-(2-(2,5-Dichlorophenoxy)-5-nitrophenylsulfonyl)piperazin-1-yl)(4-(trifluoromethyl)phenyl)methanone 178.

HPLC purity: 99%; ¹H NMR (500 MHz, DMSO-d₆): δ 8.59 (d, J=2 Hz, 1H), 8.45 (dd, J₁=2 Hz, J₂=8 Hz, 1H), 7.79 (d, J=8 Hz, 2H), 7.76 (d, J=8 Hz, 1H), 7.70 (d, J=2 Hz, 1H), 7.61 (d, J=8 Hz, 2H), 7.51 (dd, J₁=2 Hz, J₂=8 Hz, 1H), 7.13 (d, J=8 Hz, 1H), 3.73 (m, 2H), 3.30-3.60 (m, 6H); melting point: 230-233° C.

4-Chloro-1-(4-(2-(2,5-dichlorophenoxy)-5-nitrophenylsulfonyl)piperazin-1-yl)butan-1-one 179. HPLC purity: 97.5%; ¹H NMR (500 MHz, DMSO-d₆): δ 8.59 (d, J=2 Hz, 1H), 8.43 (dd, J₁=2 Hz, J₂=8 Hz, 1H), 7.76 (d, J=8 Hz, 1H), 7.65 (d, J=2 Hz, 1H), 7.51 (dd, J₁=2 Hz, J₂=8 Hz, 1H), 7.11 (d, J=8 Hz, 1H), 3.63 (t, J₁=J₂=8 Hz, 2H), 3.53 (m, 4H), 3.31 (m, 2H), 3.24 (m, 2H), 2.43 (t, J₁=J₂=8 Hz, 2H), 1.91 (m, 2H); melting point: 145-149° C.

Cyclobutyl(4-(2-(2,5-dichlorophenoxy)-5-nitrophenylsulfonyl)piperazin-1-yl)methanone 180. HPLC purity: 98%; ¹H NMR (500 MHz, DMSO-d₆): δ 8.58 (d, J=2 Hz, 1H), 8.43 (dd, J₁=2 Hz, J₂=8 Hz, 1H), 7.76 (d, J=8 Hz, 1H), 7.65 (d, J=2 Hz, 1H), 7.50 (dd, J₁=2 Hz, J₂=8 Hz, 1H), 7.11 (d, J=8 Hz, 1H), 3.52 (m, 2H), 3.39 (m, 2H), 3.25 (m, 5H), 2.10 (m, 2H), 2.03 (m, 2H), 1.84 (m, 1H), 1.70 (m, 1H); melting point: 237-241° C.

Cyclohexyl(4-(2-(2,5-dichlorophenoxy)-5-nitrophenylsulfonyl)piperazin-1-yl)methanone 181. HPLC purity: 99%; ¹H NMR (500 MHz, DMSO-d₆): δ 8.59 (d, J=2 Hz, 1H), 8.43 (dd, J₁=2 Hz, J₂=8 Hz, 1H), 7.76 (d, J=8 Hz, 1H), 7.65 (d, J=2 Hz, 1H), 7.51 (dd, J₁=2 Hz, J₂=8 Hz, 1H), 7.11 (d, J=8 Hz, 1H), 3.55 (d, J=32 Hz, 4H), 3.24 (d, J=32 Hz, 4H), 2.52 (m, 1H), 1.56-1.66 (m, 5H), 1.27 (m, 4H), 1.13 (m, 1H); melting point: 200-203° C.

(4-(2-(2,5-Dichlorophenoxy)-5-nitrophenylsulfonyl)piperazin-1-yl)(phenyl)methanone 182. HPLC purity: 98%; ¹H NMR (500 MHz, DMSO-d₆): δ 8.59 (d, J=2 Hz, 1H), 8.44 (dd, J₁=2 Hz, J₂=8 Hz, 1H), 7.76 (d, J=8 Hz, 1H), 7.71 (d, J=2 Hz, 1H), 7.50 (dd, J₁=2 Hz, J₂=8 Hz, 1H), 7.36-7.45 (m, 5H), 7.13 (d, J=8 Hz, 1H), 3.70 (m, 2H), 3.35 (m, 6H); melting point: 206-209° C.

(4-Chlorophenyl)(4-(2-(2,5-dichlorophenoxy)-5-nitrophenylsulfonyl)-piperazin-1-yl)methanone 183. HPLC purity: 97%; ¹H NMR (500 MHz, DMSO-d₆): δ 8.59 (d, J=2 Hz, 1H), 8.45 (dd, J₁=2 Hz, J₂=8 Hz, 1H), 7.76 (d, J=8 Hz, 1H), 7.70 (d, J=2 Hz, 1H), 7.50 (dd, J₁=2 Hz, J₂=8 Hz, 1H), 7.48 (d, J=8 Hz, 2H), 7.42 (d, J=8 Hz, 2H), 7.13 (d, J=8 Hz, 1H), 3.69 (m, 2H), 3.34 (m, 6H); melting point: 226-229° C.

(4-(2-(2,5-Dichlorophenoxy)-5-nitrophenylsulfonyl)piperazin-1-yl)(4-methoxyphenyl)methanone 184. HPLC purity: 97%; ¹H NMR (500 MHz, DMSO-d₆): δ 8.59 (d, J=2 Hz, 1H), 8.44 (dd, J₁=2 Hz, J₂=8 Hz, 1H), 7.76 (d, J=8 Hz, 1H), 7.69 (d, J=2 Hz, 1H), 7.50 (dd, J₁=2 Hz, J₂=8 Hz, 1H), 7.36 (d, J=8 Hz, 2H), 7.12 (d, J=8 Hz, 1H), 6.95 (d, J=8 Hz, 2H), 3.78 (s, 3H), 3.56 (m, 4H), 3.29 (m, 4H); melting point: 197-200° C.

(4-(2-(2,5-Dichlorophenoxy)-5-nitrophenylsulfonyl)piperazin-1-yl)(furan-2-yl)methanone 185. HPLC purity: 98%; ¹H NMR (500 MHz, DMSO-d₆): δ 8.60 (d, J=2 Hz, 1H), 8.43 (dd, J₁=2 Hz, J₂=8 Hz, 1H), 7.82 (s, 1H), 7.75 (d, J=8 Hz, 1H), 7.67 (d, J=2 Hz, 1H), 7.50 (dd, J₁=2 Hz, J₂=8 Hz, 1H), 7.10 (d, J=8 Hz, 1H), 6.99 (d, J=8 Hz, 1H), 6.61 (d, J=2 Hz, 1H), 3.75 (m, 4H), 3.37 (m, 4H); melting point: 236-240° C.

1-(4-(2-(2,5-Dimethylphenoxy)-5-nitrophenylsulfonyl)piperazin-1-yl)-3-methylbutan-1-one 187. HPLC purity: 97.3%; ¹H NMR (500 MHz, DMSO-d₆): δ 8.59 (d, J=2 Hz, 1H), 8.41 (dd, J₁=2 Hz, J₂=8 Hz, 1H), 7.31 (d, J=8 Hz, 1H), 7.11 (d, J=8 Hz, 1H), 7.01 (s, 1H), 6.84 (d, J=8 Hz, 1H), 3.54 (m, 4H), 3.29 (m, 2H), 3.22 (m, 2H), 2.30 (s, 3H), 2.17 (d, J=8 Hz, 2H), 2.08 (s, 3H), 1.93 (m, 1H), 0.86 (d, J=8 Hz, 6H); melting point: 155-158° C.

(4-(2-(2,5-Dimethylphenoxy)-5-nitrophenylsulfonyl)piperazin-1-yl)(4-(trifluoromethyl)phenyl)methanone 188. HPLC purity: 99%; ¹H NMR (500 MHz, DMSO-d₆): δ 8.58 (d, J=2 Hz, 1H), 8.42 (dd, J₁=2 Hz, J₂=8 Hz, 1H), 7.79 (d, J=8 Hz, 2H), 7.62 (d, J=8 Hz, 2H), 7.31 (d, J=8 Hz, 1H), 7.12 (d, J=8 Hz, 1H), 7.08 (s, 1H), 6.86 (d, J=8 Hz, 1H), 3.73 (m, 2H), 3.40 (m, 6H), 2.32 (s, 3H), 2.09 (s, 3H); melting point: 177-180° C.

(4-(2-(2,5-Dimethylphenoxy)-5-nitrophenylsulfonyl)piperazin-1-yl)(4-methoxyphenyl)methanone 189. HPLC purity: 99.7%; ¹H NMR (500 MHz, DMSO-d₆): δ 8.59 (d, J=2 Hz, 1H), 8.42 (dd, J₁=2 Hz, J₂=8 Hz, 1H), 7.35 (d, J=8 Hz, 2H), 7.31 (d, J=8 Hz, 1H), 7.12 (d, J=8 Hz, 1H), 7.07 (s, 1H), 6.95 (d, J=8 Hz, H), 6.86 (d, J=8 Hz, 1H), 3.78 (s, 3H), 3.57 (m, 4H), 3.33 (m, 4H), 2.32 (s, 3H), 2.09 (s, 3H); melting point: 161-164° C.

(4-(2-(2,5-Dimethylphenoxy)-5-nitrophenylsulfonyl)piperazin-1-yl)(furan-2-yl)methanone 190. HPLC purity: 99.5%; ¹H NMR (500 MHz, DMSO-d₆): δ 8.59 (d, J=2 Hz, 1H), 8.41 (dd, J₁=2 Hz, J₂=8 Hz, 1H), 7.82 (d, J=2 Hz, 1H), 7.31 (d, J=8 Hz, 1H), 7.11 (d, J=8 Hz, 1H), 7.05 (s, 1H), 6.99 (d, J=4 Hz, 1H), 6.84 (d, J=8 Hz, 1H), 6.62 (d, J=2 Hz, 1H), 3.75 (m, 4H), 3.37 (m, 4H), 2.29 (s, 3H), 2.08 (s, 3H); melting point: 170-174° C.

N-Allyl-4-(2-(2,5-dichlorophenylthio)-5-nitrophenylsulfonyl)piperazine-1-carboxamide 191. HPLC purity: 98.2%; ¹H NMR (500 MHz, DMSO-d₆): δ 8.52 (d, J=2 Hz, 1H), 8.28 (dd, J₁=2 Hz, J₂=8 Hz, 1H), 7.98 (d, J=2 Hz, 1H), 7.80 (d, J=8 Hz, 1H), 7.74 (dd, J₁=2 Hz, J₂=8 Hz, 1H), 7.00 (d, J=8 Hz, 1H), 6.70 (t, J=4 Hz, 1H), 5.76 (m, 1H), 5.06 (d, J=9 Hz, 1H), 4.97 (d, J=4 Hz, 1H), 3.62 (m, 2H), 3.42 (m, 4H), 3.26 (m, 4H); melting point: 198-202° C.

4-(2-(2,5-Dichlorophenylthio)-5-nitrophenylsulfonyl)-N,N-diethylpiperazine-1-carboxamide 192. HPLC purity: 99%; ¹H NMR (500 MHz, DMSO-d₆): δ 8.51 (d, J=2 Hz, 1H), 8.28 (dd, J₁=2 Hz, J₂=8 Hz, 1H), 7.99 (d, J=2 Hz, 1H), 7.81 (d, J=8 Hz, 1H), 7.74 (dd, J₁=2 Hz, J₂=8 Hz, 1H), 7.01 (d, J=8 Hz, 1H), 3.32 (m, 4H), 3.17 (m, 4H), 3.09 (m, 4H), 1.00 (m, 6H); melting point: 160-163° C.

4-(2-(2,5-Dichlorophenylthio)-5-nitrophenylsulfonyl)-N-p-tolylpiperazine-1-carboxamide 193. HPLC purity: 97%; ¹H NMR (500 MHz, DMSO-d₆): δ 8.53 (m, 2H), 8.28 (dd, J₁=2 Hz, J₂=8 Hz, 1H), 8.01 (d, J=2 Hz, 1H), 7.81 (d, J=8 Hz, 1H), 7.74 (dd, J₁=2 Hz, J₂=8 Hz, 1H), 7.28 (d, J=8 Hz, 2H), 7.01 (d, J=8 Hz, 3H), 3.56 (m, 4H), 3.35 (m, 4H), 2.21 (s, 3H); melting point: 231-234° C.

N-(4-Cyanophenyl)-4-(2-(2,5-dichlorophenylthio)-5-nitrophenylsulfonyl)-piperazine-1-carboxamide 194. HPLC purity: 97.7%; ¹H NMR (500 MHz, DMSO-d₆): δ 9.09 (s, 1H), 8.53 (d, J=2 Hz, 1H), 8.28 (dd, J₁=2 Hz, J₂=8 Hz, 1H), 8.00 (d, J=2 Hz, 1H), 7.81 (d, J=8 Hz, 1H), 7.74 (dd, J₁=2 Hz, J₂=8 Hz, 1H), 7.68 (d, J=8 Hz, 2H), 7.62 (d, J=2 Hz, 2H), 7.01 (d, J=8 Hz, 1H), 3.60 (m, 4H), 3.36 (m, 4H); melting point: 232-235° C.

4-(2-(2,5-Dichlorophenylthio)-5-nitrophenylsulfonyl)-N-(4-nitrophenyl)-piperazine-1-carboxamide 195. HPLC purity: 98.3%; ¹H NMR (500 MHz, DMSO-d₆): δ 9.31 (s, 1H), 8.53 (d, J=2 Hz, 1H), 8.28 (dd, J₁=2 Hz, J₂=8 Hz, 1H), 8.14 (d, J=8 Hz, 2H), 8.00 (d, J=2 Hz, 1H), 7.81 (d, J=8 Hz, 1H), 7.75 (dd, J₁=2 Hz, J₂=8 Hz, 1H), 7.67 (d, J=8 Hz, 1H), 7.02 (d, J=8 Hz, 1H), 3.62 (m, 4H), 3.37 (m, 4H); melting point: 242-246° C.

4-(2-(2,5-Dichlorophenylthio)-5-nitrophenylsulfonyl)-N-isopropylpiperazine-1-carbothioamide 196. HPLC purity: 100%; ¹H NMR (500 MHz, DMSO-d₆): δ 8.51 (d, J=2 Hz, 1H), 8.28 (dd, J₁=2 Hz, J₂=8 Hz, 1H), 8.00 (d, J=2 Hz, 1H), 7.81 (d, J=8 Hz, 1H), 7.74 (dd, J₁=2 Hz, J₂=8 Hz, 1H), 7.46 (d, J=6 Hz, 1H), 7.00 (d, J=8 Hz, 1H), 4.46 (m, 1H), 3.90 (s, 4H), 3.32 (s, 4H), 1.10 (d, 6H); melting point: 190-193° C.

N-(3-chlorobenzyl)-4-(2-(2,5-dichlorophenylthio)-5-nitrophenylsulfonyl)-piperazine-1-carbothioamide 197. HPLC purity: 100%; $^1$H NMR (500 MHz, DMSO-d$_6$): δ 8.52 (d, J=2 Hz, 1H), 8.41 (t, J$_1$=J$_2$=4 Hz, 1H), 8.28 (dd, J$_1$=2 Hz, J$_2$=8 Hz, 1H), 8.00 (d, J=2 Hz, 1H), 7.81 (d, J=8 Hz, 1H), 7.74 (dd, J$_1$=2 Hz, J$_2$=8 Hz, 1H), 7.27 (m, 3H), 7.21 (d, J=8 Hz, 1H), 7.01 (d, J=8 Hz, 1H), 4.75 (d, J=8 Hz, 2H), 3.97 (m, 4H), 3.37 (m, 4H); melting point: 170-174° C.

4-(2-(2,5-Dichlorophenylthio)-5-nitrophenylsulfonyl)-N-(3-oxopentyl)-piperazine-1-carbothioamide 198. HPLC purity: 100%; $^1$H NMR (500 MHz, DMSO-d$_6$): δ 8.51 (d, J=2 Hz, 1H), 8.28 (dd, J$_1$=2 Hz, J$_2$=8 Hz, 1H), 8.00 (d, J=2 Hz, 1H), 7.89 (t, J$_1$=J$_2$=4 Hz, 1H), 7.81 (d, J=8 Hz, 1H), 7.74 (dd, J$_1$=2 Hz, J$_2$=8 Hz, 1H), 7.00 (d, J=8 Hz, 1H), 4.02 (q, J$_1$=J$_2$=8 Hz, 2H), 3.89 (m, 4H), 3.67 (m, 2H), 2.57 (t, J$_1$=J$_2$=6 Hz, 2H), 1.15 (t, J$_1$=J$_2$=6 Hz, 3H); melting point: 200-204° C.

4-(2-(2,5-Dichlorophenylthio)-5-nitrophenylsulfonyl)-N-phenylpiperazine-1-carbothioamide 199. HPLC purity: 99.8%; $^1$H NMR (500 MHz, DMSO-d$_6$): δ 9.46 (s, 1H), 8.54 (d, J=2 Hz, 1H), 8.29 (dd, J$_1$=2 Hz, J$_2$=8 Hz, 1H), 8.02 (d, J=2 Hz, 1H), 7.82 (d, J=8 Hz, 1H), 7.74 (dd, J$_1$=2 Hz, J$_2$=8 Hz, 1H), 7.26 (m, 4H), 7.10 (m, 1H), 7.02 (d, J=8 Hz, 1H), 4.03 (m, 4H), 3.42 (m, 4H); melting point: 198-201° C.

4-(2-(2,5-Dichlorophenylthio)-5-nitrophenylsulfonyl)-N-(2-morpholinoethyl)-piperazine-1-carbothioamide 200. HPLC purity: 100%; $^1$H NMR (500 MHz, DMSO-d$_6$): δ 8.51 (d, J=2 Hz, 1H), 8.28 (dd, J$_1$=2 Hz, J$_2$=8 Hz, 1H), 8.00 (d, J=2 Hz, 1H), 7.81 (d, J=8 Hz, 1H), 7.74 (dd, J$_1$=2 Hz, J$_2$=8 Hz, 2H), 7.00 (d, J=8 Hz, 1H), 3.89 (m, 4H), 3.58 (m, 2H), 3.50 (m, 4H), 2.43 (t, J$_1$=J$_2$=6 Hz, 2H), 2.35 (m, 4H); melting point: 130-136° C.

1-(2-(2,5-Dichlorophenylthio)-5-nitrophenylsulfonyl)-4-(methylsulfonyl)-piperazine 202. HPLC purity: 100%; $^1$H NMR (500 MHz, DMSO-d$_6$): δ 8.54 (d, J=8 Hz, 2H), 8.30 (dd, J$_1$=2 Hz, J$_2$=8 Hz, 1H), 8.02 (d, J=2 Hz, 1H), 7.82 (d, J=8 Hz, 1H), 7.74 (dd, J$_1$=2 Hz, J$_2$=8 Hz, 1H), 7.02 (d, J=8 Hz, 1H), 3.44 (m, 4H), 3.24 (m, 4H), 2.92 (s, 3H); melting point: 277-281° C.

4-(2-(2,5-Dichlorophenylthio)-5-nitrophenylsulfonyl)-N,N-dimethyl-piperazine-1-sulfonamide 203. HPLC purity: 100%; $^1$H NMR (500 MHz, DMSO-d$_6$): δ 8.53 (d, J=2 Hz, 1H), 8.29 (dd, J$_1$=2 Hz, J$_2$=8 Hz, 1H), 8.00 (d, J=2 Hz, 1H), 7.82 (d, J=8 Hz, 1H), 7.74 (dd, J$_1$=2 Hz, J$_2$=8 Hz, 1H), 7.03 (d, J=8 Hz, 1H), 3.39 (m, 4H), 3.26 (m, 4H), 2.74 (s, 6H); melting point: 231-234° C.

1-(2-(2,5-Dichlorophenylthio)-5-nitrophenylsulfonyl)-4-(phenylsulfonyl)-piperazine 204. HPLC purity: 100%; $^1$H NMR (500 MHz, DMSO-d$_6$): δ 8.48 (d, J=2 Hz, 1H), 8.23 (dd, J$_1$=2 Hz, J$_2$=8 Hz, 1H), 7.90 (d, J=2 Hz, 1H), 7.69-7.76 (m, 5H), 7.60 (m, 2H), 6.93 (d, J=8 Hz, 1H), 3.43 (m, 4H), 2.99 (m, 4H); melting point: 236-239° C.

1-(2-(2,5-dichlorophenylthio)-5-nitrophenylsulfonyl)-4-(4-(trifluoromethyl)phenylsulfonyl)piperazine 205. HPLC purity: 100%; $^1$H NMR (500 MHz, DMSO-d$_6$): δ 8.51 (d, J=2 Hz, 1H), 8.23 (dd, J$_1$=2 Hz, J$_2$=8 Hz, 1H), 8.01 (d, J=8 Hz, 2H), 7.94 (d, J=8 Hz, 3H), 7.74 (dd, J$_1$=2 Hz, J$_2$=8 Hz, 1H), 7.64 (d, J=8 Hz, 1H), 6.92 (d, J=8 Hz, 1H), 3.44 (m, 4H), 3.05 (m, 4H); melting point: 264-267° C.

Example 5

CCR3 Receptor Binding Assay

Cells were washed once with PBS and resuspended in a binding buffer (25 mM HEPES pH 7.6, 5 mM MgCl$_2$, 1 mM CaCl$_2$, 0.5% BSA, 0.1% NaN$_3$). 100 mL of cell suspension (2×10$^5$ cells/well) and 0.1 nM [$^{125}$I]-labeled human eotaxin/CCL11 (2000 Ci/mmol specific activity) were mixed in a 96-well U-bottom polypropylene plate, and incubated for 60 min at room temperature for the binding reaction. The cell suspension was then transferred to a filtration plate (#MAFB, Millipore), and washed 3 times with the binding buffer containing 0.5 M NaCl, scintillant added, and the radioactivity was counted on a TopCount (Packard). For the determination of non-specific binding, the cell suspension and [$^{125}$I]-labeled human eotaxin/CCL11 were incubated in the presence of 500 nM of unlabeled human eotaxin/CCL11. See, Iino et al., "Molecular cloning and functional characterization of cynomolgus monkey (*Macaca fascicularis*) CC chemokine receptor, CCR$^3$," Cytokine 2002, 19, 276-286.

The biological results are summarized in Table 1, wherein A represents a value no greater than 50 nM; B represents a value greater than 50 nM but no greater than 500 nM; C represents a value greater than 500 nM but no greater than 5 μM; and D represents a value greater than 5 μM.

TABLE 1

| Cmpd # | K$_i$ | Cmpd # | K$_i$ |
|---|---|---|---|
| 51 | D | 52 | D |
| 53 | D | 54 | D |
| 55 | D | 56 | D |
| 57 | C | 58 | B |
| 59 | D | 60 | D |
| 61 | D | 62 | D |
| 63 | D | 64 | D |
| 65 | D | 66 | D |
| 67 | D | 68 | D |
| 69 | D | 70 | A |
| 71 | D | 72 | C |
| 73 | D | 74 | D |
| 75 | A | 76 | A |
| 77 | A | 78 | B |
| 79 | A | 80 | C |
| 81 | C | 82 | C |
| 83 | C | 84 | C |
| 85 | C | 86 | D |
| 87 | D | 88 | D |
| 89 | B | 90 | B |
| 91 | B | 92 | D |
| 93 | B | 94 | D |
| 95 | B | 96 | C |
| 97 | B | 98 | D |
| 99 | D | 100 | D |
| 101 | D | 102 | D |
| 103 | D | 104 | D |
| 105 | D | 106 | D |
| 107 | D | 108 | D |
| 109 | A | 110 | A |
| 111 | A | 112 | D |
| 113 | D | 114 | C |
| 115 | D | 116 | D |
| 117 | D | 118 | D |
| 119 | D | 120 | D |
| 121 | D | 122 | D |
| 123 | D | 124 | B |
| 125 | A | 126 | D |
| 127 | A | 128 | C |
| 129 | D | 130 | D |
| 131 | D | 132 | D |
| 133 | B | 134 | B |
| 135 | A | 136 | A |
| 137[1] | B | 138 | B |
| 139 | A | 140 | A |
| 141 | A | 142 | B |
| 143 | B | 144 | A |
| 145 | A | 146 | A |
| 147 | D | 148 | B |
| 149 | D | 150 | D |
| 152 | D | 153 | D |
| 154 | D | 155 | D |

TABLE 1-continued

| Cmpd # | $K_i$ | Cmpd # | $K_i$ |
|---|---|---|---|
| 156 | D | 157 | D |
| 158 | D | 159 | D |
| 160 | D | 161 | D |
| 162 | D | 163 | D |
| 164 | D | 165 | D |
| 172 | D | 173 | D |
| 174 | D | 177 | D |
| 182 | D | 184 | D |
| 185 | D | 189 | D |
| 190 | D | 191 | A |
| 193 | D | 194 | D |
| 195 | D | 198 | A |
| 202 | D | 203 | D |
| 204 | D | 205 | D |

[1] The compound was tested as a hydrochloride salt.

* * *

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A compound of Formula I:

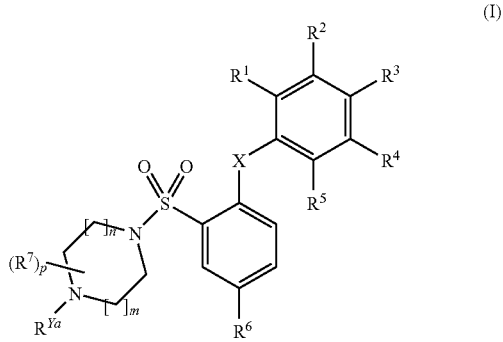

or an enantiomer, a mixture of enantiomers, a mixture of two or more diastereomers, a tautomer, or a mixture of two or more tautomers thereof; or a pharmaceutically acceptable salt or prodrug thereof;

wherein:

$R^1$, $R^2$, $R^3$, $R^4$, $R^5$, and $R^6$ are each independently (a) hydrogen, halo, cyano, nitro, or guanidine; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^7$ is (a) halo, cyano, nitro, oxo, or guanidine; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

X is O or S;

$R^{Ya}$ is —C(O)$R^{1a}$, —C(O)O$R^{1a}$, —C(O)N$R^{1b}R^{1c}$, —C(S)N$R^{1b}R^{1c}$, —C(S)N$R^{1a}$C(O)N$R^{1b}R^{1c}$, —C(N$R^{1a}$)N$R^{1b}R^{1c}$, C(NNO$_2$)N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$; with the proviso that $R^{Ya}$ is not —C(O)O-t-butyl;

m is an integer from 0 to 3;

n is an integer from 1 to 3;

p is an integer from 0 to 4; and each $R^{1a}$, $R^{1b}$, $R^{1c}$, and $R^{1d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or each pair of $R^{1b}$ and $R^{1c}$ together with the N atom to which they are attached independently form heteroaryl or heterocyclyl;

with the proviso that the compound is not 4-(2-(3,5-dimethylphenoxy)-5-nitrophenylsulfonyl)piperazine-1-carbaldehyde;

wherein each alkyl, alkenyl, alkynyl, cycloalkyl, aryl, aralkyl, heterocyclyl, and heteroaryl is optionally substituted with one or more groups, each independently selected from (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more substituents Q; and (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen;

(ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more substituents Q; or (iii) $R^b$ and $R^c$ together with the N atom to which they are attached form heterocyclyl, optionally substituted with one or more substituents Q;

wherein each Q is independently selected from the group consisting of (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(N$R^e$)N$R^fR^g$, —O$R^e$, —OC(O)$R^e$, —OC(O)O$R^e$, —OC(O)N$R^fR^g$, —OC(=N$R^e$)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^h$, —N$R^e$C(O)N$R^fR^g$, —N$R^e$C(=N$R^h$)N$R^fR^g$, —N$R^e$S(O)$R^h$, —N$R^e$S(O)$_2R^h$, —N$R^e$S(O)N$R^fR^g$, —N$R^e$S(O)$_2$N$R^f$ $R^g$, —$SR^e$, —$S(O)R^e$, —$S(O)_2R^e$, —$S(O)NR^fR^g$, and —$S(O)_2NR^fR^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

2. The compound of claim 1, wherein $R^{Ya}$ is —$C(O)R^{1a}$, —$C(O)NR^{1b}R^{1c}$, —$C(S)NR^{1b}R^{1c}$, —$C(S)NR^{1a}C(O)NR^{1b}R^{1c}$, $C(NNO_2)NR^{1b}R^{1c}$, or —$S(O)_2R^{1a}$.

3. The compound of claim 2, wherein $R^{1a}$ is (a) hydrogen; (b) $C_{1-6}$ alkyl, optionally substituted with one, two, or three substituents, each of which is independently selected from cyano, halo, $C_{3-7}$ cycloalkyl, $C_{6-14}$ aryl, heteroaryl, heterocyclyl, —$C(O)R^a$, —$C(O)OR^a$, and —$SR^a$, where the cycloalkyl, aryl, heteroaryl, and heterocyclyl are each further optionally substituted with one, two, or three substituents, each of which is independently halo or $C_{1-6}$ alkyl; (c) $C_{1-6}$ alkenyl, optionally substituted with $C_{6-14}$ aryl; (d) $C_{3-7}$ cycloalkyl, optionally substituted with one or two $C_{1-6}$ alkyl; (e) $C_{6-14}$ aryl, optionally substituted with one, two, or three substituents, each of which is independently selected from halo, nitro, cyano, —$OR^a$, —$C(O)R^a$, and $C_{1-6}$ alkyl, where the alkyl is further optionally substituted with one, two, or three halo; (f) heteroaryl, optionally substituted with one, two, or three substituents, each of which is independently halo or $C_{1-6}$ alkyl; or (g) heterocyclyl.

4. The compound of claim 2, wherein $R^{1a}$ is (a) hydrogen; or (b) $C_{1-6}$ alkyl, $C_{2-6}$ alkenyl, $C_{3-7}$ cycloalkyl, $C_{6-14}$ aryl, heteroaryl, or heterocyclyl, each optionally substituted with one or two substituents, each of which is independently selected from halo, cyano, nitro, $C_{1-6}$ alkyl, $C_{3-7}$ cycloalkyl, $C_{6-14}$ aryl, heteroaryl, heterocyclyl, —$OR^a$, —$SR^a$, and —$C(O)R^a$, where the alkyl, cycloalkyl, aryl, heteroaryl, and heterocyclyl are each optionally further substituted with one or two substituents, each of which is independently halo or $C_{1-6}$ alkyl.

5. The compound of claim 2, wherein $R^{1a}$ is (a) hydrogen; or (b) $C_{1-6}$ alkyl, $C_{2-6}$ alkenyl, $C_{3-7}$ cycloalkyl, $C_{6-14}$ aryl, heteroaryl, or heterocyclyl, each optionally substituted with one or two substituents, each of which is independently selected from fluoro, chloro, cyano, nitro, methyl, trifluoromethyl, ethyl, methoxy, ethoxy, methylthio, (1S,2S,4R)-7,7-dimethylbicyclo[2.2.1]-heptyl, phenyl, chlorophenyl, furanyl, morpholinyl, acetyl, propionyl, and ethoxycarbonyl.

6. The compound of claim 4, wherein $R^{1a}$ is (a) hydrogen; (b) $C_{1-6}$ alkyl, optionally substituted with a substituent selected from chloro, cyano, ethoxy, methylthio, (1S,2S,4R)-7,7-dimethylbicyclo[2.2.1]-heptyl, phenyl, chlorophenyl, furanyl, morpholinyl, propionyl, and ethoxycarbonyl; (c) $C_{2-6}$ alkenyl, optionally substituted with phenyl; (d) $C_{3-7}$ cycloalkyl; (e) $C_{6-14}$ aryl, optionally substituted with one or two substituents, each independently selected from fluoro, chloro, cyano, nitro, methyl, trifluoromethyl, ethyl, methoxy, and acetyl; (f) heteroaryl, optionally substituted with one or two methyl; or (g) heterocyclyl.

7. The compound of claim 6, wherein $R^{1a}$ is (a) hydrogen; (b) methyl, ethyl, propyl, butyl, or pentyl, each optionally substituted with a substituent selected from chloro, cyano, ethoxy, methylthio, (1S,2S,4R)-7,7-dimethylbicyclo[2.2.1]-heptyl, phenyl, chlorophenyl, furanyl, morpholinyl, propionyl, and ethoxycarbonyl; (c) ethenyl or allyl, each optionally substituted with phenyl; (d) cyclobutyl, cyclopentyl, or cyclohexyl; (e) phenyl, optionally substituted with one or two substituents, each independently selected from fluoro, chloro, cyano, nitro, methyl, trifluoromethyl, ethyl, methoxy, and acetyl; (f) furanyl, thienyl, isoxazolyl, pyrazolyl, 1,2,3-thiadiazolyl, pyridinyl, pyrazyl, benzofuranyl, benzo[c][1,2,5]oxadiazolyl, benzothienyl, or benzothiazolyl, each optionally substituted with one or two methyl; or (g) morpholinyl.

8. The compound of claim 2, wherein $R^{1b}$ is hydrogen or $C_{1-6}$ alkyl.

9. The compound of claim 8, wherein $R^{1b}$ is hydrogen, methyl, or ethyl.

10. The compound of claim 2, wherein $R^{1c}$ is (a) hydrogen; (b) $C_{1-6}$ alkyl, optionally substituted with one, two, or three substituents, each of which is independently selected from cyano, halo, $C_{3-7}$ cycloalkyl, $C_{6-14}$ aryl, heteroaryl, heterocyclyl, —$C(O)R^a$, —$C(O)OR^a$, and —$SR^a$, where the cycloalkyl, aryl, heteroaryl, and heterocyclyl are each further optionally substituted with one, two, or three substituents, each of which is independently halo or $C_{1-6}$ alkyl; (c) $C_{1-6}$ alkenyl, optionally substituted with $C_{6-14}$ aryl; (d) $C_{3-7}$ cycloalkyl, optionally substituted with one or two $C_{1-6}$ alkyl; (e) $C_{6-14}$ aryl, optionally substituted with one, two, or three substituents, each of which is independently selected from halo, nitro, cyano, —$OR^a$, —$C(O)R^a$, and $C_{1-6}$ alkyl, where the alkyl is further optionally substituted with one, two, or three halo; (f) heteroaryl, optionally substituted with one, two, or three substituents, each of which is independently halo or $C_{1-6}$ alkyl; or (g) heterocyclyl.

11. The compound of claim 2, wherein $R^{1c}$ is (a) hydrogen; or (b) $C_{1-6}$ alkyl, $C_{2-6}$ alkenyl, $C_{3-7}$ cycloalkyl, $C_{6-14}$ aryl, heteroaryl, or heterocyclyl, each optionally substituted with one or two substituents, each of which is independently selected from halo, cyano, nitro, $C_{1-6}$ alkyl, $C_{3-7}$ cycloalkyl, $C_{6-14}$ aryl, heteroaryl, heterocyclyl, —$OR^a$, —$SR^a$, and —$C(O)R^a$, where $R^a$ is as defined herein and the alkyl, cycloalkyl, aryl, heteroaryl, and heterocyclyl are each optionally further substituted with one or two substituents, each of which is independently halo or $C_{1-6}$ alkyl.

12. The compound of claim 10, wherein $R^{1c}$ is (a) hydrogen; or (b) $C_{1-6}$ alkyl, $C_{2-6}$ alkenyl, $C_{3-7}$ cycloalkyl, $C_{6-14}$ aryl, heteroaryl, or heterocyclyl, each optionally substituted with one or two substituents, each of which is independently selected from fluoro, chloro, cyano, nitro, methyl, trifluoromethyl, ethyl, methoxy, ethoxy, methylthio, (1S,2S,4R)-7,7-dimethylbicyclo[2.2.1]-heptyl, phenyl, chlorophenyl, furanyl, morpholinyl, acetyl, propionyl, and ethoxycarbonyl.

13. The compound of claim 10, wherein $R^{1c}$ is (a) hydrogen; (b) $C_{1-6}$ alkyl, optionally substituted with a substituent selected from chloro, cyano, ethoxy, methylthio, (1S,2S,4R)-7,7-dimethylbicyclo[2.2.1]-heptyl, phenyl, chlorophenyl, furanyl, morpholinyl, propionyl, and ethoxycarbonyl; (c) $C_{2-6}$ alkenyl, optionally substituted with phenyl; (d) $C_{3-7}$ cycloalkyl; (e) $C_{6-14}$ aryl, optionally substituted with one or two substituents, each independently selected from fluoro, chloro, cyano, nitro, methyl, trifluoromethyl, ethyl, methoxy, and acetyl; (f) heteroaryl, optionally substituted with one or two methyl; or (g) heterocyclyl.

14. The compound of claim 10, wherein $R^{1c}$ is (a) hydrogen; (b) methyl, ethyl, propyl, butyl, or pentyl, each optionally substituted with a substituent selected from chloro, cyano, ethoxy, methylthio, (1S,2S,4R)-7,7-dimethylbicyclo [2.2.1]-heptyl, phenyl, chlorophenyl, furanyl, morpholinyl, propionyl, and ethoxycarbonyl; (c) ethenyl or allyl, each optionally substituted with phenyl; (d) cyclobutyl, cyclopentyl, or cyclohexyl; (e) phenyl, optionally substituted with one or two substituents, each independently selected from fluoro, chloro, cyano, nitro, methyl, trifluoromethyl, ethyl, methoxy, and acetyl; (f) furanyl, thienyl, isoxazolyl, pyrazolyl, 1,2,3-thiadiazolyl, pyridinyl, pyrazyl, benzofuranyl, benzo[c][1,2,5]oxadiazolyl, benzothienyl, or benzothiazolyl, each optionally substituted with one or two methyl; or (g) morpholinyl.

15. The compound of claim 1, wherein $R^1$, $R^2$, $R^3$, $R^4$, and $R^5$ are each independently hydrogen, halo, or $C_{1-6}$ alkyl.

16. The compound of claim 15, wherein two of $R^1$, $R^2$, $R^3$, $R^4$, and $R^5$ are halo or $C_{1-6}$ alkyl, and the remaining three are hydrogen.

17. The compound of claim 15, wherein two of $R^1$, $R^2$, $R^3$, $R^4$, and $R^5$ are chloro or methyl, and the remaining three are hydrogen.

18. The compound of claim 17, wherein $R^1$, $R^3$, and $R^5$ are hydrogen, and $R^2$ and $R^4$ are chloro or methyl.

19. The compound of claim 18, wherein $R^2$ and $R^4$ are chloro.

20. The compound of claim 18, wherein $R^2$ and $R^4$ are methyl.

21. The compound of claim 17, wherein $R^2$, $R^3$, and $R^5$ are hydrogen, and $R^1$ and $R^4$ are chloro or methyl.

22. The compound of claim 21, wherein $R^1$ and $R^4$ are chloro.

23. The compound of claim 21, wherein $R^1$ and $R^4$ are methyl.

24. The compound of claim 1, wherein $R^6$ is cyano or nitro.

25. The compound of claim 1, wherein $R^7$ is $C_{1-6}$ alkyl.

26. The compound of claim 1, wherein m is 1.

27. The compound of claim 1, wherein n is 1 or 2.

28. The compound of claim 1, wherein p is 0.

29. The compound of claim 1, wherein X is O.

30. The compound of claim 1, wherein X is S.

31. The compound of claim 1 selected from the group consisting of:

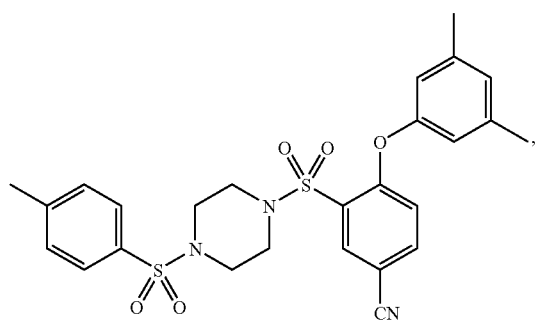

53

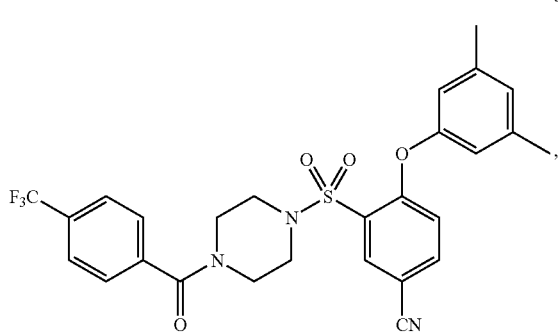

54

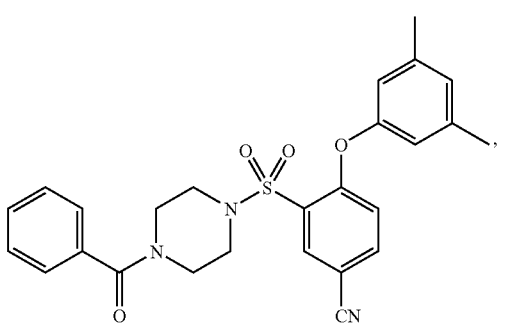

55

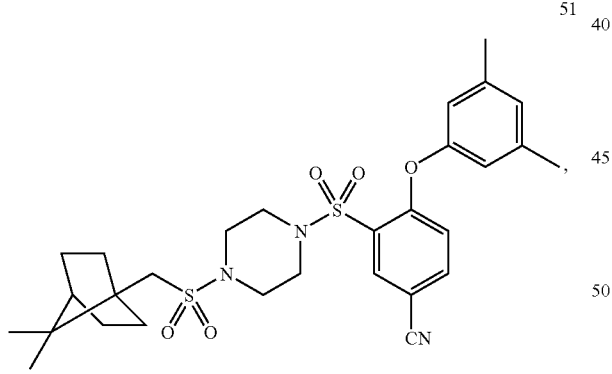

51

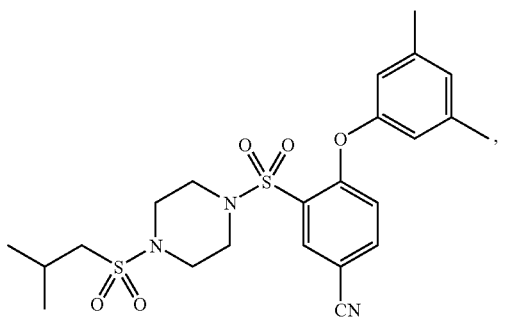

56

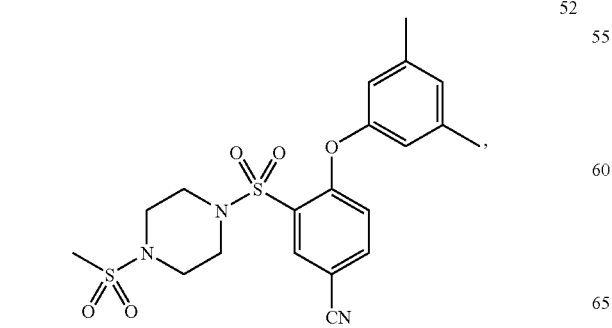

52

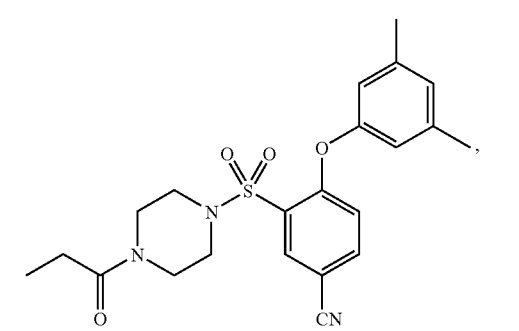

57

-continued
58
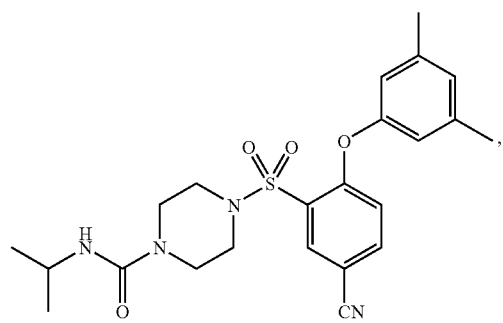
59
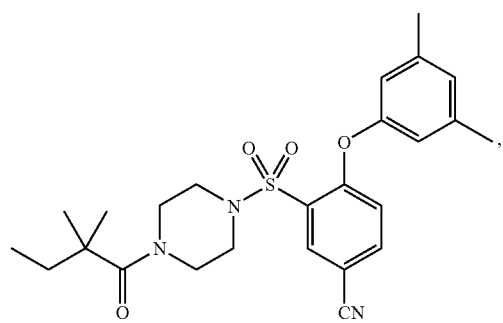
60
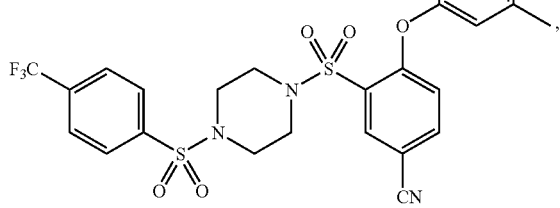
61
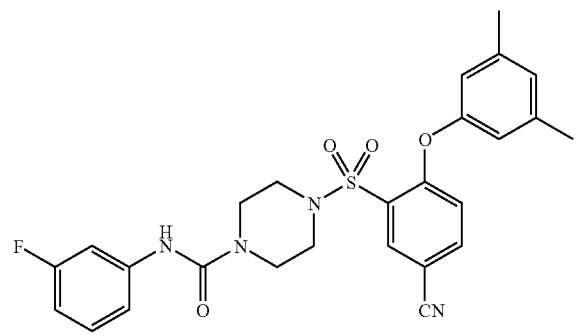
-continued
62
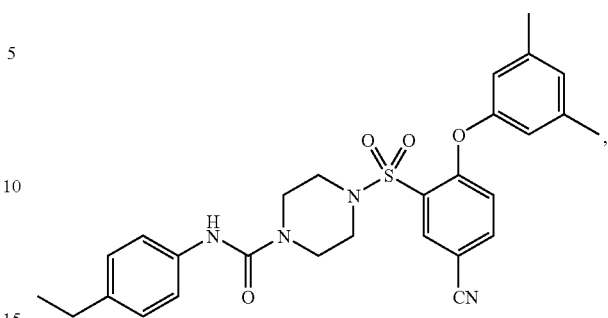
63
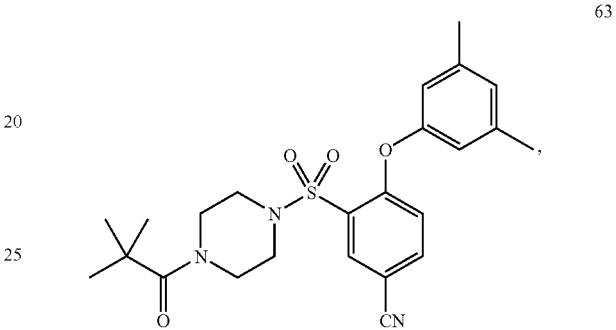
64
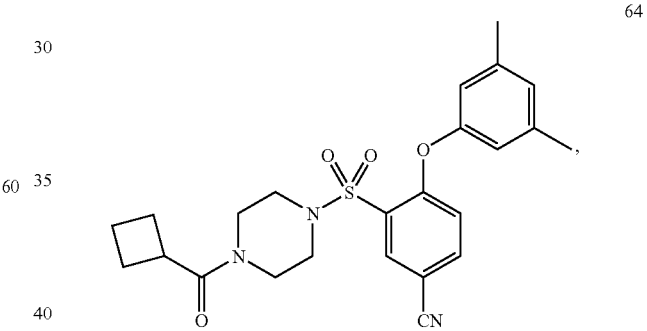
65
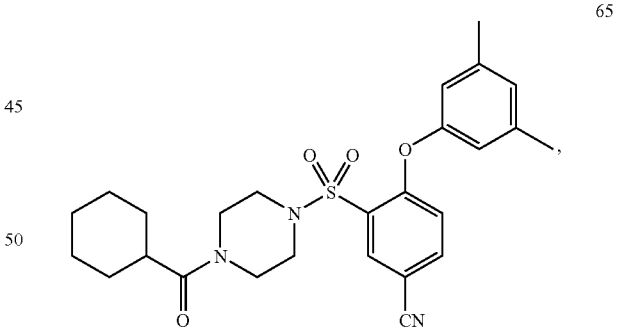
66
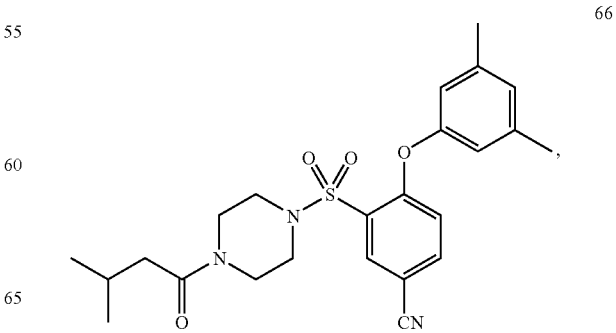

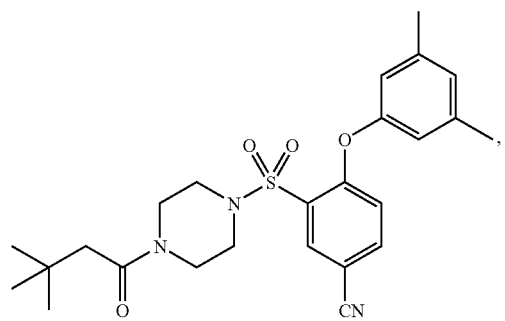
67
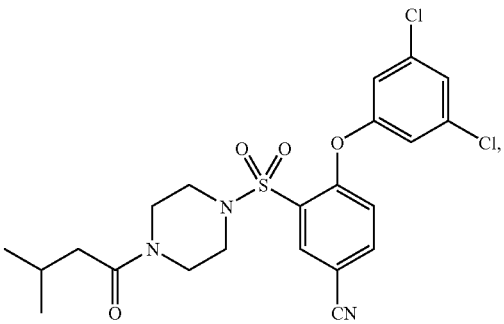
72
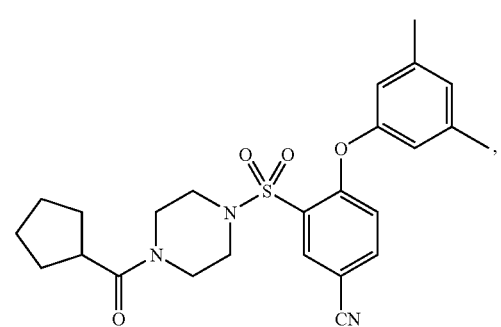
68
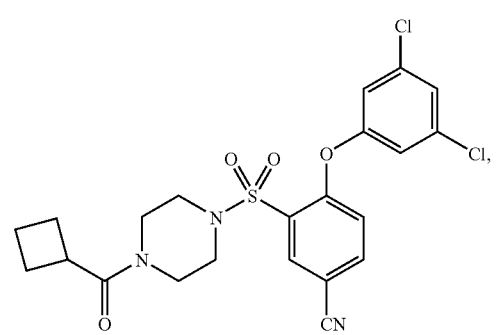
73
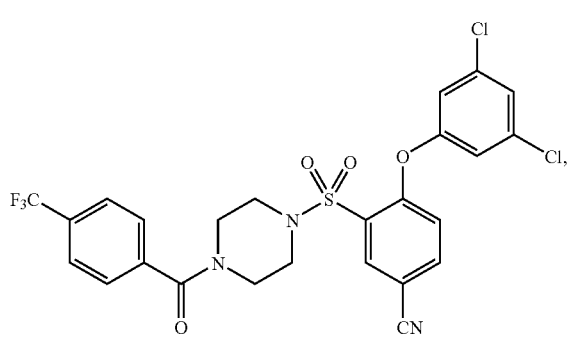
69
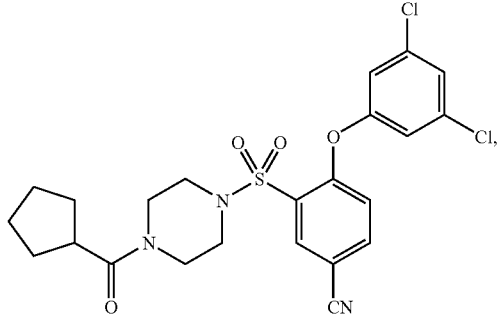
74
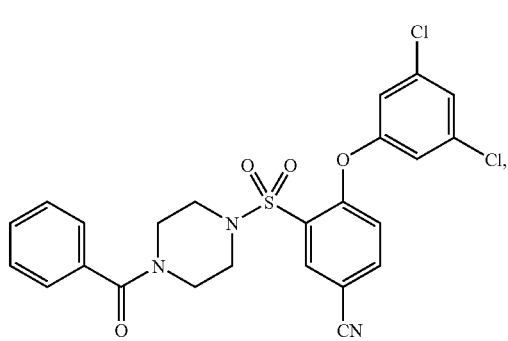
70
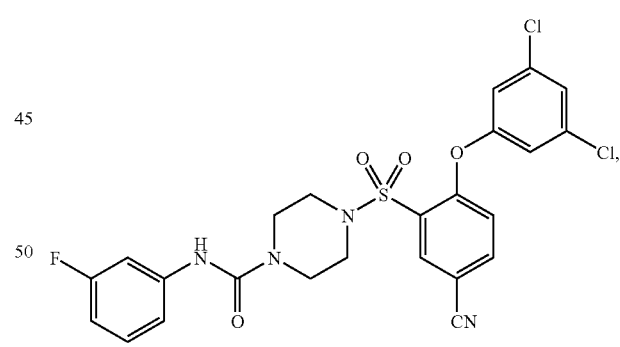
75
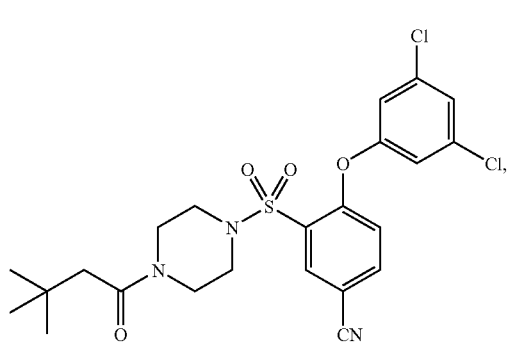
71
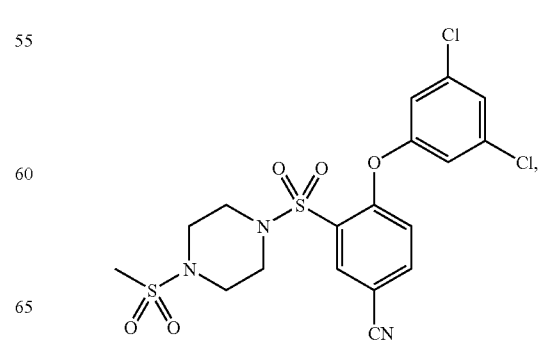
76

77
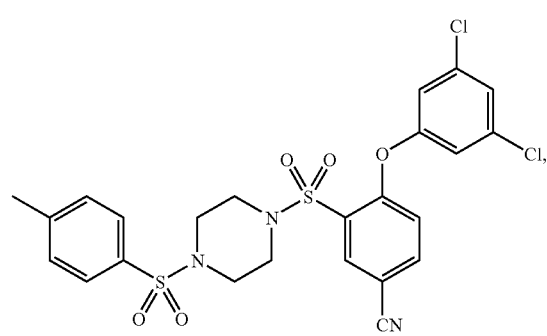
78
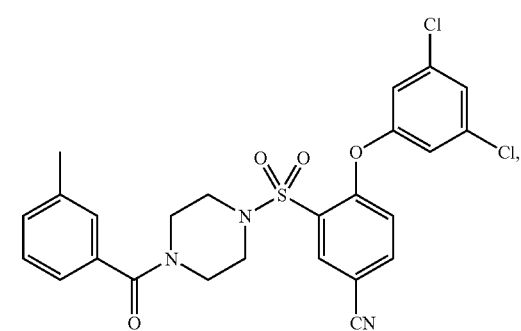
79
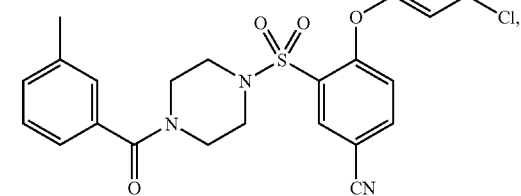
80
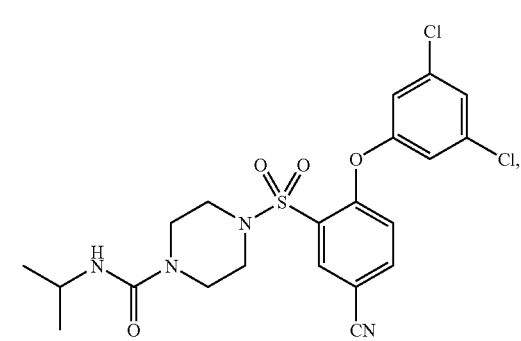
81
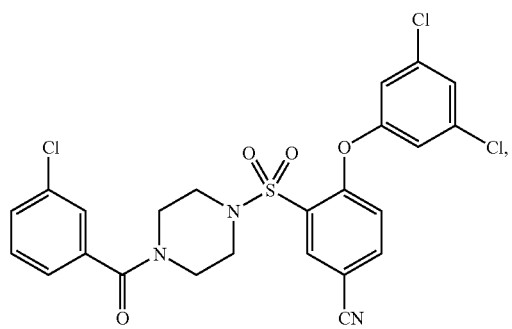
82
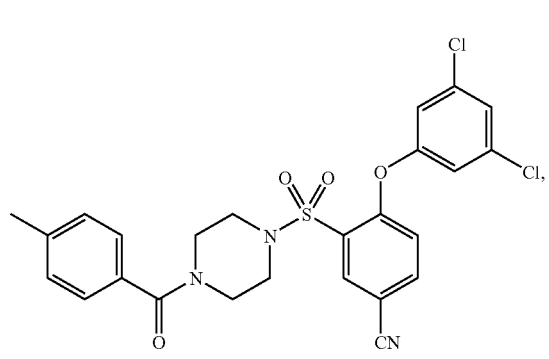
83
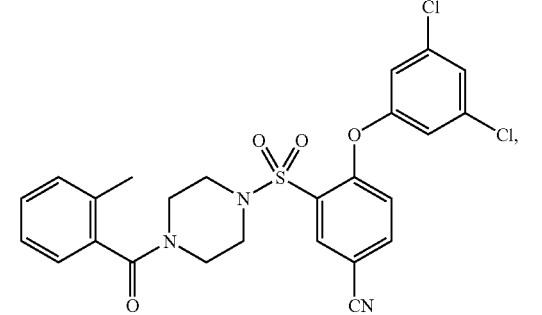
84
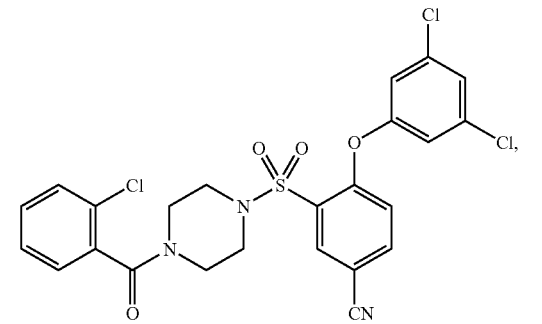
85
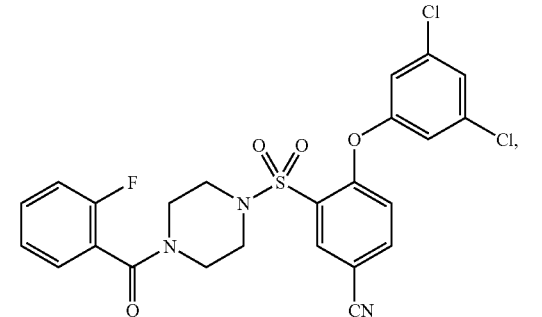

119
-continued
86
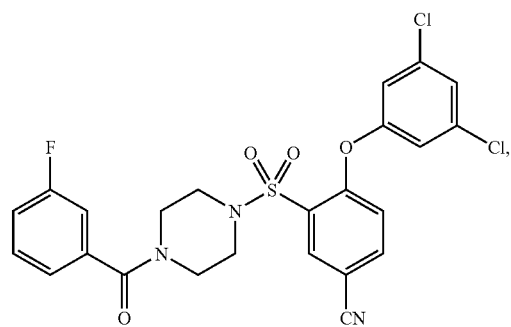
87
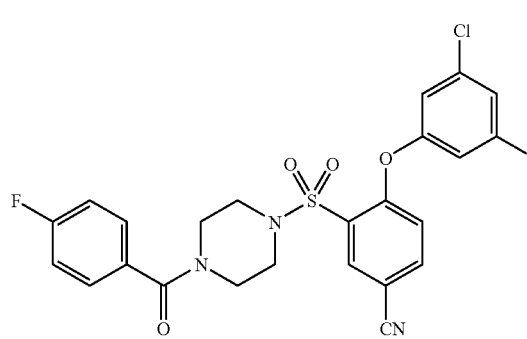
88
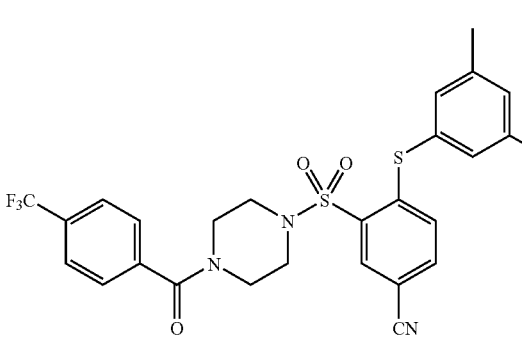
89
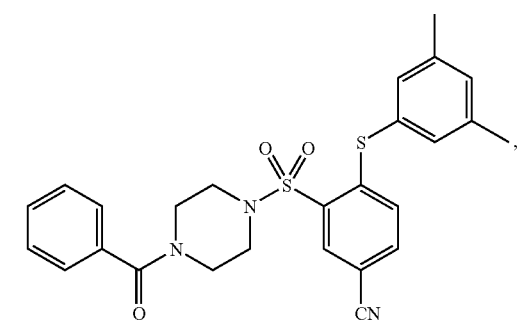
120
-continued
90
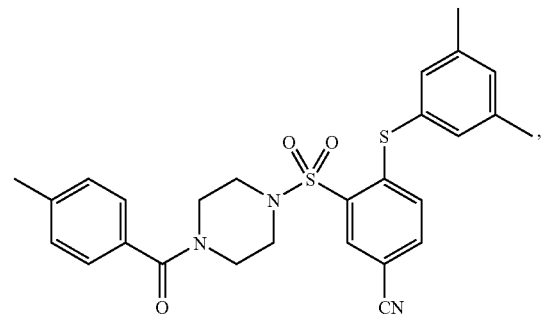
91
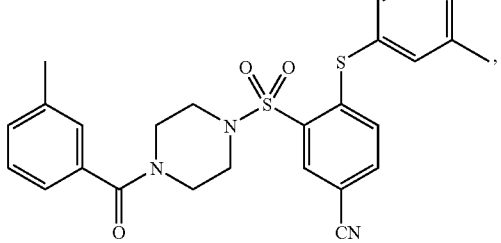
92
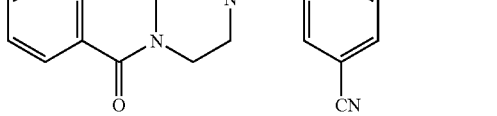
93
94
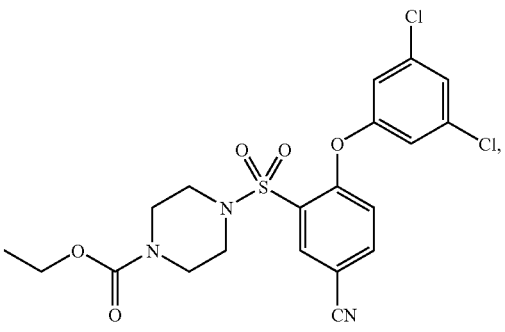

95
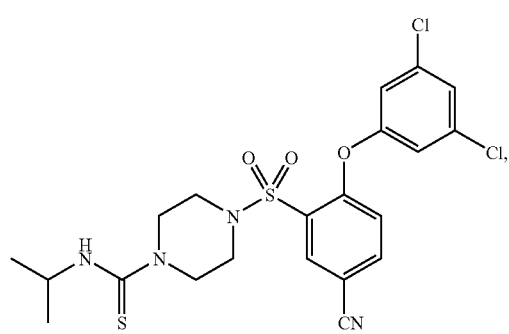
96
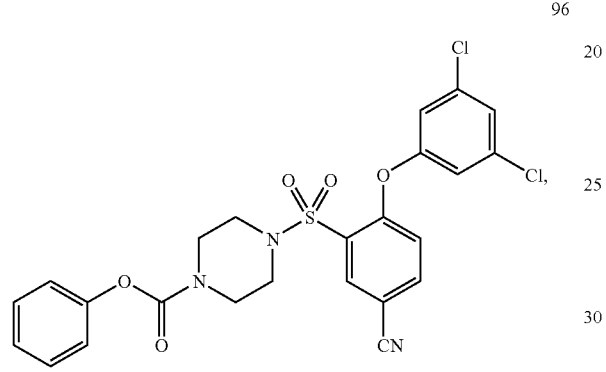
97
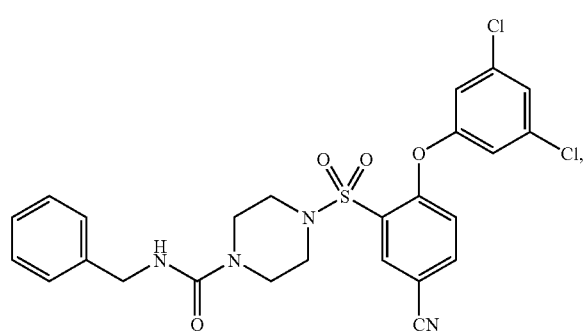
98
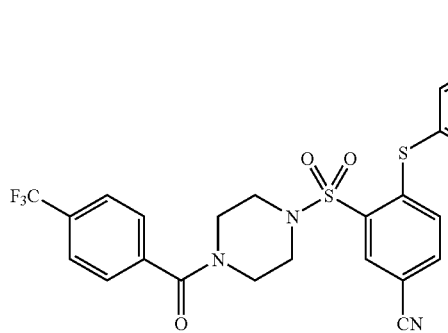
99
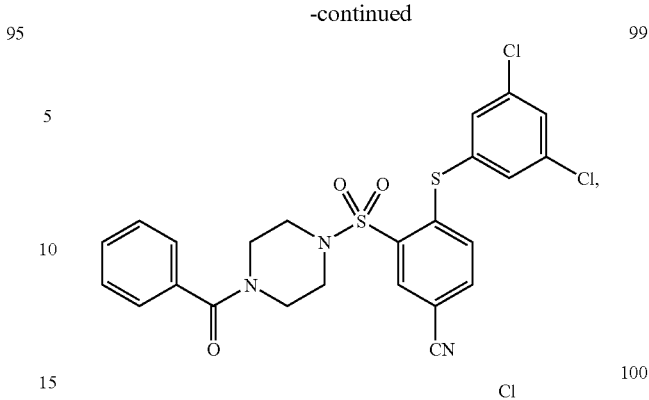
100
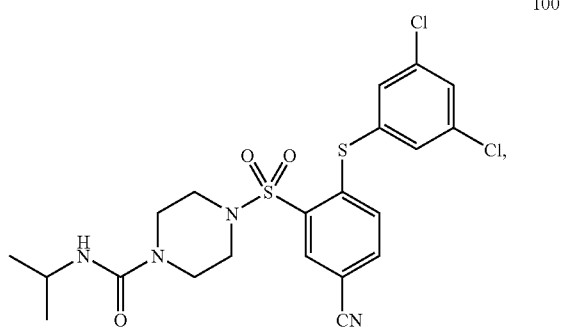
101
102
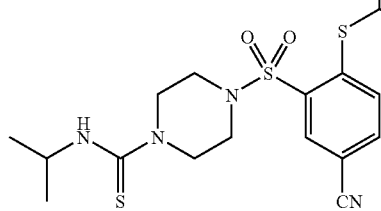
103
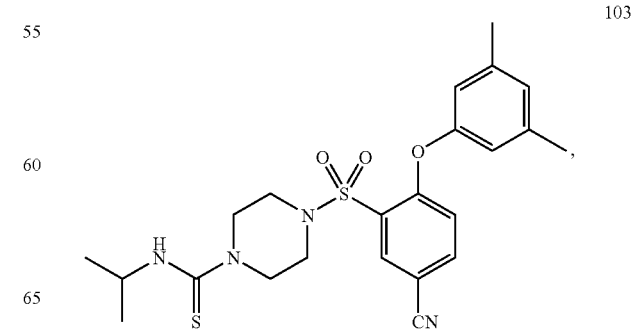

-continued
104
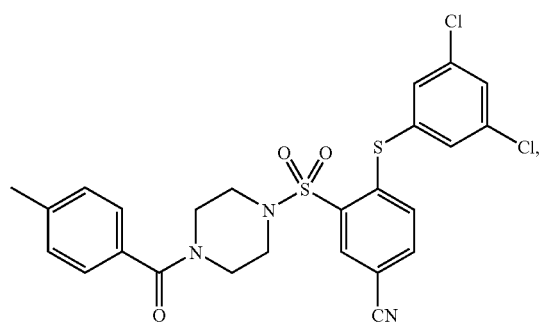
105
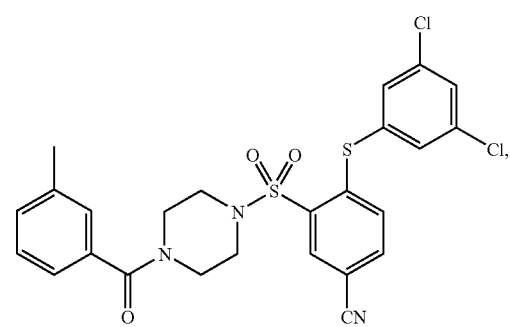
106
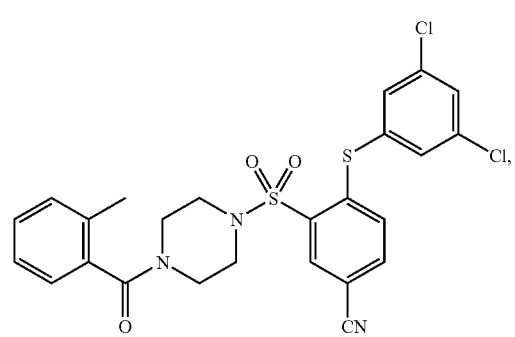
107
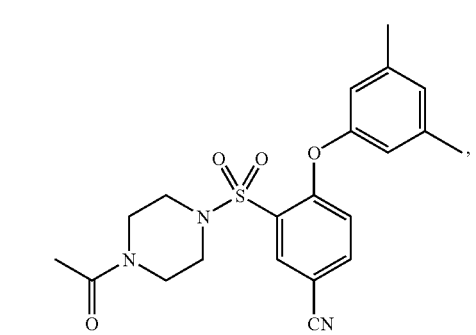
108
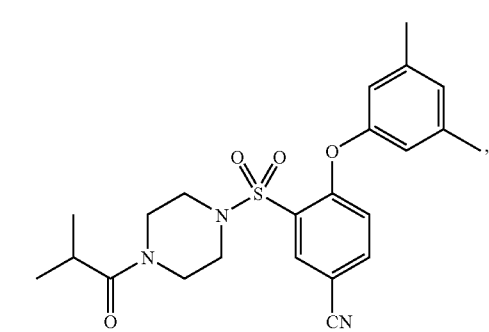
-continued
109
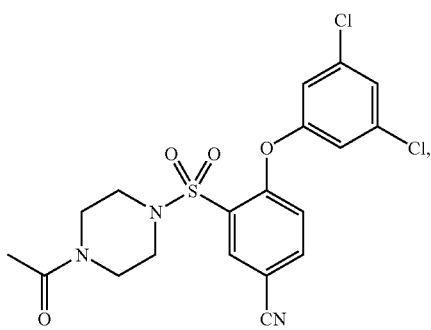
110
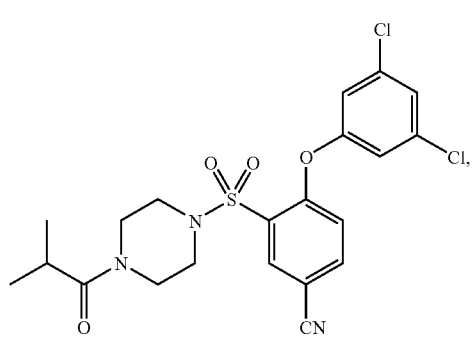
111
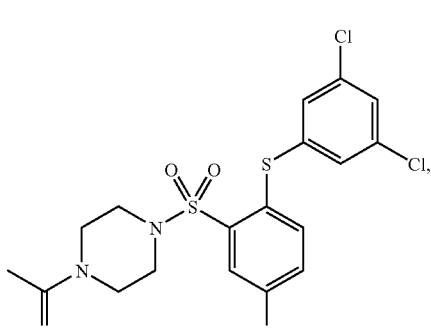
112
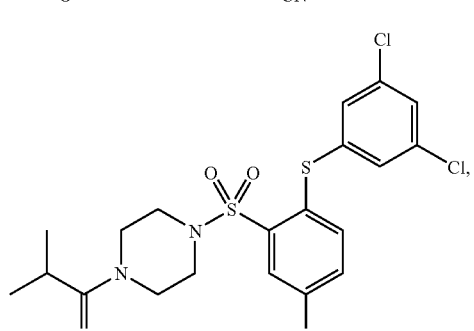
113
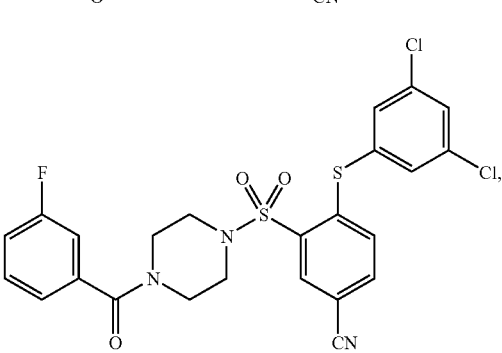

-continued

114

115

116

117

118

119

120

121

122

| 123 | 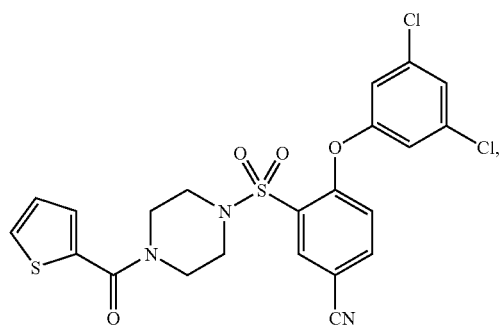 |
| 124 | 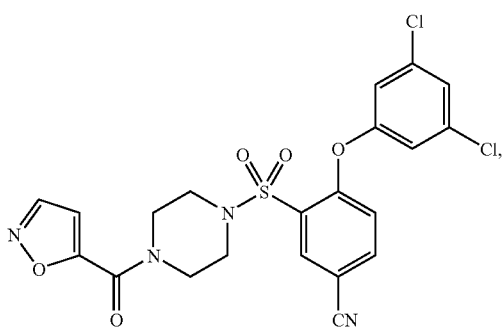 |
| 125 | 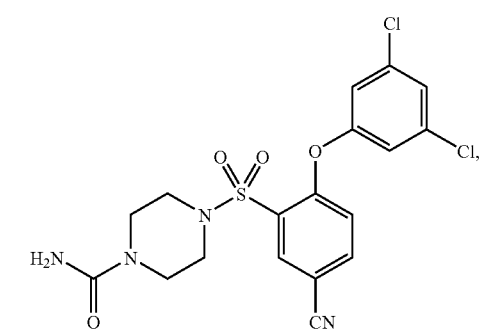 |
| 126 | 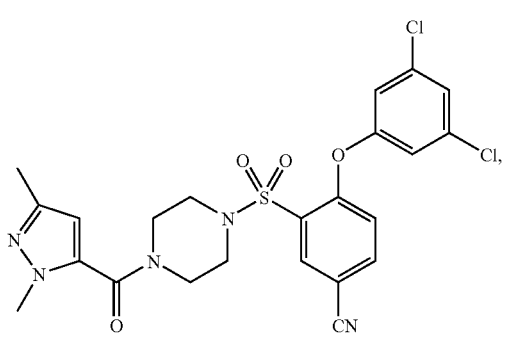 |
| 127 | 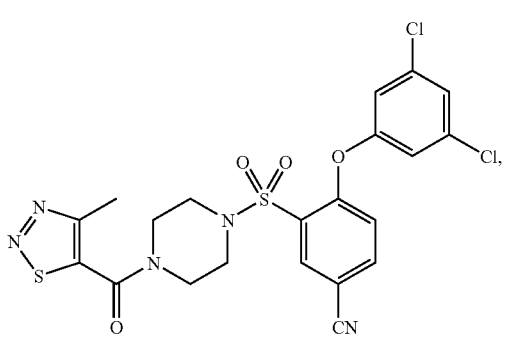 |
| 128 | 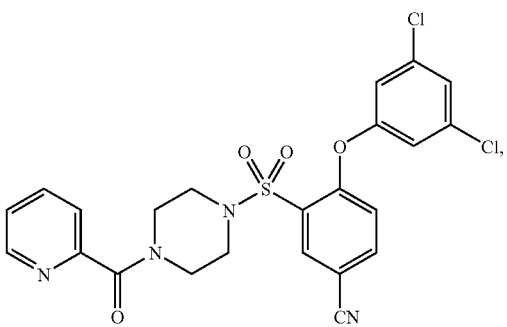 |
| 129 | 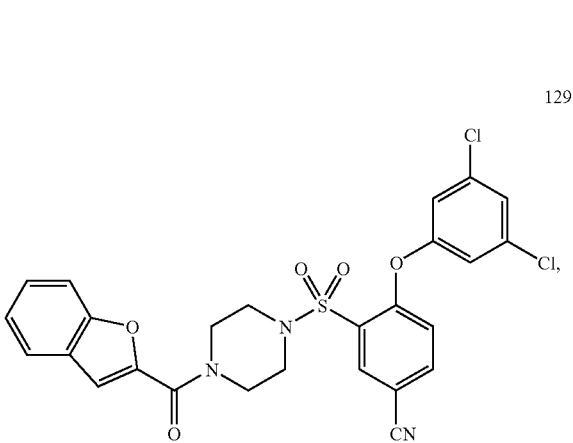 |
| 130 | 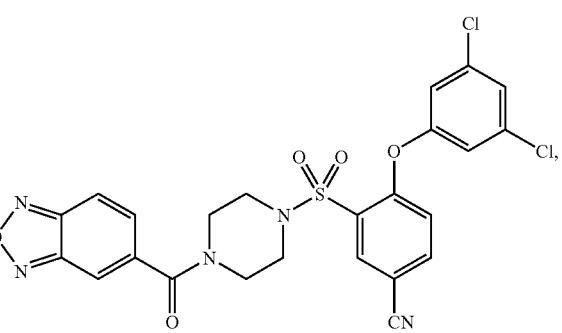 |
| 131 | 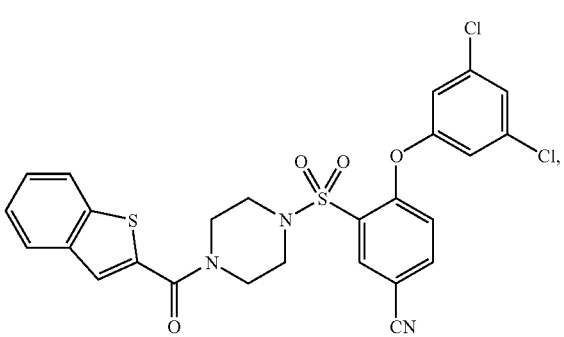 |

129
-continued
130
-continued
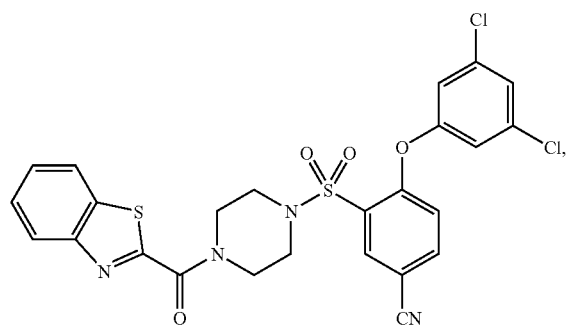
132
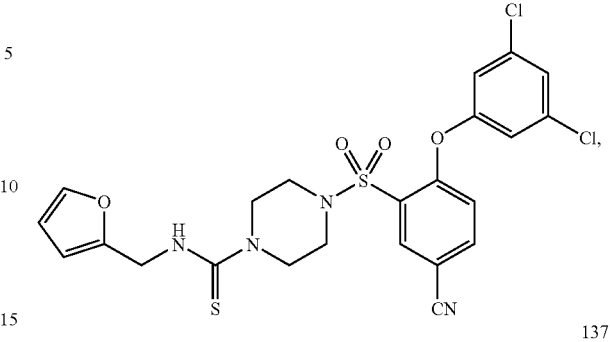
136
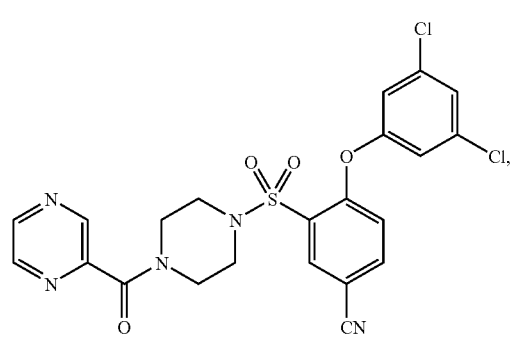
133
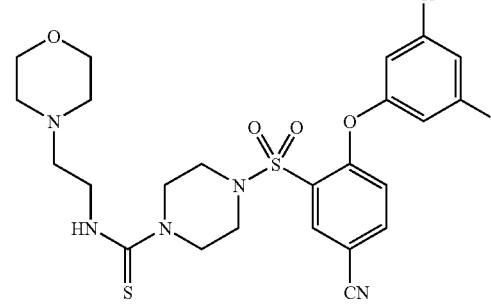
137
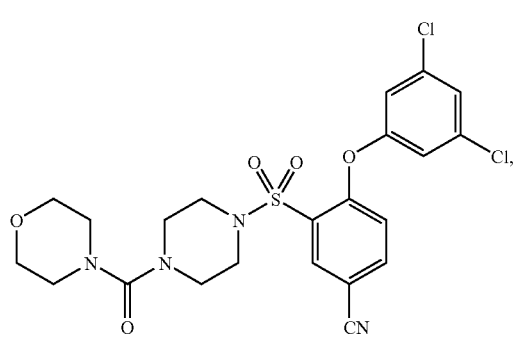
134
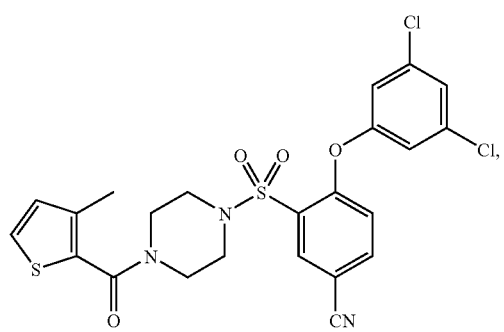
138
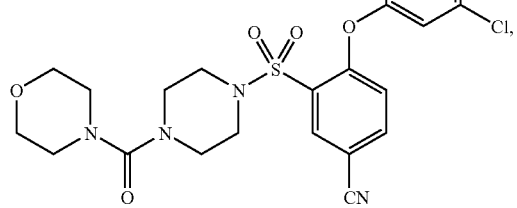
135
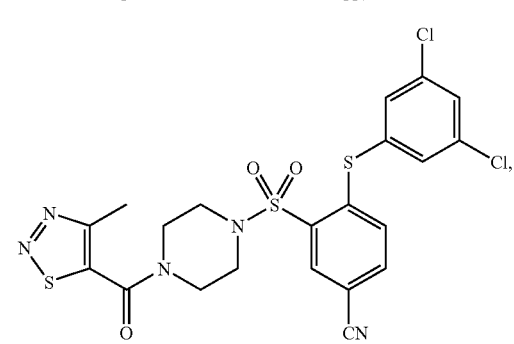
139
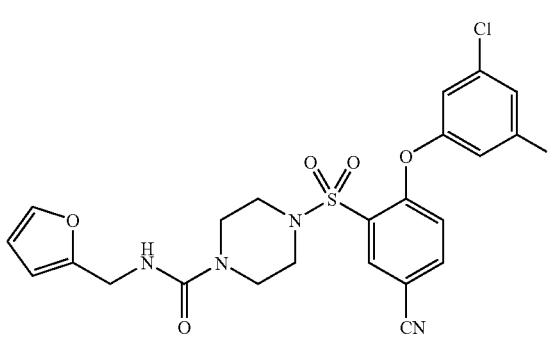
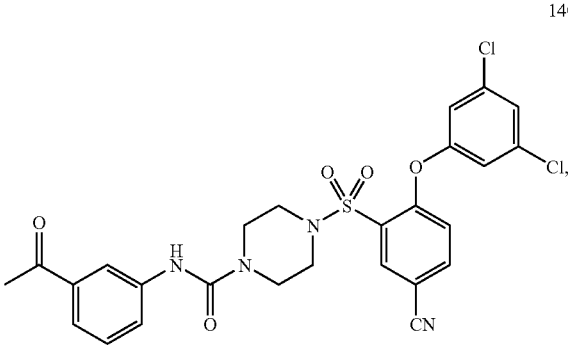
140

-continued
141
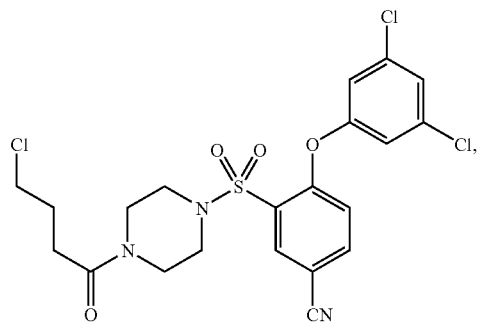
145
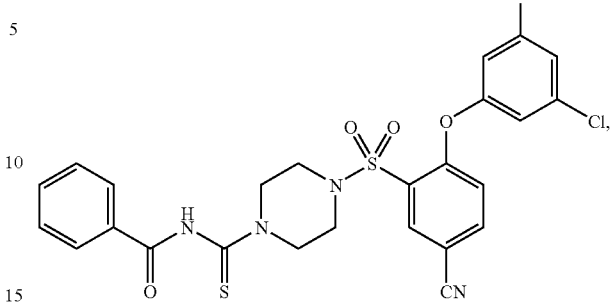
142
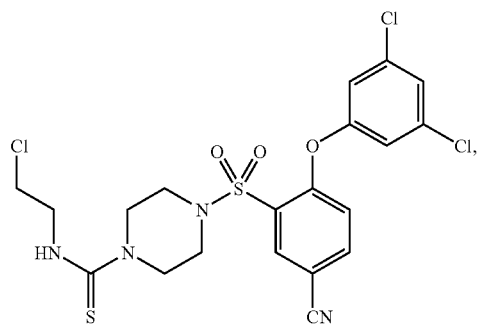
146
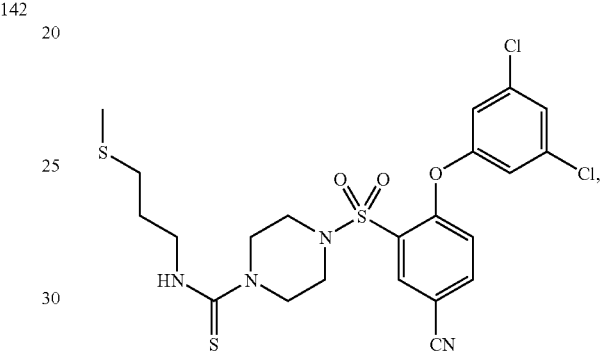
143
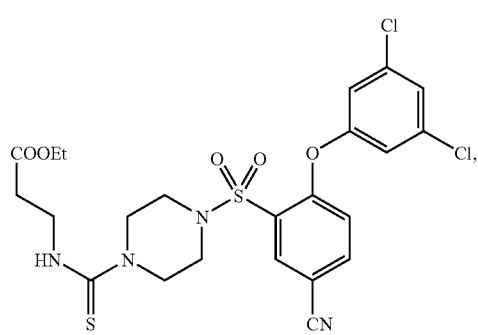
147
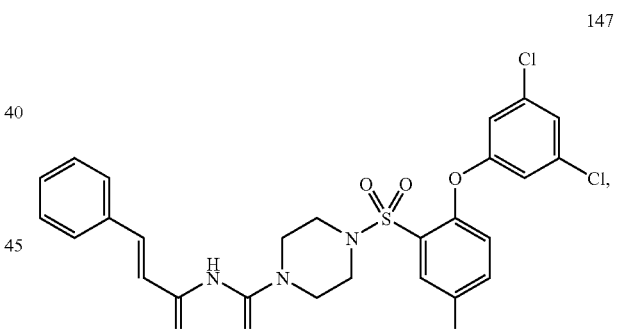
144
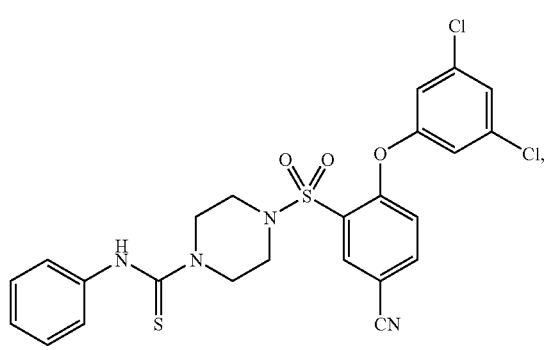
148
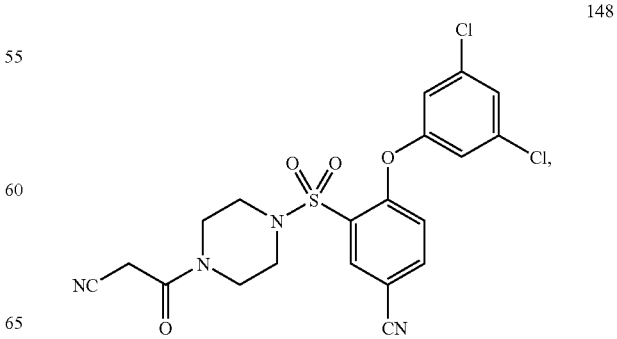

149 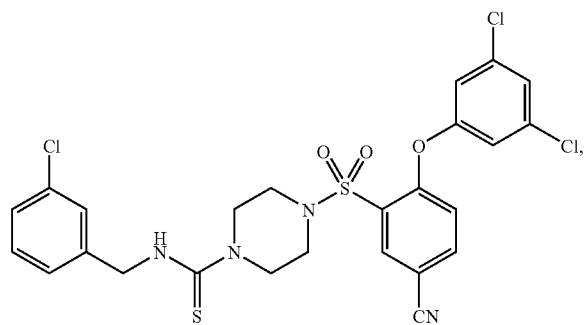
150 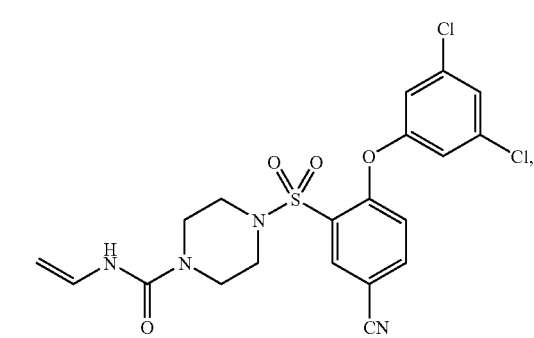
151 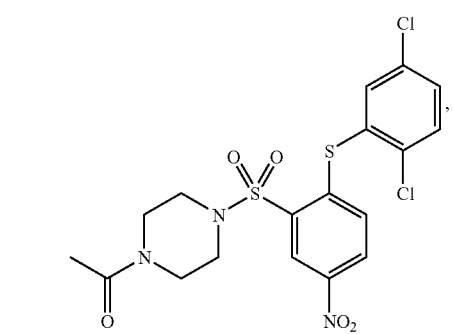
152 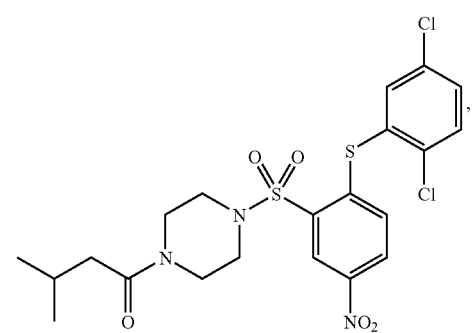
153 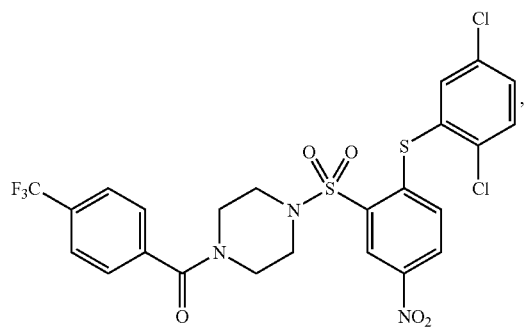
154 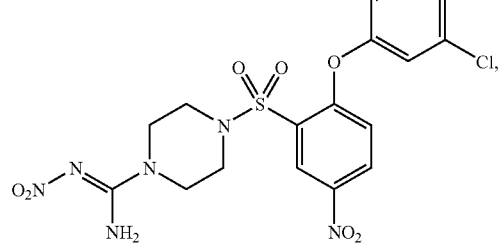
155 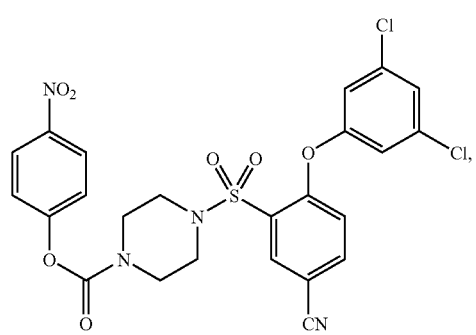
156 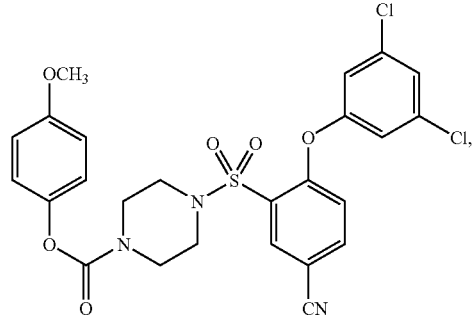
157

158
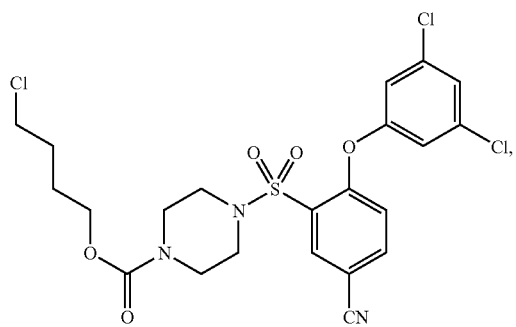
159
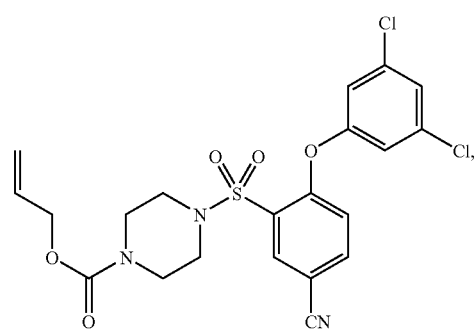
160
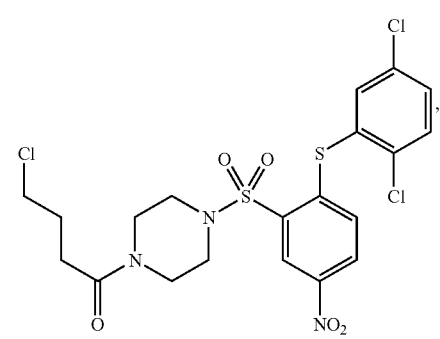
161
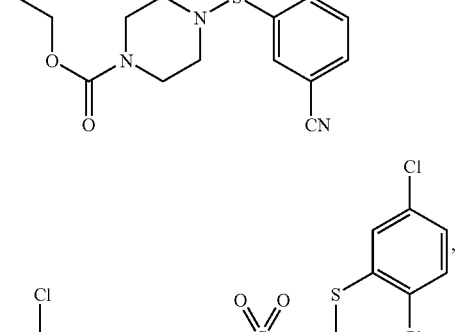
162
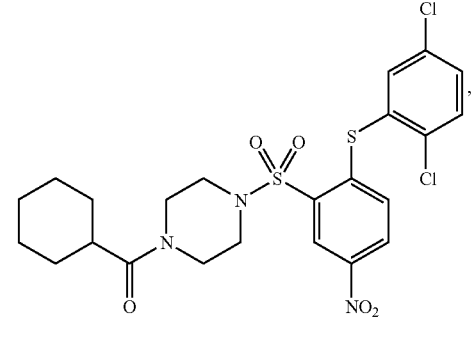
163
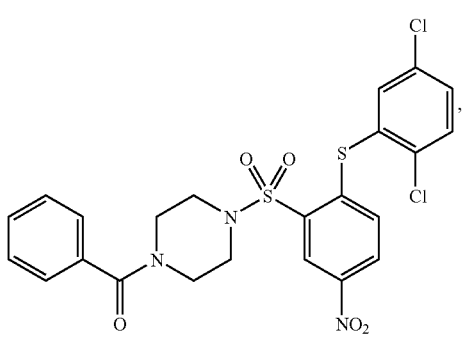
164
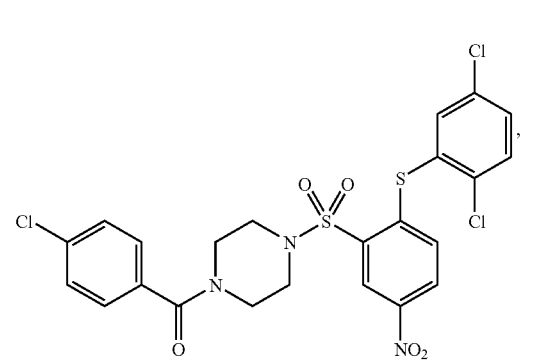
165
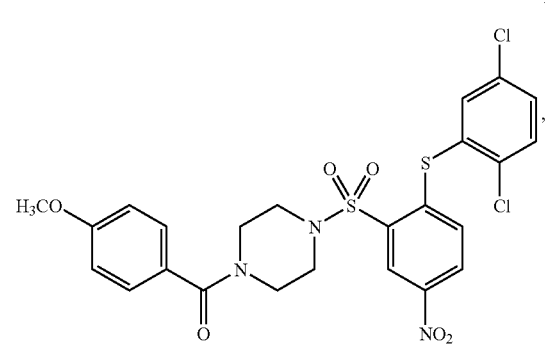
166
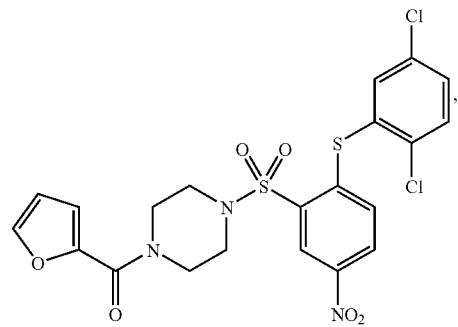

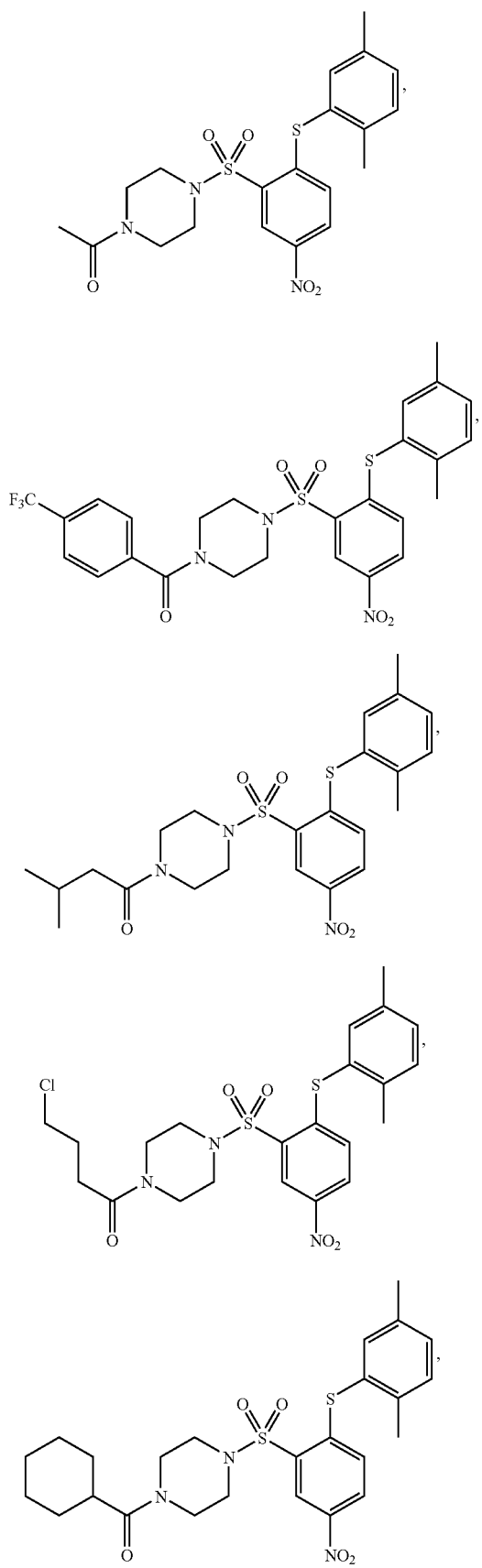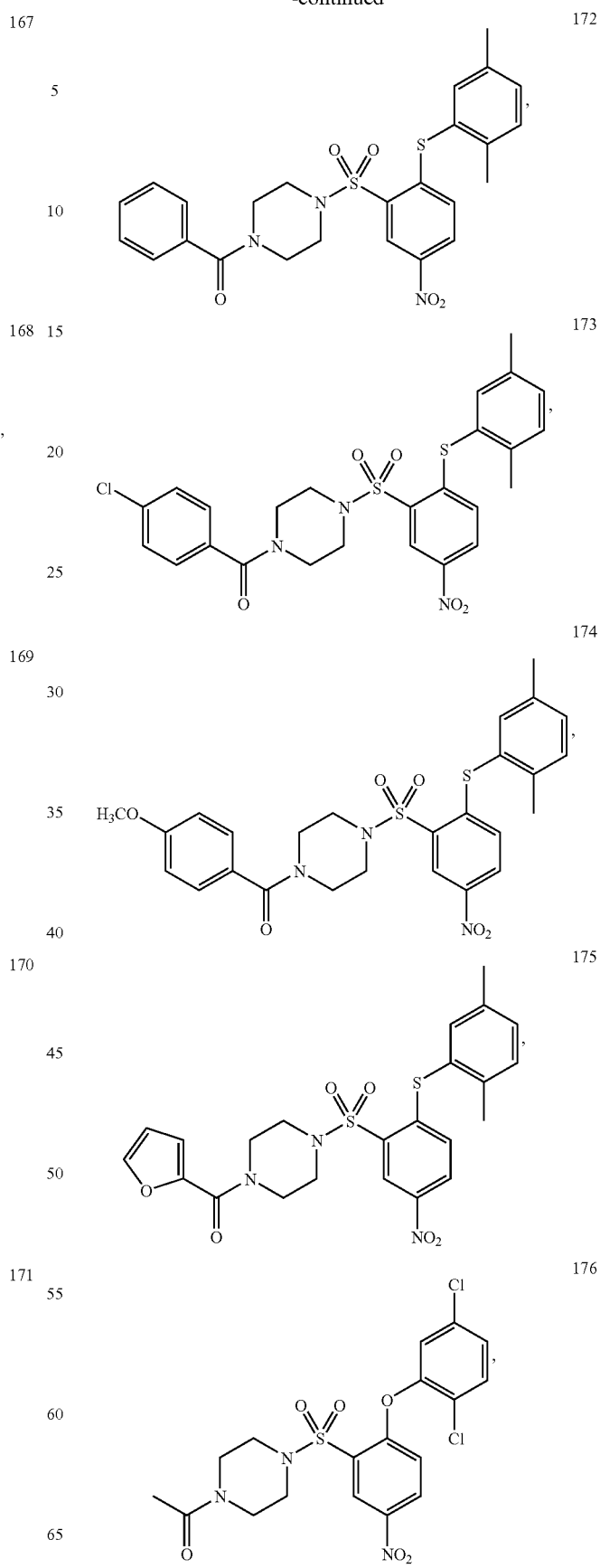

177
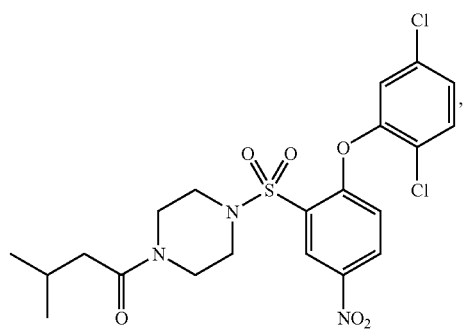
181
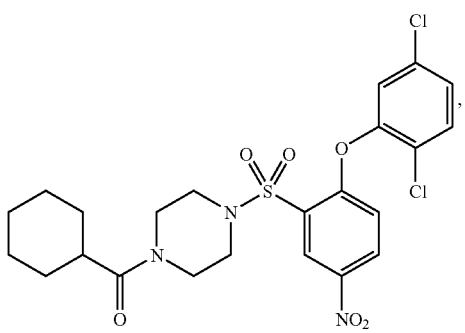
178
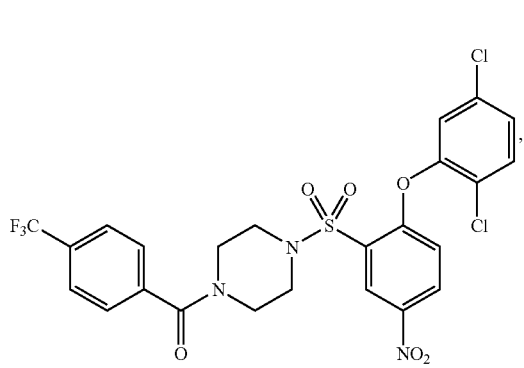
182
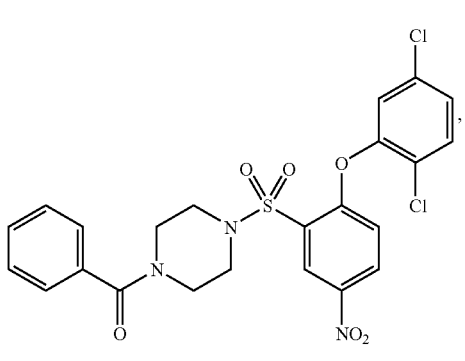
179
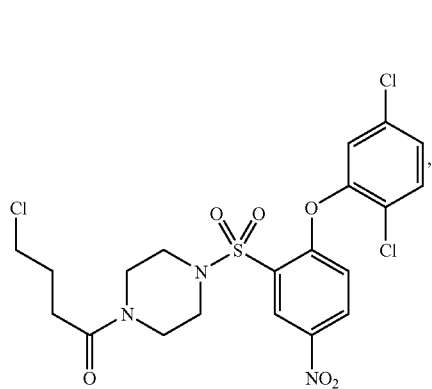
183
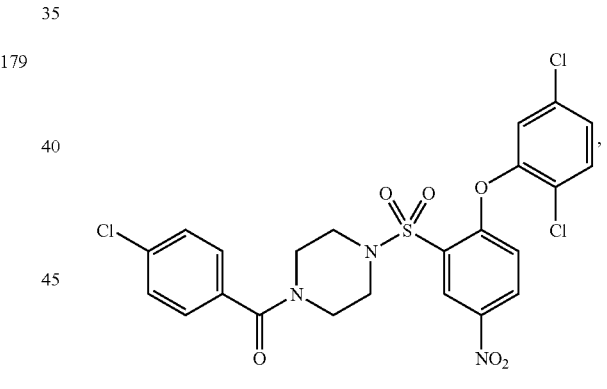
180
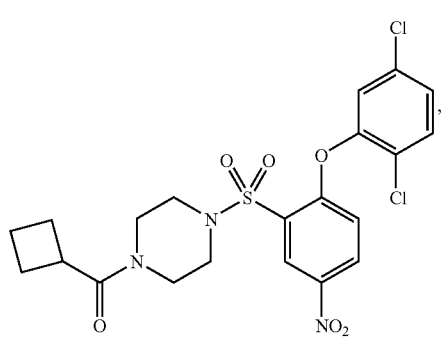
184
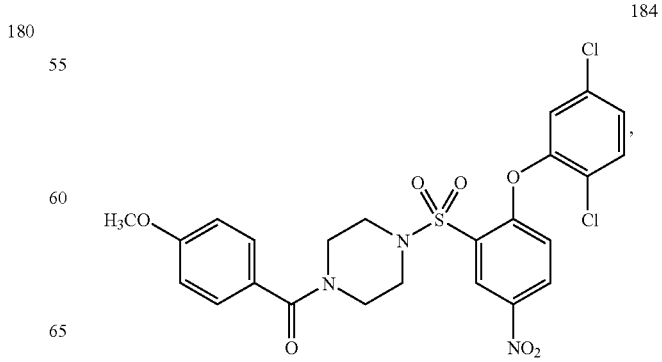

185
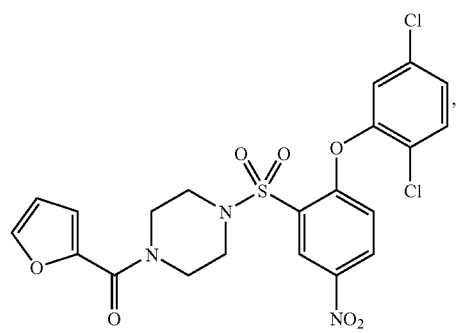
189
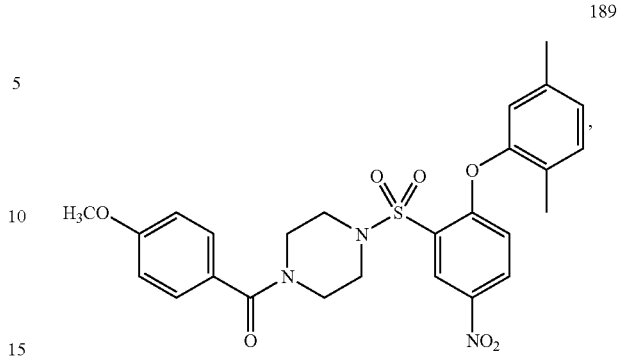
186
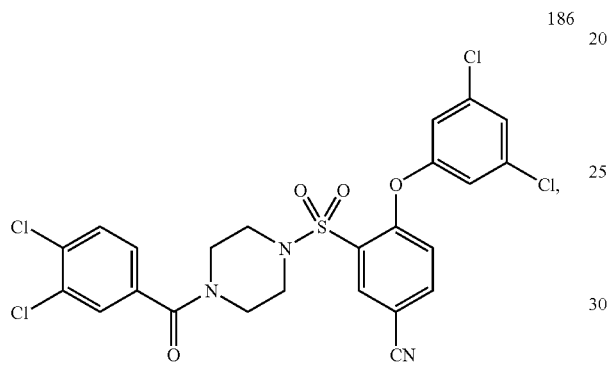
190
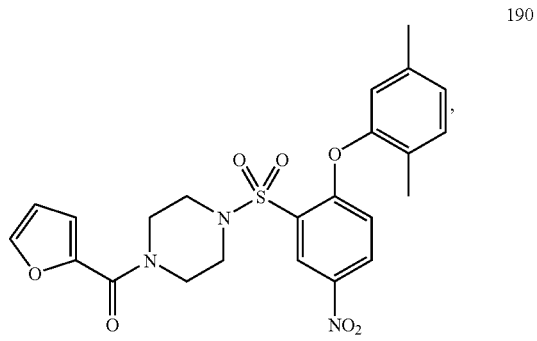
187
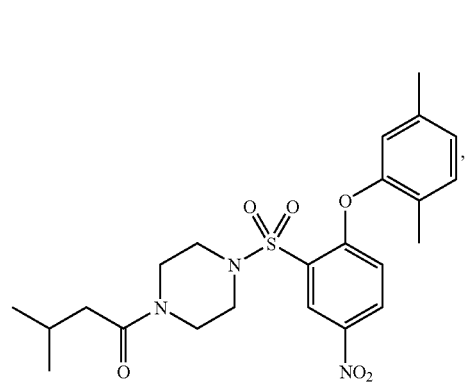
191
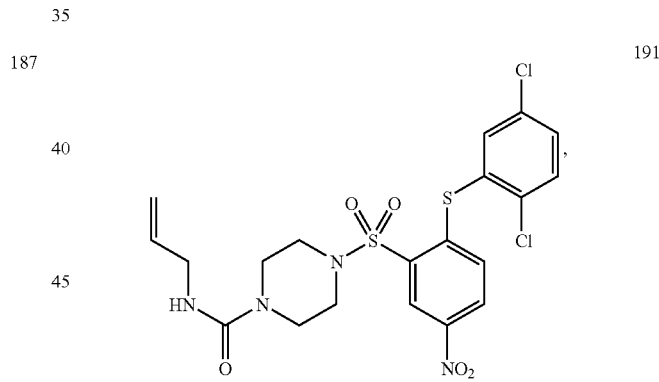
188
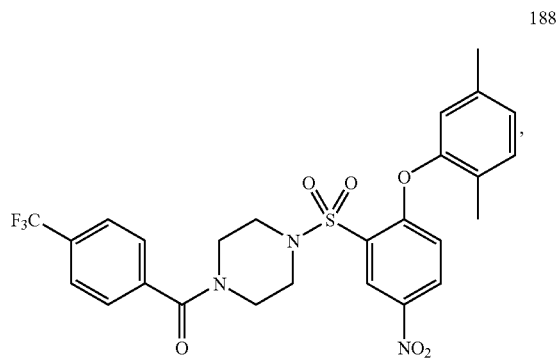
192
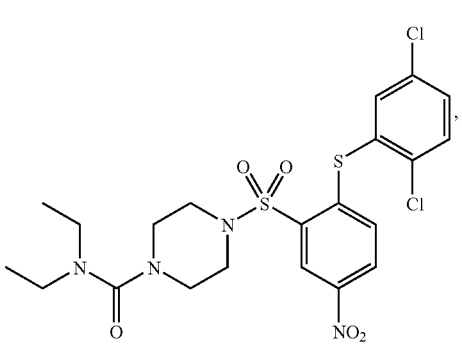

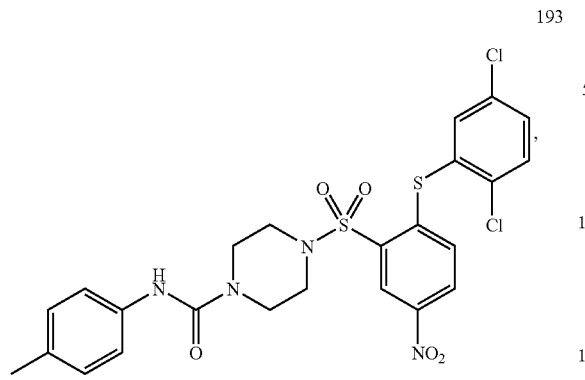
193
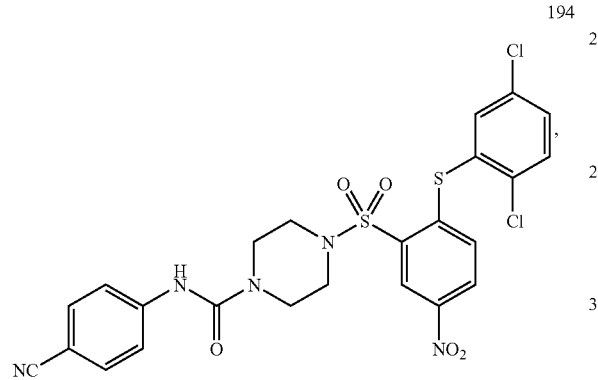
194
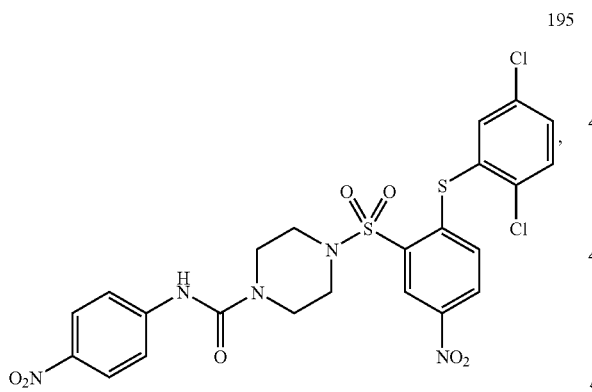
195
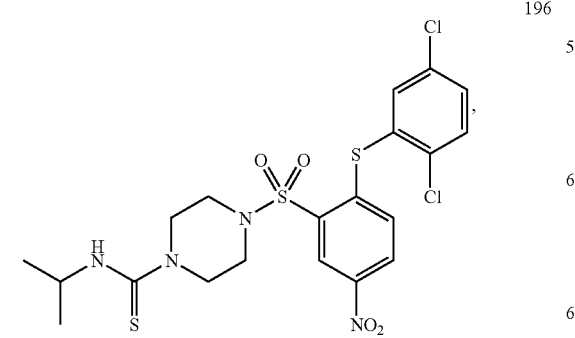
196
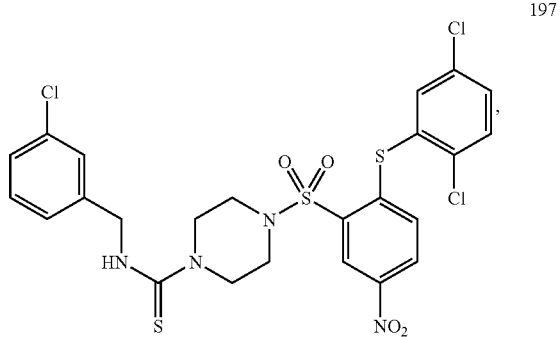
197
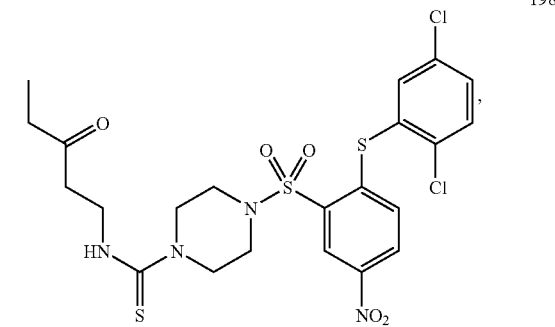
198
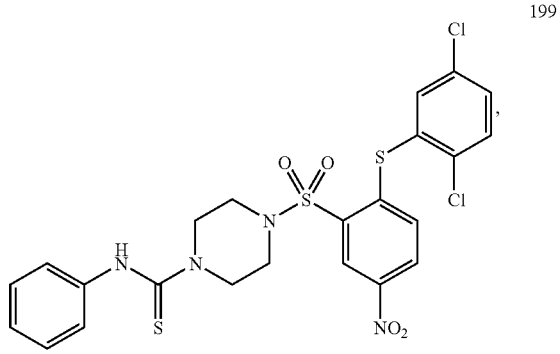
199
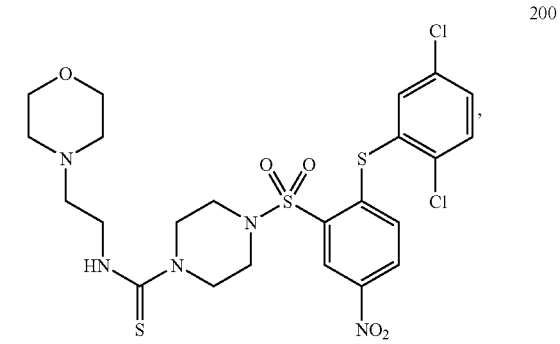
200
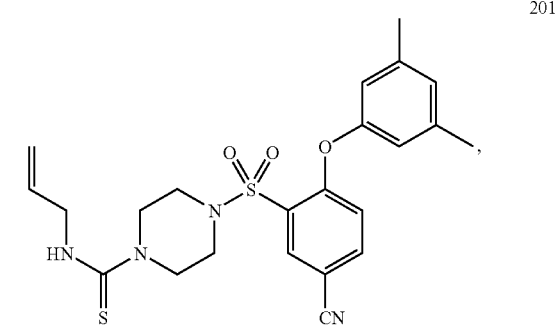
201

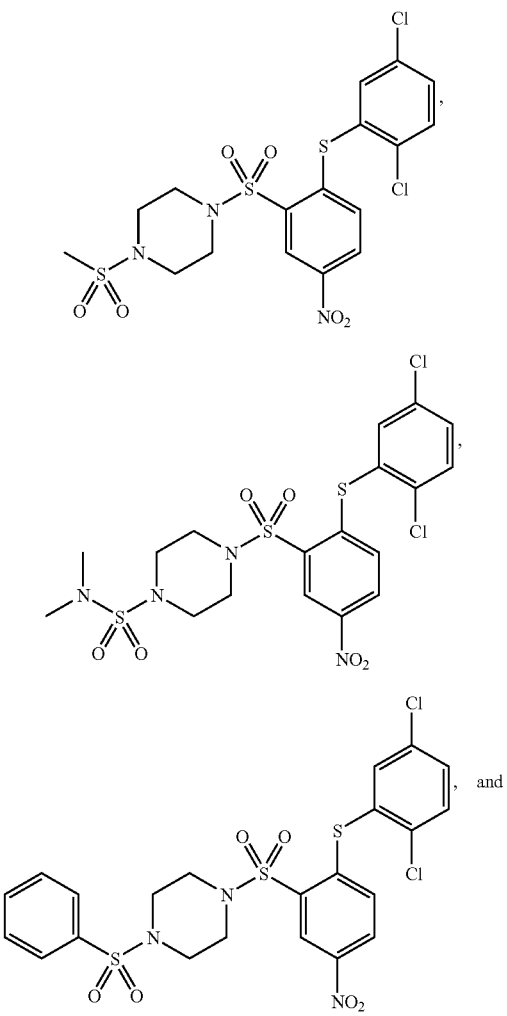

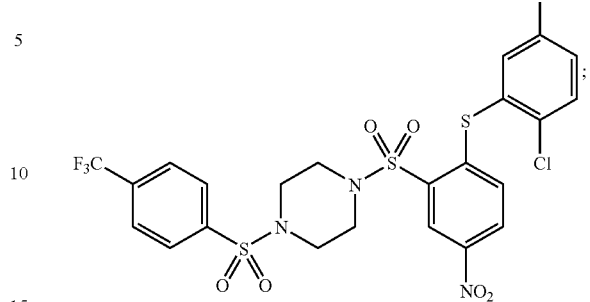

and enantiomers, mixtures of enantiomers, mixtures of two or more diastereomers, tautomers, and mixtures of two or more tautomers thereof; and pharmaceutically acceptable salts and prodrugs thereof.

32. The compound of claim 1, wherein the compound is a hydrochloride salt.

33. A pharmaceutical composition comprising the compound of claim 1, or an enantiomer, a mixture of enantiomers, a mixture of two or more diastereomers, a tautomer, or a mixture of two or more tautomers thereof; or a pharmaceutically acceptable salt or prodrug thereof; and one or more pharmaceutically acceptable carriers or excipients.

34. The pharmaceutical composition of claim 33, further comprising a second therapeutic agent.

35. The pharmaceutical composition of claim 33, wherein the composition is formulated for single dose administration.

36. The pharmaceutical composition of claim 35, wherein the composition is formulated as an oral, parenteral, or intravenous dosage form.

37. The pharmaceutical composition of claim 36, wherein the oral dosage form is a tablet or capsule.

\* \* \* \* \*